United States Patent
Lyznik et al.

(10) Patent No.: US 7,109,390 B2
(45) Date of Patent: Sep. 19, 2006

(54) ALTERNATIVE SPLICING FACTORS POLYNUCLEOTIDES POLYPEPTIDES AND USES THEROF

(75) Inventors: L. Alexander Lyznik, Johnston, IA (US); William J. Gordon-Kamm, Urbandale, IA (US); Huirong Gao, Johnston, IA (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 0 days.

(21) Appl. No.: 10/956,852

(22) Filed: Oct. 1, 2004

(65) Prior Publication Data
US 2005/0138686 A1 Jun. 23, 2005

Related U.S. Application Data

(60) Provisional application No. 60/557,370, filed on Mar. 29, 2004, provisional application No. 60/509,551, filed on Oct. 8, 2003.

(51) Int. Cl.
C12N 15/82 (2006.01)
C12N 5/14 (2006.01)
C07H 21/04 (2006.01)

(52) U.S. Cl. .................... 800/278; 536/23.2; 536/23.6; 435/419; 435/468; 435/320.1

(58) Field of Classification Search ................ 800/279, 800/278; 435/320.1, 419, 471; 536/23.1, 536/23.2, 23.6
See application file for complete search history.

(56) References Cited

OTHER PUBLICATIONS

Lazar G, Schaal T, Maniatis T, and Goodman HM. Identification of a plant serine-arginine-rich protein similar to the mammalian splicing factor SF2/ASF. (1995) PNAS vol. 92, pp. 7672-7676.*

* cited by examiner

*Primary Examiner*—Ashwin D. Mehta
*Assistant Examiner*—Cathy Kingdon Worley
(74) *Attorney, Agent, or Firm*—Pioneer Hi-Bred International, Inc.

(57) ABSTRACT

The invention provides isolated polynucleotides and their encoded proteins that are involved in splicing or modulating splicing activity. The invention further provides recombinant expression cassettes, host cells, transgenic plants, and antibody compositions. The present invention provides methods and compositions relating to altering splicing protein content and/or composition of plants.

13 Claims, No Drawings

ALTERNATIVE SPLICING FACTORS POLYNUCLEOTIDES POLYPEPTIDES AND USES THEROF

This application claims priority to U.S. Ser. No. 60/509,551 filed Oct. 8, 2003 and to U.S. Ser. No. 60/557,370 filed Mar. 29, 2004 the disclosures of which are incorporated herein by reference.

TECHNICAL FIELD

The present invention relates generally to plant molecular biology. More specifically, it relates to nucleic acids and methods for modulating their expression in plants in order to modulate gene regulation and to selectively express polypeptides.

BACKGROUND OF THE INVENTION

A complex network of regulatory pathways control gene expression in eukaryotes. Environmental constraints, such as nutrient availability, mitogenic signals such as growth factors or hormones, as well as developmental cues such as the transition from vegetative to reproductive, modulate transcription and translation in plants. Genes which are involved in this modulation can be introduced into a plant and used to affect phenotype in adventitious or desirable ways.

The development of methods for the introduction of foreign genes into organisms has had a profound impact on fields of medicine and agriculture and has further expanded understanding of regulatory mechanisms involved in gene expression. While the movement of genes within plant species or between closely related plant species by traditional methods based on sexual reproduction has played an important role in crop improvement for most of this century, the pace of crop improvement by such methods has been slow and limiting due to the reliance on naturally occurring genes. Recent advances in the field of genetic engineering have led to the development of genetic transformation methods that allow the introduction of recombinant DNA into organisms. The recombinant DNA methods which have been developed have greatly extended the sources from which genetic information can be obtained for crop improvement. Recently, new crop plant varieties, developed through recombinant DNA methods, have reached the marketplace. Genetically engineered soybeans, maize, canola, cotton and other crops are now widely utilized by North America farmers.

Genes from plants and other entirely unrelated organisms are being cloned, genetic regulatory signals are being deciphered, and genes conferring new traits, are being transferred. Introduction of single genes or of combinations of genes through stacking pose challenges in controlling the expression of the transferred genes. Many of the recent advances in plant science have resulted from application of the analytical power of recombinant DNA technology coupled with plant transformation and an understanding of gene regulatory processes. These approaches facilitate studies of the effects of specific gene alterations and additions on plant development and physiology and make possible the direct manipulation of genes to bio-engineer improved plant varieties.

While some success has already been achieved in improving crop plants through the introduction and regulation of recombinant DNA, the progress of genetic engineers working to improve many important crop species is impeded by inefficient methods and limited choices of gene regulation in crop plants. Thus, improved methods for controlling gene expression in plants and the transformed plants regenerated there from are desired.

SUMMARY OF THE INVENTION

Methods and compositions are provided for producing transformed plant, cells, plants, plant embryos and increasing plant transformation efficiency. The methods involve transforming a plant cell with a splicing factor polynucleotide or introducing a splicing factor polypeptide or RNA. Expression of the splicing factor may be transient, stable or inducible. Levels may be modulated to modulate gene expression, increase transformation efficiency or to modulate splicing to modulate phenotype; especially phenotypes associated with agronomic traits. The methods and compositions of the invention find use in agriculture, particularly in modulating gene expression in crop plants, and in transforming crop plants that display low transformation efficiencies with existing transformation methods. The methods and compositions of the invention are also useful in providing selective expression of polypeptides through alternative splicing mechanisms. Also provided are transgenic plants and seeds thereof.

DETAILED DESCRIPTION OF THE INVENTION

Sequences

Seq. ID no. 1 is the DNA sequence of zmSRp30 (ATG start bp-40, TGA stop bp-820).
Seq. ID no. 2 is the polypeptide sequence of zmSRp30.
Seq. ID no. 3 is the DNA sequence of zmSRp30' (ATG start bp-40, TGA stop bp-763).
Seq. ID no. 4 is the polypeptide sequence of zmSRp30'.
Seq. ID no. 5 is the DNA sequence of zmSRp31 (ATG start bp-82, TGA stop bp-910).
Seq. ID no. 6 is the polypeptide sequence of zmSRp31.
Seq. ID no. 7 is the DNA sequence of zmSRp31' (ATG start bp-82, TAA stop bp-841).
Seq. ID no. 8 is the polypeptide sequence of zmSRp31'.
Seq. ID no. 9 is the DNA sequence of zmSRp32 (ATG start bp-104, TGA stop bp-955).
Seq. ID no. 10 is the polypeptide sequence of zmSRp32.
Seq. ID no. 11 is the DNA sequence of zmSRp32' (ATG start bp-104, TGA stop bp-875).
Seq. ID no. 12 is the polypeptide sequence of zmSRp32'.
Seq. ID no. 13 is the DNA sequence of zmSRp32" (ATG start bp-104, TAG stop bp-554).
Seq. ID no. 14 is the polypeptide sequence of zmSRp32".
Seq. ID no. 28 the DNA sequence of the genomic zmSRp31.
Seq. ID no. 29 the DNA sequence of the genomic zmSRp32.
Seq. ID no. 30 the DNA sequence of the genomic zmSRp30.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, rolling circle, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herewithin, "cereal grasses" includes wheat, oat and corn.

As used herein, "chromosomal region" includes reference to a length of chromosome that can be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Proc. Natl. Acad. Sci. U.S.A. 82:2306–2309 (1985)), or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al., Nucl. Acids Res. 17:477–498 (1989)). Thus, the maize preferred codon for a particular amino acid can be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, catalytically active form of the specified protein. A full-length sequence can be determined by size comparison relative to a control that is a native (non-synthetic) endogenous cellular form of the specified nucleic acid or protein. Methods to determine whether a sequence is full-length are well known in the art including such exemplary techniques as northern or western blots, primer extension, S1 protection, and ribonuclease protection. See, e.g., Plant Molecular Biology: A Laboratory Manual, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition, regulatory signals, neighboring sequence, and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell that contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledenous plant cells. One monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). "Introduced" may also refer to crossing one plant containing a nucleic acid to another plant so as to incorporate the nucleic acid in their progeny.

The term "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA that has been altered, by non-natural, synthetic (i.e., "man-made") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids that are "isolated" as defined herein, are also referred to as "heterologous" nucleic acids.

As used herein, "splicing factor nucleic acid" means a nucleic acid comprising a polynucleotide "splicing factor polynucleotide" encoding a splicing factor polypeptide.

"As used herein, "recalcitrant" means having a low level of transformation efficiency with few or no transgenic events per unit time and resources. Thus, a plant that is recalcitrant to transformation, in the current art, has a transformation efficiency that is less than GS3. For example, low rates of regeneration, embryogenesis and/or increased susceptibility to increased susceptibility to cell damage may be factors leading to exhibiting recalcitrant characteristics.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers. A "selectable marker" refers to a trait that aids in the identification of desired characteristics. For example, the "selectable marker" bar confers bialaphos resistance upon the acquiring organism allowing identification through growth on the normally toxic bialaphos.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules that comprise and substantially represent the entire genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., Molecular Cloning—A Laboratory Manual, 2nd ed., Vol. 1–3 (1989); and Current Protocols in Molecular Biology, F. M. Ausubel et al., Eds. *Current Protocols*, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A plant of interest is *Zea mays*.

As used herein, "polynucleotide" includes reference to a deoxyribopolynucleotide, ribopolynucleotide, or analogs thereof, that have the essential nature of a natural ribonucleotide in that they hybridize to nucleic acids in a manner similar to naturally occurring nucleotides. A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, Proteins—Structure and Molecular Properties, 2nd ed., T. E. Creighton, W. H. Freeman and Company, New York (1993). Many detailed reviews are available on this subject, such as, for example, those provided by Wold, F., Posttranslational Protein Modifications: Perspectives and Prospects, pp. 1–12 in Posttranslational Covalent Modification of Proteins, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y., Acad. Sci. 663:48–62 (1992). It will be appreciated, as is well known and as noted above, that polypeptides are not always entirely linear. For instance, polypeptides may be branched as a result of ubiquitination, and they may be circular, with or without branching, generally as a result of post translation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionine-less amino terminal variants of the protein of the invention. In general, as used herein, the term polypeptide encompasses all such modifications, particularly those that are present in polypeptides synthesized by expressing a polynucleotide in a host cell.

As used herein "promoter" includes reference to a region of DNA upstream from the start of transcription that is involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". A "cell type" promoter primarily drives expression in certain cell types in one or more organs, for example, vascular cells in roots or leaves. An "inducible" promoter is a promoter that is under environmental control. Examples of environmental conditions that may effect transcription by inducible promoters include anaerobic conditions or the presence of light. Tissue-preferred, cell type, and inducible promoters constitute the class of "non-constitutive" promoters. A "constitutive" promoter is a promoter that is active under most environmental conditions.

The term "cell cycle polypeptide" refers to one or more amino acid sequences, in glycosylated or non-glycosylated form, involved in the regulation of cell division. The term is also inclusive of fragments, variants, homologs, alleles or precursors (e.g., preproproteins or proproteins) thereof.

The term "splicing factor polypeptide" or "SF" refers to one or more splicing factor amino acid sequences involved in the regulation of splicing. The term "SR polypeptide" or "SR" refers to one or more amino acid sequences which are RNA-binding proteins containing repeating arginine and serine residues (SR proteins) and are implicated in constitutive and/or alternative splicing of pre-mRNA. SR proteins are involved in the selection and utilization of splice sites by spliceosomes; SF2/ASF-like polypeptides are a subset of SR proteins. An amino acid motif comprising SEQ ID NO. 31: SWQDLKD is characteristic of SF2/ASF-like polypeptides.

These terms are also inclusive of fragments, variants, splicing alternatives, homologs, alleles, glycosylated or precursors (e.g., preproproteins or proproteins) thereof.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive" includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all other analytes lacking the epitope which are present in the sample.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Generally hybridization is conducted for a time in the range of from four to sixteen hours.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "*Overview of principles of hybridization and the strategy of nucleic acid probe assays*", Elsevier, N.Y. (1993); and *Current Protocols in Molecular Biology*, Chapter 2, Ausubel et al., Eds., Greene Publishing and Wiley-Interscience, New York (1995).

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein "stable transformation" refers to the transfer of a nucleic acid fragment into a genome of a host organism (this includes both nuclear and organelle genomes) resulting in genetically stable inheritance. In addition to traditional methods, stable transformation includes the alteration of gene expression by any means including chimerplasty or transposon insertion.

As used herein "Transient Transformation" refers to the transfer of a nucleic acid fragment into the nucleus (or DNA-containing organelle) of a host organism resulting in gene expression without integration and stable inheritance.

As used herein "Modified cells" are cells that have been transformed. As used herein "Re-transformation" refers to the transformation of a modified cell.

As used herein, "vector" includes reference to a nucleic acid used in transfection of a host cell and into which can be inserted a polynucleotide. Vectors are often replicons. Expression vectors permit transcription of a nucleic acid inserted therein.

As used herein, "vivipary" refers to failure of the embryo to enter developmental arrest, causing precocious germination of the seed on the mother plant (McCarty et al., 1989).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG® programs, Accelrys, Inc., San Diego, Calif.); the CLUSTAL program is well described by Higgins and Sharp, Gene 73:237–244 (1988); Higgins and Sharp, CABIOS 5:151–153 (1989); Corpet et al., Nucleic Acids Research 16:10881–90 (1988); Huang et al., Computer Applications in the Biosciences 8:155–65 (1992), and Pearson et al., Methods in Molecular Biology 24:307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel et al., Eds., Greene Publishing and Wiley-Interscience, New York (1995).

As those of ordinary skill in the art will understand, BLAST searches assume that proteins can be modeled as random sequences. However, many real proteins comprise regions of nonrandom sequences that may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem. 17:149–163 (1993)) and XNU (Claverie and States, Comput. Chem. 17:191–201 (1993)) low-complexity filters can be employed alone or in combination.

(c) As used herein, "sequence identity" or "identity" in the context of two nucleic acid or polypeptide sequences includes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic Biol. Sci. 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. For purposes of defining the invention, % identity on the nucleic acid level is determined by the BESTFIT DNA Sequence Alignment software on Genescape using a gap weight of 50 and a length weight of 3. For purposes of defining the invention, % identity on the amino acid level is determined by the BESTFIT DNA Sequence Alignment software on Genescape using a gap weight of 12 and a length weight of 4.

(e) (i) The term "substantial identity" of polynucleotide sequences means that a polynucleotide comprises a sequence that has at least 70%, 80%, 90%, 91%, 92%, 93%, 94%, 95%, 96%, 97%, 98% or 99% or higher sequence identity to, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 85%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The term "substantial identity" in the context of a peptide indicates that a peptide comprises a sequence with at least 70%, 80%, 85%, 90%, 91%, 92%, 93%, 94%, 95%, 96%, 97%, 98% or 99% sequence identity to the reference sequence over a specified comparison window. Optimal alignment can be conducted using the homology alignment algorithm of Needleman and Wunsch, J. Mol. Biol. 48:443 (1970). Peptides which are "substantially similar" share sequences as noted above except that residue positions which are not identical may differ by conservative amino acid changes.

The present invention provides novel methods of using SR polypeptides and polynucleotides. Included are methods for increasing transformation frequencies, increasing crop yield, providing a positive growth advantage, modulating cell division, transiently modulating cell division, and for providing a means of identifying transformants.

The present invention provides novel nucleic acids encoding polypeptides having RNA binding activity. It further provides novel nucleic acids encoding polypeptides having RNA splicing activity.

The present invention provides novel nucleic acids encoding SF2/ASF-like genes zmSRp30, zmSRp31, and zmSRp32, and nucleic acids having substantial identity thereto. The present invention also provides polynucleotides complementary to zmSRp30, zmSRp31 and zmSRp32 and nucleic acids having substantial identity thereto.

The present invention further provides novel nucleic acids encoding SF2/ASF-like genes, zmSRp30, zmSRp31 and zmSRp32, and nucleic acids that hybridize thereto under stringent conditions.

Further provided are exonic and intronic sequences, promoters and untranslated sequence. Also provided are vectors, expression cassettes, transgenic host cells, transgenic plants, cells and transgenic seed comprising the polynucleotides and polypeptides of the invention. The present invention provides for methods of growing the plant cell to produce a regenerated, stably transformed plant. These plants and plant cells include corn, soybean, sorghum, sunflower, safflower, wheat, rice, alfalfa and oil-seed *Brassica*.

The present invention provides novel methods of affecting the splicing of a virus. It also provides novel methods of affecting the splicing of Geminiviral transcripts. The present invention further provides novel methods of affecting the splicing of Rep A. The present invention further provides novel methods of affecting the splicing of a virus such as wheat dwarf and maize streak virus. The present invention provides novel methods of increasing resistance to Geminivirus infection (Davies et al., "The Structure, Expression, Functions and Possible Exploitation of Geminivirus Genomes", Plant DNA Infectious Agents/edited by T. Hohn and J. Schell, Wien:Springer-Verlag 2:31–52 (1987).

The present invention provides novel polypeptides having RNA binding activity. It further provides novel polypeptides having RNA splicing activity. The present invention provides proteins that may involve modulation of gene expression in transgenic plants by a trans-splicing mechanism resulting in synthesis of different gene products from the same pre-mRNA transcripts.

This invention also provides proteins that may stimulate embryogenesis in recalcitrant plant material in order to increase the overall efficiency of transformation process.

The present invention provides novel methods of increasing transformation efficiency in a plant cell. A responsive target plant cell may be stably transformed with at least one SF2/ASF-like gene in a vector to produce a modified target cell. The modified target cell may be grown under conditions to produce at least one cell division to produce a progeny cell expressing the SF2/ASF-like polypeptide and then, optionally, the progeny cell is transformed with one or more vectors containing a polynucleotide of interest operably linked to a promoter. Also, a responsive target plant cell may be stably transformed with at least one SF2/ASF-like gene in a vector and a gene of interest to produce a modified target cell. The gene of interest may be in the same vector or in a separate vector. Alternatively, SF2/ASF-like protein or RNA may be introduced so as to increase transformation efficiency.

The present invention further provides novel methods of modulating splicing. The present invention provides novel methods for modulating gene expression, through modulation of splicing in plants. Methods for modulating SF2/ASF-like splicing proteins in response to environmental, developmental and other stimulus are provided.

In another aspect the invention provides a method for transiently modulating gene regulation of target cells comprising introducing into the target cells an isolated splicing polynucleotide, such as a ZmSR polynucleotide, in sense or antisense orientation operably linked to a promoter driving expression in the target cells, an isolated ZmSR polypeptide, or an antibody directed against a ZmSR polypeptide. ZmSR polynucleotides are envisioned to include ZmSRp30, 30', 31, 31', 32, 32' and 32".

In another aspect the invention provides a method for providing a means of identifying transformants comprising (a) introducing into a target cell an isolated polynucleotide operably linked to a promoter driving expression in the target cell or an isolated SF2/ASF-like polypeptide and (b) selecting for cells exhibiting positive growth advantage.

Further provided are methods of modulating splicing in a plant cell through introducing into a plant cell a SF2/ASF-like polynucleotide operably linked to a promoter to produce a transformed cell and growing the transformed cell to modulate splicing in the transformed cell compared to a corresponding non-transformed cell. The promoter may be an inducible, tissue-preferred promoter, an ear or tassel-preferred promoter.

The present invention provides for methods of modulating splicing in a plant cell wherein transgenes are spliced, the cell cycle is stimulated, or sex determination is affected. Further provided are methods where there is modulation of reproductive organ growth, vegetative plant growth, yield, apomixis, or flowering time.

The present invention provides for methods of modulating splicing in a plant cell increasing male sterility, abiotic stress tolerance, metabolic activity, photosynthesis, vegetative yield, pathogen resistance, or embryogenesis.

The present invention provides for methods of modulating splicing in a plant cell decreasing vivipary.

The present invention provides novel methods of identifying transformants by introducing into a cell a SF2/ASF-like polynucleotide operably linked to a promoter to produce a transformed cell and growing the transformed cell so as to increase embryogenesis in the transformed cell and provide a means of identifying transformants.

In addition to the positive influence of transient increases in transformation efficiency, stable expression would be a benefit for identifying transformants such as in positive selection schemes in the recovery of transgenic plants and plant cells. In a population of cells and/or callus growing in vitro, cells expressing an SF2/ASF-like gene, such as zmSRp30, zmSRp31 or zmSRp32, will provide differential growth advantage based simply on their accelerated embryogenesis. It would be expected that these transgenic cells or cell/clusters would grow more rapidly than their non-transformed counterparts in culture, permitting ready identification of transformants. Such a positive growth advantage (imparted by expression of a gene such as zmSRp30, zmSRp31 and zmSRp32), would also be beneficial in other types of transformation strategies, including as examples, protoplast transformation, leaf base transformation and transformation of cells in meristems. Such growth stimulation may also extend transformation protocols to tissues normally not amenable to culture.

The present invention provides, inter alia, compositions and methods for modulating (i.e., increasing or decreasing) the total levels of proteins of the present invention and/or altering their ratios in plants. Thus, the present invention provides utility in such exemplary applications as the regulation of gene expression, embryogenesis and differentiation through splicing. The polypeptides of the present invention can be expressed at times or in quantities that are not characteristic of non-recombinant plants or in recombinant plants without such regulation.

In particular, modulating splicing proteins is expected to provide a positive organ growth advantage and increase crop yield or alternatively, provide a negative growth advantage for use in, for example, a male sterility system.

The present invention also provides isolated nucleic acid comprising polynucleotides of sufficient length and complementarity to a splicing gene to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of splicing polypeptides, or for use as immunogens in the preparation and/or screening of antibodies. The isolated nucleic acids of the present invention can also be employed for use in sense or antisense suppression of one or more splicing genes in a host cell, tissue, or plant. Attachment of chemical agents that bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identify insertion sequence inactivated splicing genes from a cDNA library prepared from insertion sequence mutagenized plants. Progeny seed from the plants comprising the desired inactivated gene can be grown to a plant to study the phenotypic changes characteristic of that inactivation. See, Tools to Determine the Function of Genes, 1995 Proceedings of the Fiftieth Annual Corn and Sorghum Industry Research Conference, American Seed Trade Association, Washington, D.C., 1995.

Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention also provides isolated proteins comprising polypeptides including an amino acid sequence from the splicing polypeptides as disclosed herein. The present invention also provides proteins comprising at least one epitope from a splicing polypeptide. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of splicing polypeptides.

Methods are provided to express an SF2/ASF-like gene in a tissue-preferred manner. It is an object of this invention to affect ear development to increase yield. It is also an object of this invention to affect embryo development to increase embryo size, viability, transformability and performance. It is also an object of this invention to affect tassel development through modulation of SF2/ASF-like gene. Increasing tassel performance may improve pollen count, shed, viability or other fertility factors while decreasing tassel performance may lead to male sterility and provide another method of hybrid production.

This invention provides for a novel method of regulation of gene expression where expression is modulated at the RNA level. A foreign gene is introduced in plant cells by standard transformation methods. A strong, constitutive promoter such as the maize ubiquitin promoter for monocot plants and the 35SCaMV promoter for expression in dicots control the gene expression. The gene structure is modified to contain an intron, or other sequence, with mutated 5' and/or 3' splicing recognitions sites. These splicing sites are not optimally spliced by the cellular RNA splicing pathways, unless the SF2/ASF-like splicing factors, including those described in this application, are provided. The intron contains at least one stop codon, in frame with the preceding exonic coding sequences. The pre-mRNA molecules, although produced at high concentration, are not processed correctly leading to the synthesis of truncated, non-functional protein product. Therefore, the phenotype expected from the expressed transgene is not exhibited in these transgenic events. The alternative splicing factors, as exemplified by this application, can be introduced or co-introduced into those plants by genetic re-transformation, by sexual crossing or by introducing RNA or protein into the cell. The intron sequences will be removed from the pre-mRNA molecules in the re-transformed material, in plant cells wherein the polypeptide is present, or in the progeny of the sexual cross. Functional mRNA molecules will emerge that will be translated into a fully functional gene product.

SF2/ASF-like Genes

Regulation of foreign gene expression in transgenic plants is almost exclusively exercised at the level of transcription. A large number of promoter sequences have been isolated and characterized to provide a variety of options for the constitutive, inducible, temporal, or spatial regulation of gene expression. Such approach shares one basic feature—the expression of a foreign gene activated by the synthesis of RNA. In many instances, it has been difficult to obtain control of expression. For example, steroid inducible systems offer no background activity in the absence of an inducing factor, but relatively moderate expression level after induction. On the other hand, heat shock inducible promoters provide a strong activation at elevated temperatures, but they are quite "leaky" under normal physiological conditions.

RNA-binding proteins containing repeating arginine and serine residues (SR proteins) are implicated in constitutive and alternative splicing of pre-mRNA. A single pre-mRNA can be processed by alternative splicing to produce protein isoforms with different physiological functions. In one extreme case, it has been reported that over 30,000 alternatively spliced products of just one gene (the Dscam gene) can be expressed in *Drosophila* (Celotto, A. M. et al., Genetics (2001) 159:599–608). The process contributes to a diversity of gene products and regulation of gene expression as exemplified by sex determination in *Drosophila* (Lopez, A. J. et al., Annu. Rev. Genet. (1998) 32:279–305). Pre-mRNA splicing requires a number of factors organized into a functional entity of the spliceosome. The SR proteins are involved in the selection and utilization of splice sites by spliceosomes, most likely by interactions with exonic and intronic enhancer sequences (Hastings, M. L. et al., Curr. Opin. Cell Biol. (2001) 13:302–309).

Alternative splicing has been documented for numerous plant genes. Transcription factors regulating diverse biochemical pathways in plants are frequently found to produce alternatively spliced products such as transcripts of Vp-1 in wheat (McKibbin, R. S. et al., Proc. Natl. Acad. Sci. USA (2002) 99:10203–10208) (McKibbin et al., 2002), r1 gene in maize (Procissi et al, 2002), barley and maize MADS-box genes (Montag et al., 1995; Schmitz et al., 2000). The pathogen defense systems of tobacco, *Arabidopsis*, tomato, and flax rely on alternatively spliced Toll-like receptors for signaling pathogen-elicited response (Jordan et al., 2002). The systemic wound response pathway of tomato plants involves alternative splicing of prosystemin (Howe, 2001). The response to environmental factors such as light or salt concentration as well as the control of flowering time require SR-like splicing proteins or alternatively spliced gene products (Forment, J. et al., Plant J. (2002) 30:511–519); (Macknight, R. et al., Plant Cell (2002) 14:877–888); (Mano, S. et al., Plant J. (1999) 17:309–320).

Alternative splicing is also found in other splicing factor genes, including the polynucleotides of the invention. ZmSRp31 has a full length and truncated form and ZmSRp32 has at least three forms: two of which are truncated. ZmSRp30, ZmSRp31, and ZmSRp32 genes are the first maize SF2/ASF-like genes reported.

ZmSRp30, 31, and 32

The maize SF2/ASF-like RNA splicing factor genes, zmSRp30, zmSRp31 and zmSRp32 each have 2 RNA binding domains and one serine-arginine rich domain. The SF2/ASF-like genes have demonstrated splicing activity and the three polypeptide sequences are 66%–72% identical (77–81% conserved) to each other, Table 1. The first RNA binding domains (amino acids 8–94) of the three polypeptide sequences have 75–76 identical amino acids and 81–82 conserved amino acids out of the 87 amino acids, Table 2. The glycine hinge region between the two RNA binding domains (amino acids 95–103) is dissimilar among the three polypeptide sequences. The second RNA binding domains (104–178) of the three polypeptide sequences have 59–65 identical amino acids and 69–70 conserved amino acids out of the 75 amino acids, Table 3. The next domain, a serine-arginine rich domain (179–250) has 42/72 S/R residues in zmSRp30, 44/72 S/R residues in zmSRp31, and 45/72 in zmSRp32. In this S/R domain, 35–38 out of 72 amino acids residues are identical among the three sequences, Table 4. A PSK domain of approximately 30 amino acids is found at the carboxy terminus. A similar domain is also found in *Arabidopsis*, but not in mammalian splicing factors.

TABLE 1

Comparison of polypeptide sequences

|  | zmSRp30 | zmSRp31 | zmSRp32 |
|---|---|---|---|
| zmSRp30 |  | 72% (81%) | 66% (77%) |
| zmSRp31 | 72% (81%) |  | 67% (78%) |
| zmSRp32 | 66% (77%) | 67% (78%) |  |

The % identity is the first number in the box. The % conserved is the number in the parenthesis.

TABLE 2

Comparison of the first RNA binding domain, amino acids 8–94

|  | zmSRp30 | zmSRp31 | zmSRp32 |
|---|---|---|---|
| zmSRp30 |  | 76 (82) | 75 (81) |
| zmSRp31 | 76 (82) |  | 75 (82) |
| zmSRp32 | 75 (81) | 75 (82) |  |

The first number in the box is the number of identical amino acids. The second number is the number of conserved amino acids.

TABLE 3

Comparison of the second RNA binding domain, amino acids 104–178

|  | zmSRp30 | zmSRp31 | zmSRp32 |
|---|---|---|---|
| zmSRp30 |  | 65 (69) | 62 (70) |
| zmSRp31 | 65 (69) |  | 59 (69) |
| zmSRp32 | 62 (70) | 59 (69) |  |

The first number in the box is the number of identical amino acids. The second number is the number of conserved amino acids.

TABLE 4

Comparison of the S/R domain, amino acids 179–250

|  | zmSRp30 | zmSRp31 | zmSRp32 |
|---|---|---|---|
| zmSRp30 |  | 38 (45) | 37 (44) |
| zmSRp31 | 38 (45) |  | 35 (46) |
| zmSRp32 | 37 (44) | 35 (46) |  |

The first number in the box is the number of identical amino acids. The second number is the number of conserved amino acids.

In addition, zmSRp30, zmSRp31 and zmSRp32 are among the first monocots SRs reported. A putative pre-mRNA rice alternative splicing factor SF2 has been annotated in the NCBI protein database as Accession No. BAB90350. An *Arabidopsis* pre-mRNA splicing factor, SR1, has also been identified PNAS 92, (1995) 7672–7675; Lazar.

A comparison of the structural features of two maize SF2/ASF-like genes, zmSR31 and zmSR32 indicates a similar intron/exon architecture. Twelve introns had been identified for these particular cDNA clones in addition to one intron within the 5' untranslated region. The first eight exons encode for a highly conserved two RNA binding domains (RRM). Exons 5 and 6 contain the SEQ ID NO. 31: SWQDLKD motif considered to be a trademark of all SF2/ASF-like proteins. Exon 4 encodes for a glycine hinge connecting two RRM domains. This feature is less prominent in zmSRp31 and atSRp30. Exonic sequences are split by short introns in the two maize genes, thus producing an additional exon in maize genes. The three maize genes contain a long intron separating the exons of the SR domain. The maize SF2/ASF-like genes contain relatively long introns within the RRM domains. The zmSRp31 gene does not have a clear "glycine hinge" feature separating two RRM domains. Also, the phosphorylation domain at the 3' end seems not to be present in zmSRp31.

The maize genes are located on two different chromosomes: the zmSRp32 was found on chromosome 9, while the zmSRp31 is located on chromosome 6.

The two maize cDNA clones, zmSR32 and zmSR31, show strong homology to each other; 67% identical and 78% similar at the protein level based on the deduced protein sequence.

Among SR proteins, the subset of the human SF2/ASF-like proteins seems to play a unique role in the splicing reactions (Kawano, T. et al., Mech. Dev. (2000) 95:67–76). Knock-outs of the SF2/ASF-like genes in chicken, mouse, *Drosophila*, or *C. elegans* do not produce viable phenotypes (Jumaa, H. et al., Curr. Biol. (1999) 9:899–902). The results suggest that the expression of these genes is important for embryogenesis, organo- and morphogenesis (Longman, D. et al., EMBO J. (2000) 19:1625–1637). These reports further suggest that if SR splicing proteins are inactivated during embroygenesis, cells are viable but do not undergo differentiation. It is an object of this invention to express SR, either transiently, stably or to have SR protein present during transformation to modulate embryogenesis. Improving embryo formation may, among other effects, serve to increase cell viability and therefore increase transformation efficiency. Expression of SR also is suggested to play a role in organo- and morphogenesis (Longman, D. et al., EMBO J. (2000) 19:1625–1637). It is an object of this invention to modulate the expression of SR to affect organ development.

Plants

The isolated nucleic acids and methods of the present invention can be used over a broad range of plant types, including species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea,* and *Populus.*

Furthermore the isolated nucleic acids and method of the present invention can be used in monocots or dicots. They may also be used in grasses, cereals, cereal grasses (wheat, oat and corn) or oilseeds.

They can also be used in wheat, barley, oats, sorghum, rye, millet, rice, corn, sugar cane, coconut palm, canola, alfalfa, soybean, tobacco, cotton, potato or sunflower. Other plants of this invention include corn, soybeans, sorghum, sunflower, wheat, rice, alfalfa and canola. Types of corn included are field corn and corn useful for food, feed and fuel, sweet corn and popcorn. Field corn is a plant of this invention.

Nucleic Acids

The present invention provides, inter alia, isolated nucleic acids of RNA, DNA, and analogs and/or chimeras thereof, comprising a splicing factor polynucleotide.

A. Polynucleotides Encoding a Protein of SEQ ID NOS: 2, 4, 6, 8, 10, 12, 14, or Conservatively Modified or Polymorphic Variants Thereof The present invention provides isolated heterologous nucleic acids comprising a splicing factor polynucleotide, wherein the polynucleotide encodes a splicing factor polypeptide, disclosed herein in SEQ ID NOS: 2, 4, 6, 8, 10, 12, 14, or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides of SEQ ID NOS: 1, 3, 5, 7, 9, 11, 13, and silent variations of polynucleotides encoding a polypeptide of SEQ ID NOS: 2, 4, 6, 8, 10, 12, 14.

B. Polynucleotides Amplified from a *Zea mays* Nucleic Acid Library

As indicated in (b), supra, the present invention provides isolated nucleic acids comprising splicing factor polynucleotides, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.).

The nucleic acid library may be a cDNA library, a genomic library, or a library generally constructed from nuclear transcripts at any stage of intron processing. Generally, a cDNA nucleic acid library will be constructed to comprise a majority of full-length cDNAs. Often, cDNA libraries will be normalized to increase the representation of relatively rare cDNAs.

Total RNA Isolation: Libraries can be made from a variety of maize tissues but for optimal results one should isolate RNA's from actively growing cells. Full length cDNA libraries from such rapidly-dividing tissues (or cells at the G1/S boundary) would provide opportunities for identifying full length, splicing related cDNAs. Full length cDNA libraries can be constructed using the "Biotinylated CAP Trapper" method (Carninci, P., et al., Genomics 37:327–336, 1996) or the "mRNA Cap Retention Procedure" (Edery, I., et al., Molecular and Cellular Biology 15:3363–3371, 1995). Full length cDNA libraries can be normalized to provide a higher probability of sampling genes that express at low levels. Examples of cDNA library normalization methods are summarized by Bento Soares (Bonaldo, M. F., et al., Genome Research 6:791–806,1996).

Functional fragments of splicing protein can be identified using a variety of techniques such as restriction analysis, Southern analysis, primer extension analysis, and DNA sequence analysis. Function can also be determined by complementing yeast strains known to be mutant for splicing proteins with maize homologs. Primer extension analysis or S1 nuclease protection analysis, for example, can be used to localize the putative start site of transcription of the cloned gene. Ausubel at pages 4.8.1 to 4.8.5; Walmsley et al., "Quantitative and Qualitative Analysis of Exogenous Gene Expression by the S1 Nuclease Protection Assay," in *METHODS IN MOLECULAR BIOLOGY, VOL. 7: GENE TRANSFER AND EXPRESSION.*

The general approach of such functional analysis involves subcloning DNA fragments of a genomic clone, cDNA clone or synthesized gene sequence into an expression vector, introducing the expression vector into a heterologous host, and relying on an assay system such RNA binding, splicing activity or increased transformation efficiency to identify clones containing functional fragments and genes. Methods for generating fragments of a cDNA or genomic clone are well known. In addition, variants can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *DIRECTED MUTAGENESIS: A Practical approach*, (IRL Press, 1991). Thus, the present invention also encompasses DNA molecules comprising nucleotide sequences that have substantial sequence similarity with SEQ ID NO: 1, 3, 5, 7, 9, 11, 13 and encode zmSRp30, zmSRp30', zmSRp31, zmSRp31", zmSRp32, zmSRp32', and zmSRp32".

The present invention also provides subsequences of the nucleic acids. Any number of subsequences can be obtained by reference to SEQ ID NOS: 1, 3, 5, 7, 9, 11, or 13 and using primers which selectively amplify, under stringent conditions to: at least two sites to the polynucleotides of the present invention, or to two sites within the nucleic acid which flank and comprise a polynucleotide of the present invention, or to a site within a polynucleotide of the present invention and a site within the nucleic acid which comprises it. A variety of methods for obtaining 5' and/or 3' ends is well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego, 1990), pp. 28–38); see also, U.S. Pat. No. 5,470,722, and Current Protocols in Molecular Biology, Unit 15.6, Ausubel et al., Eds., Greene Publishing and Wiley-Interscience, New York (1995). Thus, the present invention provides splicing factor polynucleotides having the sequence of the splicing factor gene, nuclear transcript, cDNA, or complementary sequences and/or subsequences thereof.

Primer sequences can be obtained by reference to a contiguous subsequence of a polynucleotide of the present invention. Primers are chosen to selectively hybridize, under PCR amplification conditions, to a polynucleotide of the present invention in an amplification mixture comprising a genomic and/or cDNA library from the same species. Generally, the primers are complementary to a subsequence of the amplicon they yield. In some embodiments, the primers will be constructed to anneal at their 5' terminal end's to the codon encoding the carboxy or amino terminal amino acid residue (or the complements thereof of the polynucleotides of the present invention. The primer length in nucleotides is selected from the group of integers consisting of from at least 15 to 50. Thus, the primers can be at least 15, 18, 20, 25, 30, 40, or 50 nucleotides in length. A non-annealing sequence at the 5' end of the primer (a "tail") can be added, for example, to introduce a cloning site at the terminal ends of the amplicon.

The amplification primers may optionally be elongated in the 3' direction with additional contiguous nucleotides from the polynucleotide sequences, such as SEQ ID NOS: 1, 3, 5, 7, 9, 11, or 13 from which they are derived. The number of nucleotides by which the primers can be elongated is selected from the group of integers consisting of from at least 1 to 25. Thus, for example, the primers can be elongated with an additional 1, 5, 10, or 15 nucleotides. Those of skill will recognize that a lengthened primer sequence can be employed to increase specificity of binding (i.e., annealing) to a target sequence.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes that are specific to a polypeptide of the present invention. Methods for protein synthesis from PCR derived templates are known in the art and available commercially. See, e.g., Amersham Life Sciences, Inc., Catalog '97, p. 354.

C. Polynucleotides which Selectively Hybridize to a Polynucleotide of (A) or (B)

As indicated, supra, the present invention provides isolated nucleic acids comprising splicing factor polynucleotides, wherein the polynucleotides selectively hybridize, under selective hybridization conditions, to a polynucleotide of paragraphs (A) or (B) as discussed, supra. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated from a *Zea mays* nucleic acid library. Typically, the cDNA library comprises at least 80% full-length sequences, at least 85% or 90% full-length sequences, and at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having at Least 60% Sequence Identity with the Polynucleotides of (A), (B) or (C)

As indicated in (d), supra, the present invention provides isolated nucleic acids comprising splicing factor polynucleotides, wherein the polynucleotides have a specified identity at the nucleotide level to a polynucleotide as disclosed above in paragraphs (A), (B), or (C). The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 72%, 75%, 76%, 77%, 78%, 80%, 85%, 90%, 91%, 92%, 93%, 94%, 95%, 96%, 97%, 98% or 99%.

Optionally, the polynucleotides of this embodiment will share an epitope with a polypeptide encoded by the polynucleotides of (A), (B), or (C). Thus, these polynucleotides encode a first polypeptide that elicits production of antisera comprising antibodies that are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences that can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

Optionally, the polynucleotides of this embodiment will encode a protein having a specific activity at least 20%, 30%, 40%, or 50% of the native, endogenous (i.e., non-isolated), full-length splicing factor polypeptide. Further, the proteins encoded by polynucleotides of this embodiment will optionally have a substantially similar apparent dissociation constant ($K_m$) and/or catalytic activity (i.e., the microscopic rate constant, $k_{cat}$) as the native endogenous, full-length splicing factor protein. Those of skill in the art will recognize that $k_{cat}/K_m$ value determines the specificity for competing substrates and is often referred to as the specificity constant. Proteins of this embodiment can have a $k_{cat}/K_m$ value at least 10% of the non-isolated full-length splicing factor polypeptide as determined using the substrate of that polypeptide from the splicing specific pathways, supra. Optionally, the $k_{cat}/K_m$ value will be at least 20%, 30%, 40%, 50%, and at least 60%, 70%, 80%, 90%, or 95% the $k_{cat}/K_m$ value of the non-isolated, full-length splicing factor polypeptide. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

Optionally the polynucleotides of this invention will encode a protein having RNA binding activity and/or will encode a protein that modulates splicing activity.

E. Polynucleotides that are Subsequences of the Polynucleotides of (A)–(D)

As supra, the present invention provides isolated nucleic acids comprising splicing factor polynucleotides, wherein the polynucleotide comprises at least 15 contiguous bases from the polynucleotides of (A) through (D) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(D). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides. Optionally, the number of nucleotides in a subsequence is a percent of the designated coding sequence. For example, polynucleotides of the present invention are inclusive of polynucleotides comprising at least 50%, 60%, 70%, 80%, 90%, 93%, 95%, 97%, 98% or 99% of the coding nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype sequence, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequence compounds that bind, intercalate, cleave and/or crosslink to nucleic acids. Exemplary compounds include acridine, psoralen, phenanthroline, naphthoquinone, daunomycin or chloroethylaminoaryl conjugates.

Gene or Trait Stacking

In certain embodiments the nucleic acid sequences of the present invention can be combined with polynucleotide sequences of interest in order to create plants with a desired phenotype. For example, the polynucleotides of the present invention may be stacked with any other polynucleotides or with other useful genes. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) Eur. J. Biochem. 165:99–106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); increased digestibility (e.g., modified storage proteins (U.S application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) Gene 48:109); lectins (Van Damme et al. (1994) Plant Mol. Biol. 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837–5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. Sequences can have the same 5' and 3' splice sites or different ones. In certain cases, it may be desirable to introduce a transformation cassette that will suppress the expression of the polynucleotide of interest. This may be combined with any combination of other suppression cassettes or over-expression cassettes to generate the desired combination of traits in the plant. A further embodiment of this invention is to use the polynucleotides presented in DNA integration recombinase systems. For instance the polynucleoitdes of zmSRp30, zmSRp30', zmSRp31, zmSRp31', zmSRp32, zmSRp32', or zmSRp32" may be flanked with recombination sites such as FRT sites and/or Cre sites. See for example U.S. Pat. No. 6,187,994.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In some embodiments the monocot is *Zea mays* including *Zea mays* tissue from tassel and vegetative meristem.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is generally a vector, adapter, or linker for cloning and/or expression of a polynucleotide of the present invention. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript 11, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. For a description of various nucleic acids see, for example, Stratagene Cloning Systems, Catalogs 1995, 1996, 1997 (La Jolla, Calif.); and, Amersham Life Sciences, Inc., Catalog '97 (Arlington Heights, Ill.).

Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. While isolation of RNA and construction of cDNA and genomic libraries is well known to those of ordinary skill in the art, the following highlights some of the methods employed.

Synthetic Methods for Constructing Nucleic Acids

The isolated nucleic acids of the present invention can also be prepared by direct chemical synthesis by methods such as the phosphotriester method of Narang et al., Meth. Enzymol. 68:90–99 (1979); the phosphodiester method of Brown et al., Meth. Enzymol. 68:109–151 (1979); the diethylphosphoramidite method of Beaucage et al., Tetra. Lett. 22:1859–1862 (1981); the solid phase phosphoramidite triester method described by Beaucage and Caruthers, Tetra. Lefts. 22(20)1859–1862 (1981), e.g., using an automated synthesizer, e.g., as described in Needham-VanDevanter et al., Nucleic Acids Res., 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

Splicing vectors were constructed using standard molecular biology techniques. See, for example, Sambrook et al. (eds.) *MOLECULAR CLONING: a LABORATORY MANUAL*, Second Edition, (Cold Spring Harbor Laboratory Press, cold Spring Harbor, N.Y. 1989). Plasmids are based on pUC18. The vectors used in these experiments contain combinations of the same basic regulatory elements. The Omega prime (O') 5-prine sequence is described by Gallie et al., Nucl. Acids Res. 15:3257–3273 (1987). The selective marker gene, bar (Thompson et al., EMBO J. 6:2519–2523 (1987)), was used in conjunction with bialaphos selection to recover transformants. The Cauliflower Mosaic Virus 35S promoter with a duplicated enhancer region is described by Gardner et al., Nucl. Acid Res. 9:2871–2888 (1981). The 79 bp Tobacco Mosaic Virus leader is described by Gallie et al., Nucl. Acid. Res. 15:3257–3273 (1987) and was inserted downstream of the promoter followed by the first intron of the maize alcohol dehydrogenase gene ADH1-S. Described by Dennis et al., Nucl. Acid Res. 12:3983–3990 (1984). The 3' sequence pinII is described by An et al., Plant Cell 1:115–122 (1989).

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Promoters

A. Inducible Promoters

An inducible promoter can be operably linked to a nucleotide sequence encoding zmSRp30, zmSRp30', zmSRp31, zmSRp31', zmSRp32, zmSRp32', or zmSRp32". Optionally, the inducible promoter is operably linked to a nucleotide sequence encoding a signal sequence which is operably linked to a nucleotide sequence encoding zmSRp30, zmSRp30', zmSRp31, zmSRp31', zmSRp32, zmSRp32', or zmSRp32". With an inducible promoter the rate of transcription increases in response to an inducing agent.

Any inducible promoter can be used in the instant invention. See Ward et al. Plant Mol. Biol. 22:361–366 (1993). Exemplary inducible promoters include that from the ACE1 system which responds to copper (Mett et al., PNAS 90:4567–4571 (1993)); In2 gene from maize which responds to benzenesulfonamide herbicide safeners (Hershey et al., Mol. Gen. Genetics 227:229–237 (1991) and Gatz et al., Mol. Gen. Genetics 243:32–38 (1994)) or Tet repressor from Tn10 (Gatz et al., Mol. Gen. Genet. 227:229–237 (1991). An inducible promoter is a promoter that responds to an inducing agent to which plants do not normally respond. An exemplary inducible promoter is the inducible promoter from a steroid hormone gene the transcriptional activity of which is induced by a glucocorticosteroid hormone (Schena et al., Proc. Natl. Acad. Sci. U.S.A. 88:10421 (1991)) or the ecdysone inducible promoter (U.S. Pat. No. 6,504,082, issued Jan. 7, 2003).

The expression vector comprises an inducible promoter operably linked to a nucleotide sequence encoding zmSRp30, zmSRp30', zmSRp31, zmSRp31', zmSRp32, zmSRp32', or zmSRp32". The expression vector is introduced into plant cells and presumptively transformed cells are exposed to an inducer of the inducible promoter. The cells can be screened for the presence of encode zmSRp30, zmSRp30', zmSRp31, zmSRp31', zmSRp32, zmSRp32', or zmSRp32" protein by northern, RPA, or RT-PCR (using transgene specific probes/oligo pairs) BrdU or splicing assays, as described above.

B. Tissue-Preferred Promoters

A tissue-specific promoter can be operably linked to a nucleotide sequence encoding zmSRp30, zmSRp31', zmSRp31, zmSRp31', zmSRp32, zmSRp32', or zmSRp32" protein. Optionally, the tissue-preferred promoter is operably linked to a nucleotide sequence encoding a signal sequence which is operably linked to a nucleotide sequence encoding zmSRp30, zmSRp30', zmSRp31, zmSRp31', zmSRp32, zmSRp32', or zmSRp32". Plants transformed with a gene encoding zmSRp30, zmSRp30', zmSRp31, zmSRp31', zmSRp32, zmSRp32', or zmSRp32" operably linked to a tissue-preferred promoter produce the zmSRp30, zmSRp30', zmSRp31, zmSRp31', zmSRp32, zmSRp32', or zmSRp32" protein exclusively, or in a specific tissue.

Any tissue-preferred promoter can be utilized in the instant invention. Exemplary tissue-preferred promoters include a seed-preferred promoter such as that from the phaseolin gene (Murai et al., Science 23:476–482 (1983) and Sengupta-Gopalan et al., Proc. Natl. Acad. Sci. USA 82:3320–3324 (1985)), napin promoter, β-conglycinin promoter soybean lectin promoter, maize 15 kD zein promoter, 22 kD zein promoter, γ-zein promoter, waxy promoter, shrunken 1 promoter, globulin 1 promoter and shrunken 2 promoter (Thompson et al.; BioEssays; Vol. 10; p. 108; (1989); a leaf and light-induced promoter such as that from cab or rubisco (Simpson et al., EMBO J. 4(11):2723–2729 (1985) and Timko et al., Nature 318:579–582 (1985)); an anther-preferred promoter such as that from LAT52 (Twell et al., Mol. Gen. Genet. 217:240–245 (1989)); a pollen-preferred promoter such as that from Zm13 (Guerrero et al., Mol. Gen. Genet. 224:161–168 (1993)) or a microspore-preferred promoter such as that from apg (Twell et al., Sex. Plant Reprod. 6:217–224 (1993)).

The expression vector comprises a tissue-preferred promoter operably linked to a nucleotide sequence encoding a splicing factor protein. The expression vector is introduced into plant cells. The cells are screened for the presence of splicing factor protein by splicing assays, as described above. Tissue-preferred promoters may include male tissue-preferred promoters such as described in U.S. Pat. No. 6,452,069.

C. Constitutive Promoters

A constitutive promoter can be operably linked to a nucleotide sequence encoding a splicing factor protein or the constitutive promoter is operably linked to a nucleotide sequence encoding a signal sequence which is operably linked to a nucleotide sequence encoding splicing factor protein.

Many different constitutive promoters can be utilized in the instant invention. Exemplary constitutive promoters include the promoters from plant viruses such as the 35S promoter from CaMV (Odell et al., Nature 313:810–812 (1985)), Commelina yellow mottled virus (R. Torbert et al., Plant Cell Rep. 17:284–287 (1988)) and the promoters from such genes as rice actin (McElroy et al., Plant Cell 2:163–171 (1990)); ubiquitin (Christensen et al., Plant Mol. Biol. 12:619–632 (1989) and Christensen et al., Plant Mol. Biol. 18:675–689 (1992)); pEMU (Last et al., Theor. Appl. Genet. 81: 581–588 (1991)); MAS (Velten et al., EMBO J. 3:2723–2730 (1984)) and maize H3 histone (Lepetit et al., Mol. Gen. Genet. 231:276–285 (1992) and Atanassova et al., Plant Journal 2(3):291–300 (1992)).

The ALS promoter, a XbaI/NcoI fragment 5-prime to the Brassica napus ALS3 structural gene (or a nucleotide sequence that has substantial sequence similarity to the XbaI/NcoI fragment), represents a particularly useful constitutive promoter. (U.S. Pat. No. 5,659,026.

The expression vector comprises a constitutive promoter operably linked to a nucleotide sequence encoding splicing factor protein. The expression vector is introduced into plant cells and presumptively transformed cells are screened for the presence of splicing factor protein by splicing assays.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack (e.g. PR promoter), anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or in certain tissues, such as leaves, roots, fruit, seeds, or flowers. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter splicing content and/or composition in a desired tissue. Thus, in some embodiments, the nucleic acid construct will comprise a promoter functional in a plant cell, such as in Zea mays, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a splicing factor gene so as to control the expression of the gene. Gene expression can be modulated under conditions suitable for plant growth so as to alter splicing content and/or composition. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., The Maize Handbook, Chapters 114–115, Freeling and Walbot, Eds., Springer, N.Y. (1994); Corn and Corn Improvement, 3$^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D gel electrophoresis; DNA probe arrays; and isolation of proteins known to be expressed with some specificity in the target tissue. Such methods are well known to those of skill in the art. Commercially available products for identifying promoters are known in the art such as the Clontech (Palo Alto, Calif.) Universal GenomeWalker Kit.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, Mol. Cell Biol. 8:4395–4405 (1988); Callis et al., Genes Dev. 1:1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. In Enzymol. 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene 61:1–11 (1987) and Berger et al., Proc. Natl. Acad. Sci. USA 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to gene expression in plants. To accomplish this, a nucleic acid segment from the desired gene is cloned and operably linked to a promoter such that the anti-sense strand of RNA will be transcribed. The construct is then transformed into plants and the anti-sense strand of RNA is produced. In plant cells, it has been shown that antisense RNA inhibits gene expression by preventing the accumulation of mRNA which encodes the enzyme of interest, see, e.g., Sheehy et al., Proc. Nat'l. Acad. Sci. USA 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., The Plant Cell 2:279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., Nature 334: 585–591 (1988).

Proteins

The isolated proteins of the present invention comprise a polypeptide having at least 10 amino acids encoded by any one of the polynucleotides of the present invention as discussed more fully, supra, or polypeptides which are conservatively modified variants thereof. Exemplary polypeptide sequences are provided in SEQ ID NOS: 2, 4, 6, 8, 10, 12, and 14. The proteins of the present invention or variants thereof can comprise any number of contiguous amino acid residues from a polypeptide of the present invention, wherein that number is selected from the group of integers consisting of from 10 to the number of residues in a full-length splicing polypeptide. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, or 5.

As those of skill will appreciate, the present invention includes both binding and catalytically active polypeptides of the present invention. Catalytically active polypeptides have a specific activity at least 20%, 30%, or 40%, and at least 50%, 60%, or 70%, and at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention encoded by a polynucleotide of the present invention as described, supra. Exemplary polypeptides include those which are full-length, such as those disclosed in SEQ ID NOS: 2, 6, and 10. Further, the proteins of the present invention will not bind to antisera raised against a polypeptide of the present invention which has been fully immunosorbed with the same polypeptide. Immunoassays for determining binding are well known to those of skill in the art. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or plant cells. The cells produce the protein in a non-natural condition (e.g., in quantity, composition, location, and/or time), because they have been genetically altered through human intervention to do so. In eukaryotic cells overexpression of a non-functional fusion protein may be desirable. After isolation and purification of the fusion protein from the expressing cells, enzymatic cleavage could be used to restore function to the purified zmSRp30, zmSRp31, or zmSRp32 protein. In addition, fusions with zmSRp30, zmSRp31 or zmSRp32 can have application for affinity matrices and affinity columns used for purifying other splicing factor genes. For example, "His-patch" thioredoxin fusions can be expressed, and the isolate His-zmSRp31 or His-zmSRp32 fusion protein bound to metal chelate columns. Whole cell protein extracts can then be passed through the column to selectively trap proteins that interact with zmSRp30, zmSRp31 or zmSRp32. See Ausubel et al., 1990 for general methods. Similarly, glutathione-S transferase fusions can be used to attach proteins to solid-phase matrices for this type of affinity binding. This method has been used, for example, to identify splicing genes whose proteins bind to GST-Rb in L. Magnaghi-Jaulin et al., Retinoblastoma protein represses transcription by recruiting a histone deacetylase. Nature 391:601–604 (1998). It may also be advantageous to fuse additional functional genes to the zmSRp30, zmSRp30', zmSRp31, zmSRp31', zmSRp32, zmSRp32', or zmSRp32" gene. For example it would be useful to fuse a green fluorescent gene or some other reporter gene.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible) followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al., Gene 22:229–235 (1983); Mosbach et al., Nature 302:543–545 (1983)).

B. Expression in Eukaryotes

A variety of eukaryotic expression systems such as yeast, insect cell lines, plant and mammalian cells, are known to those of skill in the art. As explained briefly below, a of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein et al., Gene 8:17–24 (1979); Broach et al., Gene 8:121–133 (1979)).

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cell cultures. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., Immunol. Rev. 89:49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See Schneider, J. Embryol. Exp. Morphol. 27:353–365 (1987)).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., J. Virol. 45:773–781 (1983)). Additionally, gene sequences to control replication in the host cell may be incorporated into the vector such as those found in bovine papilloma virus type-vectors. Saveria-Campo, M., *Bovine Papilloma Virus DNA a Eukaryotic Cloning Vector in DNA Cloning* Vol. II a Practical Approach, D. M. Glover, Ed., IRL Press, Arlington, Va., pp. 213–238 (1985).

Transfection/Transformation/Introduction

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection or introduction of DNA, RNA or protein into a cell may be employed.

Gene Transformation Methods

A DNA sequence coding for the desired polynucleotide of the present invention, for example a cDNA or a genomic sequence encoding a full length protein or functional fragment will be used to construct a recombinant expression cassette which can be introduced into the desired plant.

Numerous methods for introducing foreign genes into plants are known and can be used to insert the splicing gene into a plant host, including biological and physical plant transformation protocols. See, for example, Miki et al., 1993, "Procedure for Introducing Foreign DNA into Plants," In: *Methods in Plant Molecular Biology and Biotechnology*, Glick and Thompson, eds., CRC Press, Inc., Boca Raton, pages 67–88. The methods chosen vary with the host plant, and include chemical transfection methods such as calcium phosphate, microorganism-mediated gene transfer such as *Agrobacterium* (Horsch et al., Science 227: 1229–31, 1985), electroporation, micro-injection, and biolistic bombardment.

The most widely utilized method for introducing an expression vector into plants is based on the use of *Agrobacterium*. The Ti and Ri plasmids of *A. tumefaciens* and *A. rhizogenes*, respectfully, carry genes responsible for genetic transformation of plants. See, for example, Kado, 1991, Crit. Rev. Plant Sci. 10:1. Descriptions of the *Agrobacterium* vector systems and methods for *Agrobacterium*-mediated gene transfer are provide in Gruber et al., supra; Miki et al., supra; and Moloney et al., 1989, Plant Cell Reports 8:238. Methods for *Agrobacterium*-mediated transformation in rice is disclosed in (Hiei et al., 1994, The Plant Journal 6:271–282) and maize (Ishida et al., 1996, Nature/Biotechnology 14:745–750). Methods for *Agrobacterium*-mediated transformation in sorghum are disclosed in WO 98/49332. Methods for *Agrobacterium*-mediated transformation in maize are disclosed in WO 98/32326. Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles (Sanford et al., 1987, Part. Sci. Technol. 5:27; Sanford, 1988, Trends Biotech 6:299; Sanford, 1990, Physiol. Plant 79:206; Klein et al., 1992, Biotechnology 10:268). Another method for physical delivery of DNA to plants is sonication of target cells as described in Zang et al., 1991, Bio/Technology 9:996. Alternatively, liposome or spheroplast fusions have been used to introduce expression vectors into plants. See, for example, Deshayes et al., 1985, EMBO J. 4:2731; and Christou et al., 1987, PNAS USA 84:3962. Direct uptake of DNA into protoplasts using $CaCl_2$ precipitation, polyvinyl alcohol or poly-L-ornithine have also been reported. See, for example, Hain et al., 1985, Mol. Gen. Genet. 199:161; and Draper et al., 1982, Plant Cell Physiol. 23:451.

Electroporation of protoplasts and whole cells and tissues has also been described. See, for example, Donn et al., 1990, In: *Abstracts of the VIIth Int'l Congress on Plant Cell and Tissue Culture (IAPTC)*, A2–38, page 53; D'Halluin et al., 1992, Plant Cell 4:1495–1505; and Spencer et al., 1994, Plant Mol. Biol. 24:51–61. Microinjection of DNA into whole plant cells has also been described as has microinjection into protoplasts. See, for example in whole cells, Neuhaus et al., 1987, Theor. Appl. Genet. 75:30–36; and in protoplasts, Crossway et al., 1986, Mol. Gen. Genet. 202: 179–185; and Reich et al., 1986, Biotechnology 4:1001–1004. Another useful basic transformation protocol involves a combination of wounding by particle bombardment, followed by use of *Agrobacterium* for DNA delivery, as described by Bidney et al., Plant Mol. Biol. 18:301–313 (1992). Useful plasmids for plant transformation include PHP9762. The binary backbone for PHP9762 is bin 19. See Bevan, Nucleic Acids Research 12:8711–8721 (1984).

DNA can also be introduced into plants by direct DNA transfer into pollen as described by Zhou et al., Methods in Enzymology 101:433 (1983); D. Hess, Intern Rev. Cytol. 107:367 (1987); Luo et al., Plane Mol. Biol. Reporter 6:165 (1988). Expression of polypeptide coding nucleic acids can be obtained by injection of the DNA into reproductive organs of a plant as described by Pena et al., Nature 325:274 (1987). Transformation can also be achieved through electroporation of foreign DNA into sperm cells then microinjecting the transformed sperm cells into isolated embryo sacs as described in U.S. Pat. No. 6,300,543 by Cass et al. DNA can also be injected directly into the cells of immature embryos and the rehydration of desiccated embryos as described by Neuhaus et al., Theor. Appl. Genet. 75:30 (1987); and Benbrook et al., in Proceedings Bio Expo 1986, Butterworth, Stoneham, Mass., pp. 27–54 (1986).

Expression cassettes and vectors and in vitro culture methods for plant cell or tissue transformation and regeneration of plants are known and available. See, for example, Gruber et al., 1993, *"Vectors for Plant Transformation"* In: *Methods in Plant Molecular Biology and Biotechnology*, Glick and Thompson, eds., CRC Press, Inc., Boca Raton, pages 89–119.

Once a single transformed plant has been obtained by the a recombinant DNA method, e.g., a plant transformed with a desired gene, conventional plant breeding methods can be used to transfer the structural gene and associated regulatory sequences via crossing and backcrossing. In general, such plant breeding techniques are used to transfer a desired gene into a specific crop plant. In the instant invention, such methods include the further steps of: (1) sexually crossing a transformed plant with a second non-transformed plant; (2) recovering embryos, seed or other gametogenic material from the cross; and (3) growing transgene-containing plants from the embryos, seed or gametogenic material.

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillilan Publishing Company, New York, pp. 124–176 (1983); and *Binding, Regeneration of Plants, Plant Protoplasts*, CRC Press, Boca Raton, pp. 21–73 (1985).

Methods for plant regeneration are known in the art and several methods are provided by Kamo et al., (Bot. Gaz. 146(3):324–334, 1985), West et al., (The Plant Cell 5:1361–1369,1993), and Duncan et al. (Planta 165:322–332, 1985).

The regeneration of plants containing the foreign gene introduced by *Agrobacterium* from leaf explants can be achieved as described by Horsch et al., Science 227:1229–1231 (1985). Transgenic plants of the present invention may be fertile or sterile.

Regeneration can also be obtained from plant callus, explants, organs, or parts thereof. Such regeneration techniques are described generally in Klee et al., Ann. Rev. of Plant Phys. 38:467–486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype, (e.g., altered splicing content or composition).

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

One embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Backcrossing to a parental plant and out-crossing with a non-transgenic plant are also contemplated.

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, *Solid-Phase Peptide Synthesis*, pp. 3–284 in *The Peptides: Analysis, Synthesis, Biology. Vol. 2: Special Methods in Peptide Synthesis, Part A*; Merrifield et al., J. Am. Chem. Soc. 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Modulating Splicing Factor Protein Content and/or Composition

The present invention further provides a method for modulating (i.e., increasing or decreasing) splicing factor protein content or composition in a plant or part thereof. Modulation can be effected by increasing or decreasing the splicing factor protein content (i.e., the total amount of splicing factor protein) and/or the splicing factor protein composition (the ratio of various splicing monomers in the plant) in a plant. The method comprises transforming a plant cell, transiently or stably, with a recombinant expression cassette comprising a polynucleotide of the present invention as described above to obtain a transformed plant cell. For stably transformed plant cells, growing the transformed plant cell under plant forming conditions, and inducing expression of a polynucleotide of the present invention in the plant for a time sufficient to modulate splicing factor protein content and/or composition in the plant or plant part.

In some embodiments, plant splicing or selective alternative splicing may be modulated by altering, in vivo or in vitro, the promoter of a non-isolated splicing factor gene to up- or down-regulate gene expression. In some embodiments, the coding regions of native splicing factor genes can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transformed into a plant cell. Subsequently, a plant cell comprising the promoter operably linked to a polynucleotide of the present invention is selected for by means known to those of skill in the art such as, but not limited to, Southern blot, gene expression analysis, DNA sequencing, or PCR analysis using primers specific to the promoter and to the gene and detecting amplicons produced there from. A plant or plant part altered or modified by the foregoing embodiments is grown under plant forming conditions for a time sufficient to modulate splicing protein content and/or composition in the plant. Plant forming conditions are well known in the art and discussed briefly, supra.

In general, content or composition is increased or decreased by at least 5%, 10%, 20%, 30%, 40%, 50%, 60%, 70%, 80%, 90%, 100%, 120%, 140%, 160%, 180%, 200%, 250%, 250%, 280%, or 300% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds that activate expression from these promoters are well known in the art. In other embodiments, splicing is modulated in monocots, particularly maize.

Molecular Markers

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, *The DNA Revolution* by Andrew H. Paterson 1996 (Chapter 2) in: *Genome Mapping in Plants* (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; i.e. single copy probes. Restriction fragments from homologous chromosomes are revealed. Differences in fragment size among alleles represent an RFLP. Thus, the present invention further provides a means to follow segregation of a splicing gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a splicing factor gene.

In the present invention, the nucleic acid probes employed for molecular marker mapping of plant nuclear genomes selectively hybridize, under selective hybridization conditions, to a gene encoding a polynucleotide of the present invention. In other embodiments, the probes are selected from polynucleotides of the present invention. Typically, these probes are cDNA probes or Pst I genomic clones. The length of the probes is discussed in greater detail, supra, but are typically at least 15 bases in length, or at least 20, 25, 30, 35, 40, or 50 bases in length. Generally, however, the probes are less than about 1 kilobase in length. Probes are single copy probes that hybridize to a unique locus in a haploid chromosome complement. Some exemplary restriction enzymes employed in RFLP mapping are EcoRI, EcoRv, and Sstl. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of the genomic DNA; (c) detecting there from a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In some embodiments, the nucleic acid probe comprises a polynucleotide of the present invention.

UTR's and Codon Preference

In general, translational efficiency has been found to be regulated by specific sequence elements in the 5' non-coding or untranslated region (5' UTR) of the RNA. Positive sequence motifs include translational initiation consensus sequences (Kozak, Nucleic Acids Res. 15:8125 (1987)) and the 5<G>7 methyl GpppG cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., Mol. and Cell. Biol. 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., Nucleic Acids Res. 12:387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Splice Sites

The recognition of exons and introns in plants is a complex process that is poorly defined. There are at least three sequence elements within introns that determine the intron identity. These include the 5' splice site also called the donor site, the 3' splice site referred to as the acceptor site, and the branch site. The most common plant exon/intron junction sites are AG/GUAAGU at the 5' splice site and GCAG/G at the 3' splice site. The branch point with a consensus sequence of CURAY is usually located about 30 bp from the 3' site and is separated form this site by a stretch of U-rich region. A number of splicing factors interact with specific elements of the intron sequences to form a functional complex called a spliceosome that is involved in recognition and processing of introns. In particular, the present invention describes three new plant splicing factors that recognize and define the intron splicing sites (Reddy, ASN, Critical Reviews in Plant Sciences (2001) 20:523–571). Under natural physiological conditions, the process is highly regulated. Mutations within the splicing sites prevent proper processing of the intron sequences (Lal, S, Choi J H, Curtis Hannah L (1999) Plant Physiol 120: 65–72; Lal et al. (1999) Plant Physiol 121:411–418). The present invention provides methods for controlling and regulating the splicing process by using splicing factors that are the subject of this invention.

Sequence Shuffling

The present invention provides methods for sequence shuffling using polynucleotides of the present invention, and compositions resulting there from. Sequence shuffling is described in PCT Publication No. WO96/19256. See also, Zhang, J. H., et al., Proc. Natl. Acad. Sci. USA 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an increased $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Detection of Nucleic Acids

The present invention further provides methods for detecting a polynucleotide of the present invention in a nucleic acid sample suspected of comprising a polynucleotide of the present invention, such as a plant cell lysate, particularly a lysate of corn. In some embodiments, a splicing gene or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-splicing genes that would yield a false positive result.

Detection of the hybridization complex can be achieved using any number of well-known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., Biotechniques 4(3):230–250 (1986); Haase et al., *Methods in Virology*, Vol. VII, pp. 189–226 (1984); Wilkinson, The theory and practice of in situ hybridization in: *In situ Hybridization*, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Assays for Compounds that Modulate Enzymatic Activity or Expression

The present invention also provides means for identifying compounds that bind to (e.g., substrates), and/or increase or decrease (i.e., modulate) the activity of active polypeptides of the present invention. The method comprises contacting a polypeptide of the present invention with a compound whose ability to bind to or modulate enzyme activity is to be determined. The polypeptide employed will have at least 20%, at least 30% or 40%, at least 50% or 60%, and at least 70% or 80% of the specific activity of the native, full-length splicing polypeptide (e.g., enzyme). Generally, the polypeptide will be present in a range sufficient to determine the effect of the compound, typically about 1 nM to 10 μM. Likewise, the compound will be present in a concentration of from about 1 nM to 10 μM. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics are well known in the art. See, e.g., Segel, *Biochemical Calculations*, $2^{nd}$ ed., John Wiley and Sons, New York (1976).

All references cited are herein incorporated by reference.

Although the present invention has been described in some detail by way of illustration and example for purposes of clarity of understanding, it will be obvious that certain changes and modifications may be practiced within the scope of the appended claims.

Identification and Isolation of Members of the SR Family of Pre-mRNA Splicing Factors in Maize Pioneer's cDNA (EST) database was screened for sequence homologies to the *Arabidopsis thaliana* SR1, a member of a serine-arginine-rich protein family of splicing factors. A cluster of 33 ESTs contained the sequence with homology to the second RNA binding domain, SR domain, and PSK domain of the SR1 cDNA. An EST was isolated from tassels of the maize A632 genotype and was subsequently used as a probe for screening a genomic BAC library established from the maize Mo17 genotype. Four overlapping BAC clones hybridizing with the probe within a common BamHI DNA fragment were identified. One clone was digested with BamHI according to the manufacturer conditions (Life Technologies, Grand Island, N.Y.) and the restriction fragments were sub-cloned into a modified standard cloning vector. E. coli carrying the BAC fragments was grown in Luria-Bertani (LB) medium (Sambrook et al., 1982) and plasmid DNA was extracted using QIAPREP SPIN MINIPREP KIT according to manufacturer's protocol (Qiagen Inc., Valencia, Calif., USA). DNA restriction fragments were resolved on agarose gels and transferred onto a nitrocellulose membrane using a Schleicher & Schuell turboblotting system (Schleicher & Schuell, Keene, N.H., USA). AlkPhos Direct labeling and detection kit was used for a probe labeling and hybridization according to the manufacturer's instructions (Amersham Pharmacia Biotech, Buckinghamshine, England). Four BamHI BAC restriction fragments were identified and sequenced. Since the BamHI fragments did not contain the extended promoter region of the gene, a similar procedure was repeated for the EcoRI restriction fragments of the clone DNA. The plasmid DNA preparations were probed with a promoter fragment generated by genomic PCR using the exon 1-specific primers using maize B73 genomic DNA as a template (Universal Genome Walker Kit, Clontech, Palo Alto, Calif., USA).

Another cluster of 25 cDNAs containing a full-length SR cDNA was isolated from the elongation zone within a stalk internode in the maize B73 genotype. Based on the sequence information, two primers were designed for genomic amplification of the corresponding coding sequence: CATC-CGTCGMGCTGCTCGACCTCGACTCMG (Seq ID 26) and GCATCAGAGMTMCMTAGCTGCATACTACAA (Seq ID 27). Genomic DNA was isolated from B73 leaves using the cetyltrimethyl-ammonium bromide (CTAB) method (Murray and Thompson, 1980). The Expand High Fidelity PCR system® (Roche Applied Science, Indianapolis, Ind., USA) was used to amplify the genomic fragment that was subsequently cloned into a vector and sequenced.

Alternative Products of the zmSRp32 Gene in Maize Cells

In *Arabidpsis*, the long intron 9 of atSRp34 is the site of alternative splicing that generates five protein isoforms from the same pre-mRNA. The alternative processing of the intron 10 of zmSRp32 was tested in maize B73 young leaves. A set of nested primers was designed to amplify the zmSRp32 mRNA message by RT-PCR. The pair of primers specific to the first exon and 3'-UTR amplified two visible PCR products indicating heterogeneity within a pool of the zmSRp32 messages. The same exon 1 primer was used together with two intron 10 specific antisense primers, I10a and I10b. While no amplification signal was produced by the exon 1/I10b primers, the exon 1/I10a primer set amplified about a 1.3 kb fragment. The RT-PCR product was recovered, cloned, and sequenced to indicate the presence of one additional exon, termed exon 11'. The exon 11' was flanked by the 5' AGAC and 3' AGGU splicing sites. The 5' splicing site was preceded by a U/A-rich sequence characteristic of plant introns. The 11' exon contains twelve additional codons in frame with the exon 10, which are followed by four stop codons. Premature termination of translation may produce truncated versions of zmSRp32. Two ESTs were found in a database containing the 11' exon sequences as predicted. One of them was isolated from a 4 day old embryo sac.

ZmSRp32 in Pre-mRNA Splicing Reactions in Maize Cells

Maize BMS cells under liquid culture conditions efficiently recognized and processed the ST-LS1 intron from potato (Vancanneyt, G. et al., Mol. Gen. Genet. (1990) 220:245–250) when integrated into the FLP recombinase coding sequence (See U.S. Pat. No. 5,929,301). The intron 5' and 3' splicing sites matched the sequence of the plant consensus-splicing site: AGGU. The same intron integrated into the gusA coding sequence was only partially processed when the 5' splicing site (a donor site) was modified from the AGGU consensus sequence to ACGU. The potato intron is an A/U-rich sequence characteristic of plant introns, however, the 3' end of this intron (around the 3' splicing site) is markedly missing the U/A motif. Nevertheless, overexpression of zmSRp32 in transiently transformed BMS cells provided complete splicing of the potato intron in the gusA gene.

In another experiment, vectors containing RepA with 5'/3' splicing junctions of CCGU/AGGA, AGGU/AGGU, CCGU/AGGU or AGGU/AGGA, or a control without an intron, were introduced into maize BMS cells along with expression cassettes containing zmSRp31, zmSRp32, or a control. The short 86 bp intron of the wheat dwarf virus (WDV) replication initiator protein (Rep) needs to be spliced in order for the virus to replicate in infected wheat or maize cells. Table 5 shows the results of the experiment. The results indicated a 50% splicing efficiency in maize BMS cells containing zmSRp31 along with the RepA with the 5' intron splicing site, CCGU, and the 3' splicing site, AGGA.

These results suggest, in this instance, that overexpression of zmSRp31 and zmSRp32 in BMS cells produces splicing enhancement when a weak splice site is present, in this case CCGU/AGGA and CCGU/AGGU. The experiment also shows that when the 5' splice site was not optimal the zmSRp31 and zmSRp32 genes increased splicing efficiency. Because the wheat dwarf virus needs spliced and non-spliced RepA to be fully infectious, modulating the splicing activity with zmSRp30, zmSRp31 or zmSRp32 implies a role in disease resistance.

TABLE 5

| | Splicing activity ratios-spliced to non-spliced | | | | |
|---|---|---|---|---|---|
| Expression of gene | Intronless | CCGU/ AGGA | AGGU/ AGGU | CCGU/ AGGU | AGGU/ AGGA |
| Control (without) | 1 | 0.2 | 0.65 | 0.25 | 0.45 |
| zmSRp31 | 1 | 0.5 | 0.67 | 0.3 | 0.49 |
| zmSRp32 | 1 | 0.4 | 0.5 | 0.46 | 0.48 |

Transformation, DNA Recovery, and GUS Staining

*Zea mays* Black Mexican Sweet (BMS) suspension cells were transformed by *Agrobacterium*-mediated transformation procedure as described in Zhao et al., 2002. Briefly, BMS cells (2 ml packed cell volume) and 2.5×10$^8$ *Agrobactenum* cells both in 5 ml of N6 medium (4 g/l N6 basal salts, 6.85% sucrose, 1.5 mg/l 2,4-D, 0.69 g/l L-proline, 0.5 mg/l thiamine-HCl, and 1× Eriksson's vitamin mix, pH 5.2) were mixed together and stirred on a gyratory shaker at 140 rpm for 3 hrs at 27° C. in the dark. Fifty μl samples of the BMS/*Agrobacterium* co-cultivation mixtures were placed on dry glass microfiber filters (VWR Scientific Products, 911 Commerce Court; Buffalo Grove, Ill. 60089), which were then transferred onto the N6 co-cultivation medium similar to the one used for the initial pre-incubations but containing 3% sucrose, 2 mg/l 2,4-D, pH 5.8, and supplemented with 0.3% agar. Plates were incubated in the dark at 27° C. for 24 hrs. Subsequently, filters were transferred onto the same media supplemented with 0.1 g/l carbenicilin. DNA was extracted from BMS cells harvested 3 days after co-cultivation using Qiagen's DNEASY PLANT MINI KIT according to the manufacturer's instructions (Qiagen Inc., Valencia, Calif., USA). DNA was eluted in 0.05 ml of water and its concentration was estimated with the PICOGREEN dsDNA quantitation kit (Molecular Probes, Eugene, Oreg.). PICOGREEN is a fluorescent nucleic acid stain for puantitatina double-stranded DNA. Total DNA (80 ng) was used to transform 40 µl of library-efficiency DH5α E.coli competent cells GIBCOBRL). Electroporation was done using the BIO-RAD Gene Pulser in 2 mm-wide cuvettes at 2.5 kV with capacitance set for 25 µF and resistance of 200 ohmes. Electroporated cells were incubated in 600 µls of 2×YT media at 37° C. for 30 mm. After incubation, 200 µl samples were dispensed onto plates containing LB medium supplemented with 0.1 g/l ampicilin. The plates were incubated overnight at 37° C. The number of recovered colonies per plate were averaged for each treatment. For GUS staining, three days old BMS cells still attached to the filters were transferred into Petri dishes containing 0.5 ml of X-Gluc solution (1.36 g $NaH_2PO_4$, 1.74 g $Na_2HPO4$, 164 mg $K_4Fe(CN)_6.3H_2O$, 211 mg $K_3Fe(CN)_6$, 0.06 ml Triton X-100, 50 mg X-Gluc, pH 7.0, final volume 100 ml) (Jefferson et al., 1987). After sealing with parafilm, the plates were incubated overnight at 37° C. in the dark.

RT-PCR

Three days after transformation BMS cells were collected, frozen in liquid nitrogen, and stored at −80 C until needed. The cells (100 mg) were homogenized in liquid nitrogen using mortar and pestle, and then RNA was extracted with the TRIzol reagent (Cat. No. 15596018) according to the manufacturer's instructions (Invitrogen Life Technologies, Carlsbad, Calif., USA). Usually about 5 to 7 ug RNA was extracted from 100 mg cells. RNA was dissolved in water by incubating for 10 min at 55° C. and 5 ul of DNaseI (Cat. No. 18068015, Invitrogen Life Technologies, Carlsbad, Calif., USA) was added to eliminate any DNA contamination. The incubation was for 2 hrs at room temperature. Fifty ng of RNA was used as a template to amplify the gusA intron region with the exon 1-specific primer GTCACTCATTACGGCAAAGTGTGGGTCAAT (Seq ID 15) and the exon 2-specific primer GCTTTTTCT-TGCCGTTTTCGTCGGTA (Seq ID 16). The Titan RT-PCR kit (Roche Applied Science, Indianapolis, Ind., USA) was used to carry out the RT-PCR reactions under the following conditions: 50° C. for 30 min, 94° C. for 2 min, 10 cycles at 94° C. for 10 sec, 60° C. for 30 sec, 68° C. for 1 min, and 25 cycles at 94° C. for 10 sec, 60° C. for 30 sec, 68° C. for 1 min (cycle elongation of 5 sec for each cycle). The products of the RT-PCR reaction were separated on 1% agarose gels. The same RNA extraction and RT-PCR protocol was used to isolate and amplify RNA form maize B73 leaf tissue. The zmSRp32 exon1-specific primer ATGAG-CAGGCGCTGGAGCCGCACGATCTA (Seq ID 17) was used in combination with the following primers: GCCAC-CAAAGCCACTTGAACGATCATG (exon 4) (Seq ID 18), GAAGAAGGCAGTCCAGTGACAAG (exon 5) (Seq ID 19), GAGAGAAATTATTGATGGATTTTCTG (intron 6b) (Seq ID 20), GAAAACCAAGCMCCGMTGAAATAAAC (intron 6a) (Seq ID 21), GACCTTGMCGAGMGAAACA-GATCTTG (exon 10) (Seq ID 22), GCTTTMCMCTTGGT-TCCAAAAGCCATGATG (intron 10a) (Seq ID 23), GACATTAGGTAAAATMTGGGACGATTTTAG (intron 10 b) (Seq ID 24), and GTTMGAAAAGMGAGCTCCT-GACTCCATC (3' UTR close to the stop codon) (Seq ID 25). The product of amplification with the primer pair exon1/intron 10a was sequenced.

Vector Construction

Although other vectors may be utilized, many of the Agro vectors described herewithin contain the pSB11 plasmid backbone integrated into the super-binary vector pSB1 residing in Agrobacterium strain LBA 4404 (Komari, T. et al., Methods of genetic transformation: Agrobacterium tumefaciens, In: Vasil IK (ed) Molecular Improvement of Cereal Crops, Kluwer Academic Publishers (1999) pp. 43–82). A zmSRp32 expression vector was constructed by insertion of the 1.3 kb SmaI/SnaBI restriction fragment containing zmSRp32 under control of the maize ubiquitin-1 promoter (Christensen, A. H. et al., Transgenic Res. (1996) 5:213–218) and the potato protease II terminator (An et al., 1989). A GUS expression vector contained GUS coding sequence with the ST-LS1 intron from potato (Vancanneyt, G. et al., Mol. Gen. Genet. (1990) 220:245–250) ligated in the same orientation and position as for the construction of zmSRp32. he pWI-11 vector was the source of the wheat dwarf virus (WDV) initiator protein gene (rep) (Ugaki, M. et al., Nucl. Acids Res. (1991) 19:371–377). A LIR:Rep-containing NheI/SphI fragment was subcloned into the corresponding restriction sites of a cloning vector and subsequently moved into the pSB11 plasmid backbone as an XbaI/PacI restriction fragment which was then open with BstEII in order to insert the BstEII fragment containing the zmSRp32 expression unit. This was then integrated into the Agrobacterium pSB1 plasmid.

EXAMPLE 1

Experiment to Show that zmSR Expression Enhances Transformation Efficiency

To demonstrate that zmSRp expression enhances transformation efficiency, a zmSR gene is cloned into a cassette with a constitutive promoter (i.e. either a strong maize promoter such as the ubiquitin (UBI) promoter including the first ubiquitin intron, or a weak constitutive promoter such as nos). Delivery of the zmSR gene in an appropriate plant expression cassette (for example, in a UBI::zmSRp31 or zmSRp32::pinII-containing plasmid) cotransformed with 35S::bar::pinII can be accomplished through numerous well-established methods for plant cells, including for example particle bombardment, sonication, PEG treatment or electroporation of protoplasts, electroporation of intact tissue, silica-fiber methods, microinjection or Agrobacterium-mediated transformation. Using one of the above methods, DNA is introduced into maize cells capable of growth on suitable maize culture medium. Such competent cells can be from maize suspension culture, callus culture on solid medium, freshly isolated immature embryos or meristem cells. Immature embryos of the Hi-II genotype may be used as the target for co-delivery of these two plasmids.

To assess the effect on transgene integration, growth of bialaphos-resistant colonies on selective medium is a reliable assay. Within 1–7 days after DNA introduction, the embryos are moved onto culture medium containing 3 mg/l of the selective agent bialaphos. Embryos, and later callus, are transferred to fresh selection plates every 2 weeks. After 6–8 weeks, transformed calli are recovered. Transgenic callus containing the introduced genes can be verified using PCR and Southern analysis. Northern analysis can also be used to verify which calli are expressing the bar gene, and whether the zmSR gene is being expressed at levels above normal wild-type cells (based on hybridization of probes to freshly isolated mRNA population from the cells). In immature embryos that have transient, elevated zmSR expression, higher numbers of stable transformants are recovered (likely a direct result of increased integration frequencies). Increased transgene integration frequency can also be assessed using such well-established labeling methods such as in situ hybridization providing an improved cellular/molecular environment for this event to occur.

EXAMPLE 2

Experiment to Show Over-expression of a Maize Alternative Splicing Factor in Wheat Increases Resistance to Pre-harvest Sprouting Vivipary is a physiological condition that leads to germination of embryos while attached to the cob. The viviparous-1 (Vp-1) gene appears necessary for the maturation phase of seed development. The gene encodes a transcription factor which pre-mRNA transcripts are frequently mis-spliced reducing the capacity to produce a full-length, functional proteins (McKibbin, R. S. et al., Proc. Natl. Acad. Sci. USA (2002) 99:10203–10208). This is particularly severe in hexaploid bread wheat and has a profound effect on the bread-making quality of wheat. Providing additional alternative splicing factor activity during embryo development and maturation may inhibit or prevent vivipary.

The maize alternative splicing factor gene, ZmSR, is cloned into a constitutive expression cassette (for example, UBI:ubi intron:ZmSRp32::pinII). Wheat immature embryos are transformed using particle bombardment with a 35S::bar::35S-containing plasmid; with or without co-bombardment of the ZmSR-containing plasmid. Embryogenic cultures are selected on 4 mg/l gluphosinate ammonium and plants regenerated following published methods (Rosco-Gaunt et al., 2001, incorporated by reference). Plants are grown to maturity and allowed to set seed. Ripe ears are harvested from plants from each treatment (ZmSR and control) at 14 weeks post-anthesis and are placed on moist paper towels on a free-draining surface in a mist propagator. For each ear, the number of nonsprouted and sprouted grains are scored after 7 days.

Another example of decreasing pre-harvest sprouting is to construct alternative splicing factor expression vectors with the zmSR expression vector designed for expression in the developing embryo. This vector contains the GLB1 (globin) promoter driving expression of a zmSR gene and a PinII terminator. In addition, the CAMV35S enhancer and promoter drive GAT expression and are excisable via FRT sites. GAT genes encode glyphosate N-acetyltransferase (GAT). See PCT publication WO02/36782 and U.S. application Ser. No. 10/427,692. The maize globulin-1 promoter is attached to the coding sequences of zmSR. This promoter assures strong and localized expression of the splicing factors in the developing embryos. The expression vectors are introduced into plant cells by transformation methods described in the previous examples. Transgenic plants are regenerated from selected calli (for example, by incorporating the bar gene into the expression vectors and growing callus on media containing 3 mg/l Bialaphos). Selected calli can be analyzed for the presence of new DNA sequences using commonly known methods. After self-pollination of T0 transgenic plants, the T1 embryos can be analyzed for the presence of alternatively spliced products of the Vp-1 gene by RT-PCR method. Western analysis using a polyclonal antibodies can be carried out to identify different isoforms of the Vp-1 protein. Embryos from transgenic plants showing the highest % of fully spliced Vp-1 transcripts are tested for homozygosity by the quantitative PCR method and germinated to produce T1 plants. The grain sprouting test can be performed on T2 seed generation by placing them on paper towels on a free-draining flat surface in an incubator with humidifier. The numbers of nonsprouted and sprouted grains can be scored after about 7 days.

EXAMPLE 3

Experiment to Show Over-expression of a Maize Alternative Splicing Factor in Wheat Increases Embryogenic Callus Frequency Wheat immature embryos are transformed using the method of Example 2 with an inducible promoter operably linked to a zmSR-containing coding sequence. A comparison between the mean callus scores (percentage of the surface area with embryogenic callus) of the control and of the ZmSR-bombarded scutellar tissues of wheat is predicted to show a significant improvement in the ZmSR-bombarded scutellar tissues over the control tissues. Furthermore, in examining the quality of embryogenic calli formed, the ZmSR-bombarded lines will show significant increases in the number of 'good' calli produced. The calli containing a zmSR-containing coding sequence would be expected to be generally larger, more rapidly growing and vigorous (i.e. calli with scores of 3 or 4).

The shoot regenerability of cultures can be correlated with the quality and quantity of somatic embryos produced in each callus. Shoot regenerability of zmSR-bombarded calli can be compared to the shoot regenerability of the control.

EXAMPLE 4 zmSR Genes in Positive Selection of Wheat Transformants

Transformation a cassette containing a zmSR gene is described in Example 2. "Good' rated calli are visually-selected on the basis of vigorous embryogenic growth and analyzed by PCR for the presence of the Ubi::zmSR::pinII transcription unit. Thus, transformed lines may be identified without selection. Typically, without chemical selection such transformed embryogenic calli cannot be recovered, except perhaps via positive selection for example with GFP.

When the zmSR gene is introduced, or co-introduced, into a plant cell without any additional selective marker, transgenic calli are identified by their ability to grow more rapidly than surrounding wild-type (non-transformed) tissues. Transgenic callus can be verified using PCR and Southern analysis. Northern analysis can also be used to verify which calli are expressing the maize SR gene at levels above normal wild-type cells (based on hybridization of probes to freshly isolated mRNA population from the cells).

The zmSR genes can also be, cloned into a cassette with an inducible promoter such as the benzenesulfonamide-inducible promoter. The expression vector is co-introduced into plant cells and after selection, as described above or on bialaphos, the transformed cells are exposed to the safener (inducer). This chemical induction of zmSR expression should result in increased embryogenesis and increased transformation efficiency. The cells are screened for the presence of the zmSR RNA by northern, or RT-PCR (using transgene specific probes/oligo pairs eg), for zmSR-encoded protein using zmSR-specific antibodies in Westerns or using hybridization. Likewise, other assays could be employed.

EXAMPLE 5

Control of Gene Expression Using Tissue-preferred or Cell-preferred Promoters

ZmSR gene expression using tissue-preferred or cell-preferred promoters modulates splicing in the corresponding tissues or cells. For example, using a seed-preferred promoter will stimulate cell division rate and result in increased seed biomass. Alternatively, driving zmSR expression with a strongly-expressed, early, tassel-preferred promoter will enhance development of this entire reproductive structure.

Expression of zmSR genes in other cell types and/or at different stages of development will similarly stimulate cell division rates. Similar to results observed in *Arabidopsis* (Doerner et al., 1996), root-preferred or root-preferred expression of zmSR is predicted to result in larger roots and faster growth (i.e. more biomass accumulation).

EXAMPLE 6

Modulating Flowering Time

Alternative splicing is involved in the control of flowering time. The *Arabidopsis* floral promoter FCA is alternatively spliced to produce at least four different transcripts. The accurate excision of all 21 introns is required to generate the gamma ($\gamma$) transcript, the only full-length transcript producing functional protein. There is less than 1% of transcript alpha ($\alpha$), 55% transcript beta ($\beta$), 35% transcript gamma ($\gamma$), and transcript delta ($\delta$) accounts for about 10% of the FCA mRNA in seedlings. Overexpression of the gamma ($\gamma$) transcript (provided as an FCA-gamma ($\gamma$) cDNA clone controlled by the 35S promoter) causes the plant to flower significantly earlier than the wild type (Macknight, R. et al., Plant Cell (2002) 14:877–888).

Overexpression of the alternative splicing factors zmSRp30, zmSRp31 and zmSRp32 of this invention can alter the relative abundance of the transcripts resulting in modulation of the flowering time. An expression vector containing zmSR under control of a strong plant promoter (such as the maize ubiquitin promoter) is introduced into plant cells by *Agrobacterium*-mediated transformation of immature embryos. Since it has been established that the alternative splicing factors act in a concentration-dependent manner, overexpression of such factors will increase processing of the pre-mRNAs synthesized from the endogenous FCA gene, in particular, it will lead to accumulation of a fully-spliced transcripts encoding the functional FCA protein.

To detect if alternative splicing of the FCA messages takes place in the transgenic cells, the reverse transcriptase-mediated polymerase chain reaction (RT-PCR) can be used to identify different FCA transcripts. These observations will be correlated with the evaluation of the flowering time under different environmental conditions (for example, plus/minus vernalization, long/short-day light exposures). Additional splicing of the FCA messages catalyzed by overexpressed alternative splicing factors will lead to earlier flowering of plants carrying the transgene.

Alternatively, an inducible promoter such as the benzenesulfonamide-inducible promoter can control the expression of the alternative splicing factor genes. The expression vector is co-introduced into plant cells and after selection transgenic plants are regenerated. At the time of desired flowering, the transgenic plants are exposed to the safener (inducer). This chemical induction of the alternative splicing factors expression should result in more fully-spliced floral promoter messages and earlier flowering.

EXAMPLE 7

A Method of Affecting Starch Composition

A type I starch-branching enzyme (SBEI) is able to produce three forms of SBEI gene transcripts by alternative splicing of the primary mRNA. This enzyme catalyzes the formation of amylopectin by introducing branch points into the linear amylose molecules. Thus, SBEs are important for the quality of starch synthesized in plants. Selective inhibition of different isoforms of starch branching enzyme has a profound effect on starch composition (Baga, M. et al., Plant Mol. Biol. (1999) 40:1019–1030; (Itoh, K. et al., Mol. Gen. Genet. (1997) 255:351–358). In rice, the Waxy gene encodes a granule-bound starch synthase (GBSS). All rice cultivars described as a low-amylose rice varieties use alternate splice sites in the GBSS pre-mRNA. They all have mutated sequence (AG$\underline{T}$TATA) at the putative leader intron 5' splice site of the GBSS gene (Frances, H. et al., Plant Mol. Biol. (1998) 38:407–415). This single-base mutation reduces the efficiency of CBSS pre-mRNA processing.

Overexpression of the alternative splicing factors described in this invention can alter the relative abundance of the SBEI and the GBSS transcripts resulting in the modification of the starch content. The expression unit containing the alternative splicing factors under control of an endosperm promoter, such as the maize gamma ($\gamma$) zein GZ promoter, can be introduced into plant cells by methods known to one of skill in the art.

The ZmSR expression vector designed for expression in the developing endosperm has Gamma Zein (GZ) promoter driving the zmSR gene and a GZUBI1ZM terminator. Also in the vector is the Ubi promoter (Christensen et al., Plant Mol. Biol. 12:619–632 (1989) and Christensen et al., Plant Mol. Biol. 18:675–689 (1992)) followed by GAT with a PinII terminator and flanked by FRT sites (2 on left and 1 on right).

Northern blot analysis of RNA isolated from transgenic events can be used to verify expression of the alternative splicing factors in the endosperm as well as provide evidence for an altered expression of the SBEI messages. The amylose content can be determined by potentiometric iodine titration and the starch content by gel permeation chromatography. Methods of detecting and analyzing relative abundance of transcripts are known to one of skill in the art and also include Northern, PCR and S1 protection.

EXAMPLE 8

Increasing Abiotic Stress Tolerance

Abiotic stress conditions such as drought and salinity strongly affect crop yields around the world. Pre-mRNA processing seems to be a general target of salt toxicity in eukaryotes (Forment, J. et al., Plant J. (2002) 30:511–519). In particular, members of a family of SR proteins are known to confer increased tolerance to salts in *Arabidopsis*. Two alternative splicing factors described in this patent application are members of the plant SR protein family. Transgenic plants, containing the alternative splicing factor genes, or just part of the coding sequences carrying the SR domain (complete or partial), can be obtained by genetic transformation using methods described elsewhere. Strong plant promoters, such as the cauliflower mosaic virus 35S promoter or the maize ubiquitin-1 promoter provide a relatively high level of protein expression from the introduced constructs. Primary transformation events (T0 plants) are regenerated from selected transgenic material and selfed to produce homozygous T1 plants. Transformation events are selected based on Southern blot analysis and quantitative PCR-based homozygosity tests. The level of protein expression (proteins containing the SR domain) is assessed by Northern blot analysis. Also, a transgene segregation ratio in the T1 generation can provide information on the transgene integration pattern.

Seeds/kernels from selected transgenic plants and untransformed controls are germinated in pots for about two-three weeks. After this initial period, the seedlings are watered with the 200 mM NaCl solution for the salt tolerance test. The salt treatment is continued until the salt-stress symptoms become evident on the control (untransformed) plants. A direct comparison between transgenic plants and salt-stressed control seedlings should identify the salt-tolerant phenotypes. Selected plants are allowed to grow and set seeds for similar tests in the T2 generation.

EXAMPLE 9

Excision of the zmSR Cassette

In cases where the zmSR gene has been stably integrated into a plant and expression is useful in the recovery of trangenics, but is ultimately not desired in the final product, the zmSR expression cassette (or any portion thereof that is flanked by appropriate FRT recombination sequences) can be excised using FLP-mediated recombination (see U.S. Pat. No. 5,929,301) or any other excision methods known to one of skill in the art. (See, for example, U.S. Pat. No. 6,187,994; Schlake and Bode (1994) Biochemistry 33:12746–12751; Huang et al. (1991) Nucleic Acids Research 19:443–448; Paul D. Sadowski (1995) In Progress in Nucleic Acid Research and Molecular Biology vol. 51, pp. 53–91; Michael M. Cox (1989) In *Mobile DNA*, Berg and Howe (eds) American Society of Microbiology, Washington D.C., pp. 116–670; Dixon et al. (1995) 18:449–458; Umlauf and Cox (1988) The EMBO Journal 7:1845–1852; Buchholz et al. (1996) *Nucleic Acids Research* 24:3118–3119; Kilby et al. (1993) Trends Genet. 9:413–421: Rossant and Geagy (1995) *Nat Med.* 1: 592–594; Albert et al. (1995) The Plant J. 7:649–659: Bayley et al. (1992) Plant Mol. Biol. 18:353–361; Odell et al. (1990) Mol. Gen. Genet. 223: 369–378; and Dale and Ow (1991) Proc. Natl. Acad. Sci. USA 88:10558–105620; all of which are herein incorporated by reference); Lox (Albert et al. (1995) *Plant J.* 7:649–659; Qui et al. (1994) Proc. Natl. Acad. Sci. USA 91:1706–1710; Stuurman et al. (1996) Plant Mol. Biol. 32:901–913; Odell et al. (1990) Mol. Gen. Genet. 223:369–378; Dale et al. (1990) Gene 91:79–85; and Bayley et al. (1992) Plant Mol. Biol. 18:353–361.).

EXAMPLE 10

The Effect of SR on Treatment of Co-delivered Transgenes

The plasmids listed in Table 6 below are used to evaluate the influence of SR on transient expression of co-delivered transgenes; the SuperMAS promoter is that described by Ni et al., 1996; sequence-specific interactions of wound-inducible nuclear factors with mannopine synthase 2' promoter wound responsive elements, Plant Mol. Biol. 30:77–96. The visible marker genes, GUS (b-glucoronidase; Jefferson R. A., Plant Mol. Biol. Rep. 5:387, 1987) and GFP (green fluorescent protein; Chalfie et al., Science 263:802, 1994) have been described, as has the maize-optimized GFP (GFPm; see U.S. Pat. No. 6,486,382). The Ubiquitin promoter has been described (Christensen et al., Plant Mol. Biol. 12:619–632 (1989) and Christensen et al., Plant Mol. Biol. 18:675–689 (1992), as have the pinII (An et al., 1989, Plant Cell 1:115–122) and 35S (Odell et al., 1985, Nature 313:810–812) 3' regions in these expression cassettes.

TABLE 6

Constructs used to evaluate the effect of SR expression on transient expression of co-delivered transgenes Plasmid Description SuperMAS::GUS::pinII 3' region
UBI::moPAT::CaMV35S 3' region
UBI::GFPm::pinII
WDV-LIR promoter::SR GFP Expression in Maize Transformation of the zmSR plasmid DNA into an inbred follows a well-established bombardment transformation protocol used for introducing DNA into the scutellum of immature maize embryos (Songstad, D. D. et al., In Vitro Cell Dev. Biol. Plant 32:179–183, 1996). It is noted that the any suitable method of transformation can be used, such as *Agrobacterium*-mediated transformation and many other methods. Cells are transformed by culturing maize immature embryos (approximately 1–1.5 mm in length) onto medium containing N6 salts, Erikkson's vitamins, 0.69 g/l proline, 2 mg/l 2,4-D and 3% sucrose. After 4–5 days of incubation in the dark at 28° C., embryos are removed from the first medium and cultured onto similar medium containing 12% sucrose. Embryos are allowed to acclimate to this medium for 3 h prior to transformation. The scutellar surface of the immature embryos is targeted using particle bombardment with either a UBI::GFPm::pinII plasmid+a UBI::maize-optimized PAT::pinII plasmid (control treatment) or with a combination of the UBI::GFPm::pinII plasmid+the zmSR plasmid. Embryos are transformed using the PDS-1000 Helium Gun from Bio-Rad at one shot per sample using 650PSI rupture disks. DNA delivered per shot averaged at 0.0667 ug. An equal number of embryos per ear are bombarded with either the control DNA mixture or the zmSR/GFP DNA mixture. Following bombardment, all embryos are maintained on standard maize culture medium (N6 salts, Erikkson's vitamins, 0.69 g/l proline, 2 mg/l 2,4-D, 3% sucrose) for 2–3 days and then evaluated for transient GFP expression.

In both experiments, we expect a greater number of cells transiently expressing GFP on the scutellar surface in the treatment containing the zmSR DNA when compared to the control.

Soybean

Tissue is excised from coyledons and placed on MS-based medium. A mixture of plasmid DNA, containing equal amounts of a SuperMas::GUS::pinII plasmid and the WDV-LIR::SR plasmid, is delivered into cells on the surface of the colyledon explants using particle-mediated delivery similar to that described for maize above. As a control, SuperMas::

GUS::pinII plasmid+UBI::moPAT::CaMV35S is introduced into the same target cells using an equal number of cotyledonary tissue pieces.

In the SR-treatment, greater numbers of transiently expressing cells would be expected on the cotyledon after GUS staining. In addition, for cells exhibiting transient gene expression, the level of expression as judged by relative intensity of histochemical staining would be expected to be greater in SR-treated tissues (as compared to controls).

EXAMPLE 11 zmSRp31 Increases Growth Rates in Early-developing Stable Maize Transformants

Transformation of the zmSR plasmid DNA into Hi-II follows the standard Hi-II bombardment transformation protocol (Songstad D. D. et al., In Vitro Cell Dev. Biol. Plant 32:179–183, 1996). Cells are transformed by culturing maize immature embryos (approximately 1–1.5 mm in length) onto 560P medium containing N6 salts, Erikkson's vitamins, 0.69 g/l proline, 2 mg/l 2,4-D and 3% sucrose. After 4–5 days of incubation in the dark at 28° C., embryos are removed from 560P medium and cultured, scutellum up, onto 560Y medium which is equivalent to 560P but contains 12% sucrose. Embryos are allowed to acclimate to this medium for 3 h prior to transformation. The scutellar surface of the immature embryos is targeted using particle bombardment with either a UBI::moPAT~GFPm::pinII plasmid or with a combination of the UBI::moPAT~GFPm::pinII plasmid+the GZ::zmSR::35S:GZ' plasmid. Embryos are transformed using the PDS-1000 Helium Gun from Bio-Rad at one shot per sample using 650PSI rupture disks. DNA delivered per shot averaged at 0.0667 ug. An equal number of embryos per ear are bombarded with either the control DNA (PAT~GFP) or the zmSRp31/PAT~GFP DNA mixture. Following bombardment, all embryos are maintained on 560L medium (N6 salts, Eriksson's vitamins, 0.5 mg/l thiamine, 20 g/l sucrose, 1 mg/l 2,4-D, 2.88 g/l proline, 2.0 g/l gelrite, and 8.5 mg/l silver nitrate). After 2–7 days post-bombardment, all the embryos from both treatments are transferred onto N6-based medium containing 3 mg/l bialaphos Pioneer 560P medium described supra, with no proline and with 3 mg/l bialaphos). Plates are maintained at 28° C. in the dark and are observed for colony recovery with transfers to fresh medium occurring every two weeks. Two weeks after DNA delivery, the newly-forming callus is examined using epifluorescence under the dissecting microscope (using commercially-available filter combinations for GFP excitation and emission).

At 2 weeks post-bombardment, numerous cells on the surface of the scutellar-derived tissue are expected to express GFP in the control treatment (no zmSRp31), but expressing foci consisted of single cell. No multicellular GFP-expressing clusters are expected in the control. At this same time-point, 2-weeks after DNA-delivery, the same sprinkling of single-celled GFP-expressing foci are expected on the surface of the tissue that had received the zmSR/PAT~GFP mixture. However, numerous macroscopic GFP-expressing multicellular clusters are also apparent. Many embryos are observed with multiple transgenic microcalli developing on the surface, with independent transformants beginning to grow from a single embryo.

After 3 weeks, GFP-expressing single cells will be observed in both treatments, although the frequency will decline. In the zmSR-treated embryos, the growth rate of the developing transgenic calli will continue to be very rapid. At 5 weeks post-bombardment, many zmSR colonies will continue to grow rapidly.

EXAMPLE 12

Experiment to Show how Transient zmSR Activity Enhances Transformation Frequency For transient zmSR-mediated cell cycle stimulation to increase transient integration frequencies, it may be desirable to reduce the likelihood of ectopic stable expression of the zmSR gene. Strategies for transient-only expression can be used. This includes delivery of RNA (transcribed from the zmSR gene), chemically end-modified DNA expression cassettes that typically will not integrate, or zmSR protein along with the transgene cassettes to be integrated to enhance transgene integration by transient stimulation of cell division. Using well-established methods to produce zmSR-RNA, this can then be purified and introduced into maize cells using physical methods such as microinjection, bombardment, electroporation or silica fiber methods. For protein delivery, the gene is first expressed in a bacterial or baculoviral system, the protein purified and then introduced into maize cells using physical methods such as microinjection, bombardment, electroporation or silica fiber methods.

Alternatively, zmSR proteins are delivered from *Agrobacterium tumefaciens* into plant cells in the form of fusions to *Agrobacterium* virulence proteins. Fusions are constructed between zmSR and bacterial virulence proteins such as VirE2, VirD2, or VirF which are known to be delivered directly into plant cells. Fusions are constructed to retain both those properties of bacterial virulence proteins required to mediate delivery into plant cells and the zmSR activity required for enhancing transgene integration. This method ensures a high frequency of simultaneous co-delivery of T-DNA and functional zmSR protein into the same host cell. The methods above represent various means of using the zmSR gene or its encoded product to transiently modulate gene expression through splicing, which in turn enhances transformation efficiency by providing an improved cellular/molecular environment for this event to occur (WO99/61619).

EXAMPLE 13

Experiment to Show how Re-transformation of SR-transgenic Progeny can Result in Elevated Transformation Frequency

*Agrobacterium* mediated transformation. As the starting point for *Agrobacterium*-mediated re-transformation experiments, regenerated inbred maize T0 transformants are produced containing maize SR expression cassettes and UBI::moPAT~GFP::pinII. The SR expression cassette with the nopaline synthase promoter from *Agrobacterium tumefaciens* (Shaw et al., Nucl. Acids Res. 12:7831–7846, 1984) or modified nos promoters is described below. The PAT~GFP cassette contains a maize-optimized gene encoding phosphinothricin acetyltransferase (moPAT, see WO 98/30701) followed by a sequence encoding 4x(GSSS), a flexible polypeptide linker of GLY-SER-SER-SER, and then a maize-optimized nucleic acid sequence encoding Green Fluorescence Protein (GFP; see WO 98/01575). This PAT~GFP fusion construct is driven by the maize ubiquitin promoter (Christensen et al., Plant Mol. Biol. 18:675–689, 1992) and contains a potato proteinase inhibitor II 3' sequence (An et al., Plant Cell 1:115–122, 1989).

Transgenic inbred maize plants containing a co-segregating SR expression cassette and the UBI::PAT~GFP expression cassette are crossed to wild-type (non-transformed) inbred maize plants (using the non-transformed parent as the pollen donor). As expected from such a cross, the developing embryos on these ears segregate either for transgene expression or wild-type. Immature embryos are harvested 12 days after pollination and transformed with an *Agrobacterium* binary plasmid containing UBI::moCAH::pinII (moCAH is a maize optimized [for codon usage] gene that encodes for the *Myrothecium verrucaria* cyanamide hydratase protein[CAH] that can hydrate cyanamide to non-toxic urea). A standard *Agrobacterium*-mediated transformation protocol (U.S. Pat. No. 5,981,840) adapted for cyanamide selection (see WO 98/30701) is used, with additional modifications listed below. *Agrobacterium* is grown to log phase in liquid minimal-A medium containing 100 μM acetosyringone and spectinomycin. Embryos are immersed in a log phase suspension of *Agrobacterium* adjusted to obtain 3×10$^8$ CFU's/ml. Embryos are then co-cultured on culture medium with acetosyringone for 3 days at 20° C. After 3 days the embryos are returned to standard culture medium with 100 mg/l carbenicillin added to kill residual *Agrobacterium*. After an additional 4 days the segregating embryos are divided into GFP positive and GFP negative populations and moved to fresh culture medium with 50 mg/l cyanamide for selection. After 8 weeks the numbers of transformed colonies are determined.

Since the PAT~GFP and SR expression cassettes are co-segregating, GFP expression is used to separate segregating transgenic (PAT~GFP+/SR+) and non-transgenic (wild-type) embryos after *Agrobacterium*-mediated transformation, and then these separate populations are cultured and selected as independent groups. Using embryos from three different ears co-segregating for GFP and SR, we expect the SR-containing embryos to exhibit a much higher transformation frequency demonstrating that ectopic SR expression improves re-transformation frequencies. For ears from which the wild-type embryos (non-transgenic segregants) produce very low levels (or no) transformants, we expect the GFP+/SR-containing embryos from the same ears to produce cyanamide-resistant transformants at approximately a 5–10% frequency. In ears in which the wild-type, non-transformed embryos produce higher levels of transformants (for example, upwards of 10%), we expect the transformation frequencies from the SR expressing embryos to be elevated to even greater levels, i.e. upwards of 30–40%.

Particle gun transformation re-transformations. As the starting point for particle gun-mediated re-transformation experiments, regenerated maize inbred T0 transformants are produced containing maize SR expression cassettes and UBI::moPAT~GFP::pinII. Transformants containing UBI::moPAT~GFP::pinII and SR expression cassettes are tested; with SR being driven by a nos promoter. As a control, a non-functional version of SR is used, in which the SR coding sequence is frame-shifted by 1 position after the START codon, resulting in essentially the same mRNA species but producing a non-functional protein. Expression of this frame-shifted sequence (abbreviated "f-shift" below) is driven by the nos promoter. As mentioned above for the functional SR genes, this f-shift SR cassette co-segregates with GFP in the T1 progeny embryos.

Transgenic maize inbred plants containing a co-segregating SR expression cassette and the UBI::PAT~GFP expression cassette are crossed to wild-type (non-transformed) PHP38 plants (using the non-transformed parent as the pollen donor). As expected from such a cross, the developing embryos on these ears segregate either for transgene expression or wild-type. Embryos co-segregating for GFP and SR (functional and frame-shift (fs) versions) are transformed using a particle gun using the standard PHP38 immature embryo bombardment transformation protocol (Songstad D. D. et al., In Vitro Cell Dev. Biol. Plant 32:179–183, 1996). Cells are transformed by culturing maize immature embryos (approximately 1–1.5 mm in length) onto 560P medium containing N6 salts, Erikkson's vitamins, 0.69 g/l proline, 2 mg/l 2,4-D and 3% sucrose. After 4–5 days of incubation in the dark at 28° C., embryos are removed from 560P medium and cultured, scutellum up, onto 560Y medium which is equivalent to 560P but contains 12% sucrose. Embryos are allowed to acclimate to this medium for 3 h prior to transformation. The scutellar surface of the immature embryos is targeted using particle bombardment with a ubi:moCAH:pinII plasmid. Embryos are transformed using the PDS-1000 Helium Gun from Bio-Rad at one shot per sample using 650 P.S.I. rupture disks. DNA delivered per shot averages at 0.1667 ug. Following bombardment, all embryos are maintained on 560L medium (N6 salts, Eriksson's vitamins, 0.5 mg/l thiamine, 20 g/l sucrose, 1 mg/l 2,4-D, 2.88 g/l proline, 2.0 g/l gelrite, and 8.5 mg/l silver nitrate). After 2–7 days post-bombardment, all the embryos from both treatments are transferred onto N6-based medium containing 50 mg/l cyanamide (560P medium described supra, with 50 mg/l cyanamide). Plates are maintained at 28° C. in the dark and are observed for colony recovery with transfers to fresh medium occurring every two to three weeks. Early in the sub-culture regime, GFP+ and GFP– embryos are separated. These two subpopulations are subsequently cultured and analyzed as separate treatments. The PAT~GFP expression cassette and the SR expression cassette co-segregate together, and thus the presence of GFP expression is used to separate SR+ and SR– progeny for analysis.

Comparing PAT~GFP+/SR+transgenic embryos with wild-type (non-transgenic) embryos from the same ear we expect will show that the overall recovery of cyanimide-resistant transformants is much higher for the SR transgenic embryos. For ears from PAT~GFP+/SRfs transgenic plants (containing the frame-shift control) we expect there to be no significant improvement in transformation frequencies over segregating wild-type embryos.

EXAMPLE 14

Using SR to Improve Soybean Transformation

Delivery of the SR gene can be accomplished through numerous well-established methods for plant cells, including for example particle bombardment, sonication, PEG treatment or electroporation of protoplasts, electroporation of intact tissue, silica-fiber methods, microinjection or *Agrobacterium*-mediated transformation. Using one of the above methods, DNA is introduced into soybean cells capable of growth on suitable soybean culture medium. The SR gene (zmSRp30, zmSRp31 or zmSRp32) is cloned into a cassette with a constitutive promoter (for example, the SCP-1 promoter which confers constitutive expression in soybean, see PHI Patent application WO 99/43838) and a 3' sequence such as the nos 3' region. Particle bombardment is used to introduce the SCP1::SR::nos-containing plasmid along with a SCP1::HYG::nos-containing plasmid (which, when expressed produces a protein which confers hygromycin resistance) into soybean cells capable of growth on suitable soybean culture medium. Such competent cells can be from soybean suspension culture, cell culture on solid medium, freshly isolated cotyledonary nodes or meristem cells. Suspension-cultured somatic embryos of Jack, a *Glycine max* (I.) Merrill cultivar, are used as the target for co-delivery of a SR and a HYG-expressing plasmid. For target tissues receiving the SR expression cassette, transformation frequency is improved. Media for induction of cell cultures with high somatic embryogenic morphology, for establishing suspensions, and for maintenance and regeneration of somatic embryos are described (Bailey M A, Boerma H R, Pyrrott W A, 1993 *Genotype effects on proliferative embryogenesis and plant regeneration of soybean, In Vitro Cell Dev Biol* 29P:102–108). Likewise, methods for particle-mediated transformation of soybean are well established in the literature, see for example Stewart N C, Adang M J, All J N, Boerma H R, Cardineau G, Tucker D, Pyrrott W A, 1996, Genetic transformation, recovery and characterization of fertile soybean transgenic for a synthetic *Bacillus thuringiensis* crylAc gene, Plant Physiol 112:121–129.

The invention claimed is:

1. An isolated nucleic acid encoding a polypeptide having RNA splicing activity comprising:
   (a) a polynucleotide that encodes a polypeptide of SEQ ID NOS: 10, 12, or 14;
   (b) a polynucleotide that encodes a polypeptide having at least 90% identity to SEQ ID NOS: 10, 12, or 14;
   (c) a polynucleotide comprising the sequence set forth in SEQ ID NO: 29.

2. A vector comprising at least one nucleic acid of claim 1.

3. A recombinant expression cassette comprising a nucleic acid of claim 1 operably linked to a promoter.

4. A host cell comprising the recombinant expression cassette of claim 3, wherein said host cell is a plant cell or a bacterial cell.

5. The host cell of claim 4 wherein said host cell is a plant cell.

6. The plant cell of claim 5 wherein said plant cell is a corn, soybean, sorghum, sunflower, safflower, wheat, rice, alfalfa, or *Brassica* cell.

7. A transgenic plant comprising at least one expression cassette of claim 3.

8. A transgenic seed from the plant of claim 7.

9. A transgenic plant produced by growing the seed of claim 8.

10. A method of increasing the splicing of a Geminivirus comprising introducing the isolated nucleic acid of claim 1 into a plant cell.

11. The method of claim 10 wherein the virus is a wheat dwarf or maize streak virus.

12. The method of claim 10 wherein Rep A splicing is increased.

13. An isolated ribonucleic acid sequence encoded by a polynucleotide of claim 1.

* * * * *

SEQUENCE LISTING

<160> NUMBER OF SEQ ID NOS: 30

<210> SEQ ID NO 1
<211> LENGTH: 1239
<212> TYPE: DNA
<213> ORGANISM: Zea Mays

<400> SEQUENCE: 1

```
aaacatagaa gccttgatgc atgattgaat acgaaaacaa tgagcaggcg caacagccgt      60
accatctatg taggcaatct ccctggggac atccgtgaga gggaggttga ggatctcttc     120
tacaagtatg gccgtatttt ggatattgac ttgaaaatac ctccgagacc tcctggatac     180
gcattcgttg agtttgagga tccacgtgat gctgatgatg caatttatgg ccgtgatggg     240
tataactttg atggctacag gttgagggtt gaattagctc atggtggcag aggccagtct     300
tattcttatg atcgttcaag cagctatagc agtgcatgcc gtggaggtgt ttctaggcgc     360
tctgatttcc gtgttatggt cactggttta ccctcatcgg catcgtggca agatctgaag     420
gaccacatgc ggcgcgctgg tgatgtctgt ttctctgatg tataccgtga ggctggagaa     480
actattggaa ttgtggatta tacaaattat gacgatatga aatacgcgat taggaagctt     540
gatgactcac agttcaggaa tgcattttca agagcatata tcagggtgag ggagtatgat     600
gctagatcac gaagcagaag ccgtagccac tcgtactcta gaagcccag ctacagcagg     660 agcaggagtc caaaatctgt ttctcagtca ccctcatctg tggatgaaag atcgctatca     720
agatctcgat ccccaatttc ttctccttct catgcaagat atgcgacaag ccctaggagc     780
agaagcgcat cccgttctcg gtctcctgtg agatccgatt gaactttgag agcccttgaa     840
gcagtgagca gccccaggga gaagaaagga acttgagagt atgccgtgcc atcacaatgg     900
tccgagtgat tatgctgttg ccactgctcc ctcacattta agaggttcc tcttatttag     960 acggcgcatt taattaacat tatcttgcta agagagact tatgcgtagt ctacttgtgt    1020
actcgttcgt ttgtcctcat gttcttggct tcaggaactc tggttttta tcattgtacc    1080 catagtaaaa cctagatgta gttggggtat gccgtatgcg tctatattcg gttggtcgaa    1140
tgtaaatctg gatgcatata tgcatctgtt tggtttcatt taggcctttc cttggtttcg    1200
tgattaatga caacataagc ttattgctgt gatcaaaaa                           1239
```

<210> SEQ ID NO 2
<211> LENGTH: 260
<212> TYPE: PRT
<213> ORGANISM: Zea mays

<400> SEQUENCE: 2

```
Met Ser Arg Arg Asn Ser Arg Thr Ile Tyr Val Gly Asn Leu Pro Gly
 1               5                  10                  15
```

```
Asp Ile Arg Glu Arg Glu Val Glu Asp Leu Phe Tyr Lys Tyr Gly Arg
            20                  25                  30

Ile Leu Asp Ile Asp Leu Lys Ile Pro Pro Arg Pro Pro Gly Tyr Ala
            35                  40                  45

Phe Val Glu Phe Glu Asp Pro Arg Asp Ala Asp Asp Ala Ile Tyr Gly
            50                  55                  60

Arg Asp Gly Tyr Asn Phe Asp Gly Tyr Arg Leu Arg Val Glu Leu Ala
65                  70                  75                  80

His Gly Gly Arg Gly Gln Ser Tyr Ser Tyr Asp Arg Ser Ser Ser Tyr
                    85                  90                  95

Ser Ser Ala Cys Arg Gly Gly Val Ser Arg Arg Ser Asp Phe Arg Val
            100                 105                 110

Met Val Thr Gly Leu Pro Ser Ser Ala Ser Trp Gln Asp Leu Lys Asp
            115                 120                 125

His Met Arg Arg Ala Gly Asp Val Cys Phe Ser Asp Val Tyr Arg Glu
            130                 135                 140

Ala Gly Glu Thr Ile Gly Ile Val Asp Tyr Thr Asn Tyr Asp Asp Met
145                 150                 155                 160

Lys Tyr Ala Ile Arg Lys Leu Asp Asp Ser Gln Phe Arg Asn Ala Phe
                    165                 170                 175

Ser Arg Ala Tyr Ile Arg Val Arg Glu Tyr Asp Ala Arg Ser Arg Ser
            180                 185                 190

Arg Ser Arg Ser His Ser Tyr Ser Arg Ser Pro Ser Tyr Ser Arg Ser
            195                 200                 205

Arg Ser Pro Lys Ser Val Ser Gln Ser Pro Ser Ser Val Asp Glu Arg
            210                 215                 220

Ser Leu Ser Arg Ser Arg Ser Pro Ile Ser Ser Pro Ser His Ala Arg
225                 230                 235                 240

Tyr Ala Thr Ser Pro Arg Ser Arg Ser Ala Ser Arg Ser Arg Ser Pro
                    245                 250                 255

Val Arg Ser Asp
            260

<210> SEQ ID NO 3
<211> LENGTH: 1427
<212> TYPE: DNA
<213> ORGANISM: Zea mays

<400> SEQUENCE: 3
aaacatagaa gccttgatgc atgattgaat acgaaaacaa tgagcaggcg caacagccgt     60
accatctatg taggcaatct ccctggggac atccgtgaga gggaggttga ggatctcttc    120
tacaagtatg gccgtatttt ggatattgac ttgaaaatac ctccgagacc tcctggatac    180
gcattcgttg agtttgagga tccacgtgat gctgatgatg caatttatgg ccgtgatggg    240
tataactttg atggctacag gttgagggtt gaattagctc atggtggcag aggccagtct    300
tattcttatg atcgttcaag cagctatagc agtgcatgcc gtggaggtgt ttctaggcgc    360
tctgatttcc gtgttatggt cactggttta ccctcatcgg catcgtggca agatctgaag    420
gaccacatgc ggcgcgctgg tgatgtctgt ttctctgatg tataccgtga ggctggagaa    480
actattggaa ttgtggatta tacaaattat gacgatatga aatacgcgat taggaagctt    540
gatgactcac agttcaggaa tgcatttttca agagcatata tcagggtgag ggagtatgat    600
gctagatcac gaagcagaag ccgtagccac tcgtactcta gaagcccag ctacagcagg    660
```

```
agcaggagtc caaaatctgt ttctcagtca ccctcatctg tggatgaaag gtttgctttt      720
gttttcccta gatttggcca tgcggcgatc tgggggctgc attgatataa tactggatgt      780
tttgagaatc ggagtggatg gtttgggact tcggatagta gagatggatt gtgatgcatg      840
tatgacaagt gggctacaat cagtcctagg agcaagatag gctgacaatc gctatcaaga      900
tctcgatccc caatttcttc tccttctcat gcaagatatg cgacaagccc taggagcaga      960
agcgcatccc gttctcggtc tcctgtgaga tccgattgaa ctttgagagc ccttgaagca     1020
gtgagcagcc ccagggagaa gaaaggaact tgagagtatg ccgtgccatc acaatggtcc     1080
gagtgattat gctgttgcca ctgctccctc acatttaaga ggtttcctct tatttagacg     1140
gcgcatttaa ttaacattat cttgctaaag agagacttat gcgtagtcta cttgtgtact     1200
cgttcgtttg tcctcatgtt cttggcttca ggaactctgg ttttttatca ttgtacccat     1260
agtaaaacct agatgtagtt ggggtatgcc gtatgcgtct atattcggtt ggtcgaatgt     1320
aaatctggat gcatatatgc atctgtttgg tttcatttag gcctttcctt ggtttcgtga     1380
ttaatgacaa cataagctta ttgctgtgat caaaaaaaaa aaaaaaa                   1427
```

<210> SEQ ID NO 4
<211> LENGTH: 241
<212> TYPE: PRT
<213> ORGANISM: Zea mays

<400> SEQUENCE: 4

```
Met Ser Arg Arg Asn Ser Arg Thr Ile Tyr Val Gly Asn Leu Pro Gly
 1               5                  10                  15

Asp Ile Arg Glu Arg Glu Val Glu Asp Leu Phe Tyr Lys Tyr Gly Arg
            20                  25                  30

Ile Leu Asp Ile Asp Leu Lys Ile Pro Pro Arg Pro Pro Gly Tyr Ala
        35                  40                  45

Phe Val Glu Phe Glu Asp Pro Arg Asp Ala Asp Ala Ile Tyr Gly
    50                  55                  60

Arg Asp Gly Tyr Asn Phe Asp Gly Tyr Arg Leu Arg Val Glu Leu Ala
65                  70                  75                  80

His Gly Gly Arg Gly Gln Ser Tyr Ser Tyr Asp Arg Ser Ser Tyr
                85                  90                  95

Ser Ser Ala Cys Arg Gly Val Ser Arg Ser Asp Phe Arg Val
            100                 105                 110

Met Val Thr Gly Leu Pro Ser Ser Ala Ser Trp Gln Asp Leu Lys Asp
        115                 120                 125

His Met Arg Arg Ala Gly Asp Val Cys Phe Ser Asp Val Tyr Arg Glu
    130                 135                 140

Ala Gly Glu Thr Ile Gly Ile Val Asp Tyr Thr Asn Tyr Asp Asp Met
145                 150                 155                 160

Lys Tyr Ala Ile Arg Lys Leu Asp Asp Ser Gln Phe Arg Asn Ala Phe
                165                 170                 175

Ser Arg Ala Tyr Ile Arg Val Arg Glu Tyr Asp Ala Arg Ser Arg Ser
            180                 185                 190

Arg Ser Arg Ser His Ser Tyr Ser Arg Ser Pro Ser Tyr Ser Arg Ser
        195                 200                 205

Arg Ser Pro Lys Ser Val Ser Gln Ser Pro Ser Val Asp Glu Arg
    210                 215                 220

Phe Ala Phe Val Phe Pro Arg Phe Gly His Ala Ala Ile Trp Gly Leu
225                 230                 235                 240
```

His

<210> SEQ ID NO 5
<211> LENGTH: 1203
<212> TYPE: DNA
<213> ORGANISM: Zea mays

<400> SEQUENCE: 5

| | | | | | |
|---|---|---|---|---|---|
| cacgccggca | tccgtcgaag | ctgctcgacc | tcgactcaag | ccttccttgc | tccttgccgc | 60 |
| cgtcgagtcg | tcgcaggaac | gatgacccgg | cggaacggct | gtacgatcta | cgtgggcaac | 120 |
| ctccccggcg | acatccgcga | gagggaagtg | gatgatctct | tctacaagta | tggacgtata | 180 |
| gtggaaattg | acttgaaaat | tccaccaagg | cctcctggtt | ttgcttttgt | tgagtttgag | 240 |
| gacgcacgtg | atgctgaaga | tgcaatatat | ggccgtgatg | gatacaactt | tgatggccat | 300 |
| aggttgcggg | tggaattagc | ccatggtgga | cgaggcacat | cttcttttga | tcgatctagc | 360 |
| agctatagca | gtgctggaca | acgcggtgcc | tcaaaacgtt | ctgattaccg | tgttatggtt | 420 |
| actggattac | cttcttcagc | atcatggcaa | gatctcaagg | accatatgcg | gcgagctggt | 480 |
| gatgtctgtt | tcactgatgt | gtatcgtgag | gctggagcaa | ctattggaat | agctgattat | 540 |
| actaactatg | aagatatgaa | acacgcgata | aggaagctag | atgattctga | gttccgtaat | 600 |
| gcttttcaa | ggacatatgt | ccgggtgagg | gagtatgatg | ctaggcgcag | ccgttctcgc | 660 |
| tccagaggca | gaaaccgctc | taagtcaaga | agcagaagcc | acagccactc | gtactcaaga | 720 |
| agcagaagct | gcagttatag | caagagtagg | agcccaagat | ctagatctgc | ttcagagtca | 780 |
| aaatcacctg | ttaaggcaag | atcaccatcc | agatcccctc | ctgtttctcc | ccggcgtgac | 840 |
| aagtctgcaa | gcaggagtcc | tgccaggagc | aagagtctgc | cccgatcttg | ttctccggca | 900 |
| aaatcagagt | gaatcggatt | ctgcacttga | aacgttcaga | aaggcagagc | tcgagctaaa | 960 |
| agattgctgt | acggattatg | agcactgtgc | tagtagcatt | gctgtccctt | ccatattttt | 1020 |
| acaaatactc | tgttctttga | ggagatcact | gtatgctact | actctgtacc | tgacgatgca | 1080 |
| aacgttgttg | gtttttgaac | ttagcagaac | gatgactttg | atcagctcca | tccattcctt | 1140 |
| ccatttttt | tttctgaata | tttcaaaaga | ttgtagtatg | cagctattgt | tattctctga | 1200 |
| tgc | | | | | | 1203 |

<210> SEQ ID NO 6
<211> LENGTH: 276
<212> TYPE: PRT
<213> ORGANISM: Zea mays

<400> SEQUENCE: 6

Met Thr Arg Arg Asn Gly Cys Thr Ile Tyr Val Gly Asn Leu Pro Gly
1               5                   10                  15

Asp Ile Arg Glu Arg Glu Val Asp Asp Leu Phe Tyr Lys Tyr Gly Arg
            20                  25                  30

Ile Val Glu Ile Asp Leu Lys Ile Pro Pro Arg Pro Pro Gly Phe Ala
        35                  40                  45

Phe Val Glu Phe Glu Asp Ala Arg Asp Ala Glu Asp Ala Ile Tyr Gly
    50                  55                  60

Arg Asp Gly Tyr Asn Phe Asp Gly His Arg Leu Arg Val Glu Leu Ala
65                  70                  75                  80

His Gly Gly Arg Gly Thr Ser Ser Phe Asp Arg Ser Ser Tyr Ser
            85                  90                  95

Ser Ala Gly Gln Arg Gly Ala Ser Lys Arg Ser Asp Tyr Arg Val Met

```
            100                 105                 110
Val Thr Gly Leu Pro Ser Ser Ala Ser Trp Gln Asp Leu Lys Asp His
            115                 120                 125

Met Arg Arg Ala Gly Asp Val Cys Phe Thr Asp Val Tyr Arg Glu Ala
            130                 135                 140

Gly Ala Thr Ile Gly Ile Ala Asp Tyr Thr Asn Tyr Glu Asp Met Lys
145                 150                 155                 160

His Ala Ile Arg Lys Leu Asp Asp Ser Glu Phe Arg Asn Ala Phe Ser
                165                 170                 175

Arg Thr Tyr Val Arg Val Arg Glu Tyr Asp Ala Arg Ser Arg Ser
            180                 185                 190

Arg Ser Arg Gly Arg Asn Arg Ser Lys Ser Arg Ser Arg Ser His Ser
            195                 200                 205

His Ser Tyr Ser Arg Ser Arg Ser Cys Ser Tyr Ser Lys Ser Arg Ser
        210                 215                 220

Pro Arg Ser Arg Ser Ala Ser Glu Ser Lys Ser Pro Val Lys Ala Arg
225                 230                 235                 240

Ser Pro Ser Arg Ser Pro Pro Val Ser Pro Arg Arg Asp Lys Ser Ala
                245                 250                 255

Ser Arg Ser Pro Ala Arg Ser Lys Ser Leu Pro Arg Ser Cys Ser Pro
            260                 265                 270

Ala Lys Ser Glu
        275
```

<210> SEQ ID NO 7
<211> LENGTH: 1304
<212> TYPE: DNA
<213> ORGANISM: Zea mays

<400> SEQUENCE: 7

```
cacgccggca tccgtcgaag ctgctcgacc tcgactcaag ccttccttgc tccttgccgc    60
cgtcgagtcg tcgcaggaac gatgacccgg cggaacggct gtacgatcta cgtgggcaac   120
ctccccggcg acatccgcga gagggaagtg gatgatctct tctacaagta tggacgtata   180
gtggaaattg acttgaaaat tccaccaagg cctcctggtt ttgcttttgt tgagtttgag   240
gacgcacgtg atgctgaaga tgcaatatat ggccgtgatg gatacaactt tgatggccat   300
aggttgcggg tggaattagc ccatggtgga cgaggcacat cttcttttga tcgatctagc   360
agctatagca gtgctggaca acgcggtgcc tcaaaacgtt ctgattaccg tgttatggtt   420
actggattac cttcttcagc atcatggcaa gatctcaagg accatatgcg gcgagctggt   480
gatgtctgtt tcactgatgt gtatcgtgag gctggagcaa ctattggaat agctgattat   540
actaactatg aagatatgaa acacgcgata aggaagctag atgattctga gttccgtaat   600
gcttttcaa ggacatatgt ccgggtgagg agtatgatg ctaggcgcag ccgttctcgc    660
tccagaggca gaaaccgctc taagtcaaga agcagaagcc acagccactc gtactcaaga   720
agcagaagct gcagttatag caagagtagg agcccaagat ctagatctgc ttcagagtca   780
aaatcacctg ttaaggcaag attggggcaa tgtgaggatc tgggaattgc attggtagga   840
taatggaata ttgagaacgt gatgatggtt tggaacgttg atagtcaca gctggattgt    900
gatgcattgt atgacaagtg gactgccacc agcaatagga gcaagatagg gctggcacca   960
cacatacgga caggattttt tgatcaccat ccagatcccc tcctgttctc ccccggcgtg  1020
acaagtctgc aagcaggagt cctgccagga gcaagagtct gccccgatct tgttctccgg  1080
```

```
caaaatcaga gtgaatcgga ttctgcactt gaaacgttca gaaaggcaga gctcgagcta   1140
aaagattgct gtacggatta tgagcactgt gctagtagca ttgctgtccc ttccatattt   1200
ttacaaatac tctgttcttt gaggagatca ctgtatgcta ctactctgta cctgacatga   1260
tgcaaacgtt gttggttttt gaacttagca gaacgatgac tttg                   1304
```

<210> SEQ ID NO 8
<211> LENGTH: 253
<212> TYPE: PRT
<213> ORGANISM: Zea mays

<400> SEQUENCE: 8

```
Met Thr Arg Arg Asn Gly Cys Thr Ile Tyr Val Gly Asn Leu Pro Gly
  1               5                  10                  15
Asp Ile Arg Glu Arg Glu Val Asp Asp Leu Phe Tyr Lys Tyr Gly Arg
             20                  25                  30
Ile Val Glu Ile Asp Leu Lys Ile Pro Pro Arg Pro Pro Gly Phe Ala
         35                  40                  45
Phe Val Glu Phe Glu Asp Ala Arg Asp Ala Glu Asp Ala Ile Tyr Gly
     50                  55                  60
Arg Asp Gly Tyr Asn Phe Asp Gly His Arg Leu Arg Val Glu Leu Ala
 65                  70                  75                  80
His Gly Gly Arg Gly Thr Ser Ser Phe Asp Arg Ser Ser Tyr Ser
                 85                  90                  95
Ser Ala Gly Gln Arg Gly Ala Ser Lys Arg Ser Asp Tyr Arg Val Met
                100                 105                 110
Val Thr Gly Leu Pro Ser Ser Ala Ser Trp Gln Asp Leu Lys Asp His
            115                 120                 125
Met Arg Arg Ala Gly Asp Val Cys Phe Thr Asp Val Tyr Arg Glu Ala
        130                 135                 140
Gly Ala Thr Ile Gly Ile Ala Asp Tyr Thr Asn Tyr Glu Asp Met Lys
145                 150                 155                 160
His Ala Ile Arg Lys Leu Asp Asp Ser Glu Phe Arg Asn Ala Phe Ser
                165                 170                 175
Arg Thr Tyr Val Arg Val Arg Glu Tyr Asp Ala Arg Arg Ser Arg Ser
            180                 185                 190
Arg Ser Arg Gly Arg Asn Arg Ser Lys Ser Arg Ser Ser His Ser
        195                 200                 205
His Ser Tyr Ser Arg Ser Arg Ser Cys Ser Tyr Ser Lys Ser Arg Ser
    210                 215                 220
Pro Arg Ser Arg Ser Ala Ser Glu Ser Lys Ser Pro Val Lys Ala Arg
225                 230                 235                 240
Leu Gly Gln Cys Glu Asp Leu Gly Ile Ala Leu Val Gly
                245                 250
```

<210> SEQ ID NO 9
<211> LENGTH: 1191
<212> TYPE: DNA
<213> ORGANISM: Zea mays

<400> SEQUENCE: 9

```
ccacgcgtcc gcatcccgta cgtctcgacc tcgcagccgc aaacgcgaaa ccctagcctc    60
gagctctatc tccggccaca gctggtcagg ttagcgacga aggatgagca ggcgctggag   120
ccgcacgatc tacgtcggga acctccccgg cgacatccgg gagagggagg tggaggatct   180
gttctacaag tatggtaaaa ttgttgacat tgacctgaag gtccccccaa gaccacctgg   240
```

-continued

```
ttatgctttt gttgagtttg aagatcctcg tgatgctgag gaggcaattg ctggacggga      300
tggatacaac tttgatggac accgtctaag agtggaggct gctcatggtg gtagaggtaa      360
tgcttcctcg catgatcgtt caagtggctt tggtggcggt ggtggagcac gtcgtggtgt      420
gtcgagacac tcagagtatc gtgttcttgt cactggactg ccttcttctg catcatggca      480
ggatttaaag gatcatatgc ggaaggctgg tgatgtttgt ttctctgaag tgtatcgcga      540
aggcggtggc accgtaggaa ttgtggacta cacaaattat gatgatatga aatatgctat      600
aaagaagctg gatgatactg aattcaggaa cgcctttggg cgagcctata taagggtgaa      660
ggaatataac ggcaaacgtg gtcgctccta ctcacgtagc cgaagcccaa gtcgtagtta      720
cagcaaaagc aggagtccga gtaaatcacc caggactcgc cgttcatcat ctagatcccg      780
gtcaagatct gtttcttctc gttcaaggtc cccatcaaaa ggacgttctc catcaagatc      840
accagcaaga tcgaaatctc ctaatgtttc tccagcaaat ggtgaagcag caagccccaa      900
gaagcagagc ccaaacagga gcccatctgg ctcacgctct cctgatgcga agcctgaata      960
aaattgctat gctgttaaag gattgcagat ggagtcagga gctcttcttt tcttaacatt     1020
tgtcctctgt tctagtacca tcagtgtctt atcgcagtac gagattggat gatattaact     1080
atctgtatca gcttgtatcg atggactcca agtgttgtca ctcttgttgt ctagtgtgct     1140
gaaggaccca tttactttg ctaaactttt ccattggtga ttgttggatg c             1191
```

<210> SEQ ID NO 10
<211> LENGTH: 285
<212> TYPE: PRT
<213> ORGANISM: Zea mays

<400> SEQUENCE: 10

```
Met Ser Arg Arg Trp Ser Arg Thr Ile Tyr Val Gly Asn Leu Pro Gly
  1               5                  10                  15

Asp Ile Arg Glu Arg Glu Val Glu Asp Leu Phe Tyr Lys Tyr Gly Lys
             20                  25                  30

Ile Val Asp Ile Asp Leu Lys Val Pro Pro Arg Pro Pro Gly Tyr Ala
         35                  40                  45

Phe Val Glu Phe Glu Asp Pro Arg Asp Ala Glu Glu Ile Ala Gly
     50                  55                  60

Arg Asp Gly Tyr Asn Phe Asp Gly His Arg Leu Arg Val Glu Ala Ala
 65                  70                  75                  80

His Gly Gly Arg Gly Asn Ala Ser Ser His Asp Arg Ser Ser Gly Phe
                 85                  90                  95

Gly Gly Gly Gly Gly Ala Arg Arg Gly Val Ser Arg His Ser Glu Tyr
            100                 105                 110

Arg Val Leu Val Thr Gly Leu Pro Ser Ser Ala Ser Trp Gln Asp Leu
        115                 120                 125

Lys Asp His Met Arg Lys Ala Gly Asp Val Cys Phe Ser Glu Val Tyr
    130                 135                 140

Arg Glu Gly Gly Gly Thr Val Gly Ile Val Asp Tyr Thr Asn Tyr Asp
145                 150                 155                 160

Asp Met Lys Tyr Ala Ile Lys Lys Leu Asp Asp Thr Glu Phe Arg Asn
                165                 170                 175

Ala Phe Gly Arg Ala Tyr Ile Arg Val Lys Glu Tyr Asn Gly Lys Arg
            180                 185                 190

Gly Arg Ser Tyr Ser Arg Ser Arg Ser Pro Ser Arg Ser Tyr Ser Lys
        195                 200                 205
```

| Ser | Arg | Ser | Pro | Ser | Lys | Ser | Pro | Arg | Thr | Arg | Ser | Ser | Arg |
| | | 210 | | | | 215 | | | | 220 | | | |

| Ser | Arg | Ser | Arg | Ser | Val | Ser | Arg | Ser | Arg | Ser | Pro | Ser | Lys | Gly |
| 225 | | | | 230 | | | | 235 | | | | | | 240 |

| Arg | Ser | Pro | Ser | Arg | Ser | Pro | Ala | Arg | Ser | Lys | Ser | Pro | Asn | Val | Ser |
| | | | | 245 | | | | 250 | | | | 255 | | | |

| Pro | Ala | Asn | Gly | Glu | Ala | Ala | Ser | Pro | Lys | Lys | Gln | Ser | Pro | Asn | Arg |
| | | | 260 | | | | | 265 | | | | 270 | | | |

| Ser | Pro | Ser | Gly | Ser | Arg | Ser | Pro | Asp | Ala | Lys | Pro | Glu |
| | 275 | | | | | 280 | | | | 285 | | |

<210> SEQ ID NO 11
<211> LENGTH: 1648
<212> TYPE: DNA
<213> ORGANISM: Zea mays

<400> SEQUENCE: 11

```
ccacgcgtcc gcatcccgta cgtctcgacc tcgcagccgc aaacgcgaaa ccctagcctc      60
gagctctatc tccggccaca gctggtcagg ttagcgacga aggatgagca ggcgctggag     120
ccgcacgatc tacgtcggga acctccccgg cgacatccgg gagagggagg tggaggatct     180
gttctacaag tatggtaaaa ttgttgacat tgacctgaag gtccccccaa gaccacctgg     240
ttatgctttt gttgagtttg aagatcctcg tgatgctgag gaggcaattg ctggacggga     300
tggatacaac tttgatggac accgtctaag agtggaggct gctcatggtg gtagaggtaa     360
tgcttcctcg catgatcgtt caagtggctt tggtggcggt ggtggagcac gtcgtggtgt     420
gtcgagacac tcagagtatc gtgttcttgt cactggactg ccttcttctg catcatggca     480
ggatttaaag gatcatatgc ggaaggctgg tgatgtttgt ttctctgaag tgtatcgcga     540
aggcggtggc accgtaggaa ttgtggacta cacaaaattat gatgatatga aatatgctat     600
aaagaagctg gatgatactg aattcaggaa cgcctttggg cgagcctata aagggtgaa      660
ggaatataac ggcaaacgtg tcgctcctta ctcacgtagc cgaagcccaa gtcgtagtta     720
cagcaaaagc aggagtccga gtaaatcacc caggactcgc cgttcatcat ctagatcccg     780
gtcaagatct gtttcttctc gttcaaggtc cccatcaaaa ggacgttctc catcaagact     840
caattatctt gccctttat ctgggattgt gcggtgatct ggggattgcg cattaagata     900
ttgaggatgg gattttcaca atttgctaca gttcagttga ttttataaga gtttggcata     960
agcgcattgt ttggaatact ggacatagga gcgttaagga ttggtgatct ggattatggt    1020
ggtacagtgg ctaggaatgt acttggagtt caatgcttgg ggaatgagtt ttcttcgtac    1080
ctcaggcaca cttcagatgg ttgctgtagt tcatatatgc actgtcgaca ttgttataca    1140
acaatgttac atttgcacgg aactgaacac ttctattttc atgagctttt attgctttga    1200
ttcgacgcgg catcatggct tttggaacca agttgttaaa gctgcatttt ggatattgaa    1260
tcagttgttt ctggaacgtt ttgcagatca ccagcaagat cgaaatctcc taatgtttct    1320
ccagcaaatg gtgaagcagc aagcccaag aagcagagcc caaacaggag cccatctggc    1380
tcacgctctc ctgatgcgaa gcctgaataa aattgctatg ctgttaaagg attgcagatg    1440
gagtcaggag ctcttctttt cttaacattt gtcctctgtt ctagtaccat cagtgtctta    1500
ttgcagtacg agattggatg atattaacta tctgtatcag cttgtatcga tggactccaa    1560
gtgttgtcac tcttgttgtc tagtgtgctg aaggacccat ttacttttgc taaacttttc    1620
cattggtgat tgttggatgc atggtcgt                                       1648
```

<210> SEQ ID NO 12
<211> LENGTH: 257
<212> TYPE: PRT
<213> ORGANISM: Zea mays

<400> SEQUENCE: 12

```
Met Ser Arg Arg Trp Ser Arg Thr Ile Tyr Val Gly Asn Leu Pro Gly
  1               5                  10                  15
Asp Ile Arg Glu Arg Glu Val Glu Asp Leu Phe Tyr Lys Tyr Gly Lys
             20                  25                  30
Ile Val Asp Ile Asp Leu Lys Val Pro Pro Arg Pro Pro Gly Tyr Ala
         35                  40                  45
Phe Val Glu Phe Glu Asp Pro Arg Asp Ala Glu Glu Ile Ala Gly
     50                  55                  60
Arg Asp Gly Tyr Asn Phe Asp Gly His Arg Leu Arg Val Glu Ala Ala
 65                  70                  75                  80
His Gly Gly Arg Gly Asn Ala Ser Ser His Asp Arg Ser Gly Phe
                 85                  90                  95
Gly Gly Gly Gly Gly Ala Arg Arg Gly Val Ser Arg His Ser Glu Tyr
            100                 105                 110
Arg Val Leu Val Thr Gly Leu Pro Ser Ser Ala Ser Trp Gln Asp Leu
        115                 120                 125
Lys Asp His Met Arg Lys Ala Gly Asp Val Cys Phe Ser Glu Val Tyr
    130                 135                 140
Arg Glu Gly Gly Gly Thr Val Gly Ile Val Asp Tyr Thr Asn Tyr Asp
145                 150                 155                 160
Asp Met Lys Tyr Ala Ile Lys Lys Leu Asp Asp Thr Glu Phe Arg Asn
                165                 170                 175
Ala Phe Gly Arg Ala Tyr Ile Arg Val Lys Glu Tyr Asn Gly Lys Arg
            180                 185                 190
Gly Arg Ser Tyr Ser Arg Ser Arg Ser Pro Ser Arg Ser Tyr Ser Lys
        195                 200                 205
Ser Arg Ser Pro Ser Lys Ser Pro Arg Thr Arg Arg Ser Ser Ser Arg
    210                 215                 220
Ser Arg Ser Arg Ser Val Ser Ser Arg Ser Arg Ser Pro Ser Lys Gly
225                 230                 235                 240
Arg Ser Pro Ser Arg Leu Asn Tyr Leu Ala Leu Leu Ser Gly Ile Val
                245                 250                 255
Arg
```

<210> SEQ ID NO 13
<211> LENGTH: 2258
<212> TYPE: DNA
<213> ORGANISM: Zea mays

<400> SEQUENCE: 13

| | | | | |
|---|---|---|---|---|
| ccacgcgtcc | gcatcccgta | cgtctcgacc | tcgcagccgc | aaacgcgaaa | ccctagcctc | 60 |
| gagctctatc | tccggccaca | gctggtcagg | ttagcgacga | aggatgagca | ggcgctggag | 120 |
| ccgcacgatc | tacgtcggga | acctccccgg | cgacatccgg | agagggagg  | tggaggatct | 180 |
| gttctacaag | tatggtaaaa | ttgttgacat | tgacctgaag | gtcccccaa  | gaccacctgg | 240 |
| ttatgctttt | gttgagtttg | aagatcctcg | tgatgctgag | gaggcaattg | ctggacggga | 300 |
| tggatacaac | tttgatggac | accgtctaag | agtggaggct | gctcatggtg | gtagaggtaa | 360 |

```
tgcttcctcg catgatcgtt caagtggctt tggtggcggt ggtggagcac gtcgtggtgt    420
gtcgagacac tcagagtatc gtgttcttgt cactggactg ccttcttctg catcatggca    480
ggatttaaag gatcatatgc ggaaggctgg tgatgtttgt ttctctgaag tgtatcgcga    540
aggcggtggt aagtagcatt tggggttaaa gtcgctgcct ttattgcaat tttaaaatgt    600
tcataaaatc tttagaagca cagaatacat ttgcagtgta ttttttttatt caaaagcaat    660 aagccaatta ggttgatctt tttgcccttt tggtgccatt gtcatggcag aactaacgac    720
acatcctcta agatactgac atactgtgga tccatatatg gctacatgaa gtccaatttg    780
ttccattttg tttttctttc agtattctca tttcccggat cagaaaacta ctgaccttcg    840
atattttaaa tattcattta taaaatacta attatttaat tgttataaaa ggtaaattag    900
gcacagttga gaaatgcttg ggattgcaag aataataatc ttgccacaag aaagttcaaa    960
cttgcttggt tacatcataa tcaaatgtac cacagtaaca attttacat gctcacactt    1020 gtgaatggat cgaatgtatt gggacaatta ctaaagctca tagccattat tgaagtaatg    1080
tgcctgtcat acttagactc tatggttcaa gcagatccag aactgaattc ttgagttaaa    1140
ggatattgta aaggatattg tgttcgaaat ttgaaaatgg acttattagt tggtcacatc    1200
tgtaagctgc caacatttat agggatatcc atcacacatc ctatattatc aattcccata    1260
aatgaccatc tgtctctagc tatgacaagt tcagtcctaa tttatatggc agaaaaatcc    1320
atcaataatt tctctcccct tggttagcta tatggacaca gccaatttga tgacttgtca    1380
agttttacaa agatcaccta cttagccttc acatatctga tttgttccaa ataaagtac    1440 tcatcattgc tgtttgttct aggatttggc gcatataaat cctgcgtaac ataatactgg    1500
catctattat tatttattgt gaaggtttat ttcattcggt tgcttggttt tcaaccttat    1560
tttcttcaag gatgtgatgt aaagctatat atgtttcact tctctttggc aagttttttca    1620 ttatatgttt ctattttgtt acaggcaccg taggaattgt ggactacaca aattatgatg    1680
atatgaaata tgctataaag aagctggatg atactgaatt caggaacgcc tttgggcgag    1740
cctatataag ggtgaaggaa tataacggca acgtggtcg ctcctactca cgtagccgaa    1800
gcccaagtcg tagttacagc aaaagcagga gtccgagtaa atcacccagg actcgccgtt    1860
catcatctag atcccggtca agatctgttt cttctcgttc aaggtcccca tcaaaggac    1920 gttctccatc aagatcacca gcaagatcga aatctcctaa tgtttctcca gcaaatggtg    1980
aagcagcaag ccccaagaag cagagcccaa acaggagccc atctggctca cgctctcctg    2040
atgcgaagcc tgaataaaat tgctatgctg ttaaaggatt gcagatggag tcaggagctc    2100
ttcttttctt aacatttgtc ctctgttcta gtaccatcag tgtcttatcg cagtacgaga    2160
ttggatgata ttaactatct gtatcagctt gtatcgatgg actccaagtg ttgtcactct    2220
tgttgtctag tgtgctgaag gacccattta ctttttgct                          2258
```

<210> SEQ ID NO 14
<211> LENGTH: 150
<212> TYPE: PRT
<213> ORGANISM: Zea mays

<400> SEQUENCE: 14

Met Ser Arg Arg Trp Ser Arg Thr Ile Tyr Val Gly Asn Leu Pro Gly
 1               5                  10                  15

Asp Ile Arg Glu Arg Glu Val Glu Asp Leu Phe Tyr Lys Tyr Gly Lys
             20                  25                  30

Ile Val Asp Ile Asp Leu Lys Val Pro Pro Arg Pro Pro Gly Tyr Ala

```
                 35                  40                  45
Phe Val Glu Phe Glu Asp Pro Arg Asp Ala Glu Ala Ile Ala Gly
     50                  55                  60

Arg Asp Gly Tyr Asn Phe Asp Gly His Arg Leu Arg Val Glu Ala Ala
65                   70                  75                  80

His Gly Gly Arg Gly Asn Ala Ser Ser His Asp Arg Ser Gly Phe
                 85                  90                  95

Gly Gly Gly Gly Gly Ala Arg Arg Gly Val Ser Arg His Ser Glu Tyr
                100                 105                 110

Arg Val Leu Val Thr Gly Leu Pro Ser Ser Ala Ser Trp Gln Asp Leu
            115                 120                 125

Lys Asp His Met Arg Lys Ala Gly Asp Val Cys Phe Ser Glu Val Tyr
    130                 135                 140

Arg Glu Gly Gly Gly Lys
145                 150

<210> SEQ ID NO 15
<211> LENGTH: 30
<212> TYPE: DNA
<213> ORGANISM: Zea mays

<400> SEQUENCE: 15
gtcactcatt acggcaaagt gtgggtcaat                                      30

<210> SEQ ID NO 16
<211> LENGTH: 26
<212> TYPE: DNA
<213> ORGANISM: Zea mays

<400> SEQUENCE: 16
gcttttcttt gccgttttcg tcggta                                          26

<210> SEQ ID NO 17
<211> LENGTH: 29
<212> TYPE: DNA
<213> ORGANISM: Zea mays

<400> SEQUENCE: 17
atgagcaggc gctggagccg cacgatcta                                       29

<210> SEQ ID NO 18
<211> LENGTH: 27
<212> TYPE: DNA
<213> ORGANISM: Zea mays

<400> SEQUENCE: 18
gccaccaaag ccacttgaac gatcatg                                         27

<210> SEQ ID NO 19
<211> LENGTH: 23
<212> TYPE: DNA
<213> ORGANISM: Zea mays

<400> SEQUENCE: 19
gaagaaggca gtccagtgac aag                                             23

<210> SEQ ID NO 20
<211> LENGTH: 27
<212> TYPE: DNA
<213> ORGANISM: Zea mays
```

<400> SEQUENCE: 20
gagagaaatt attgatggat ttttctg                               27

<210> SEQ ID NO 21
<211> LENGTH: 28
<212> TYPE: DNA
<213> ORGANISM: Zea mays

<400> SEQUENCE: 21
gaaaaccaag caaccgaatg aaataaac                              28

<210> SEQ ID NO 22
<211> LENGTH: 28
<212> TYPE: DNA
<213> ORGANISM: Zea mays

<400> SEQUENCE: 22
gaccttgaac gagaagaaac agatcttg                              28

<210> SEQ ID NO 23
<211> LENGTH: 32
<212> TYPE: DNA
<213> ORGANISM: Zea mays

<400> SEQUENCE: 23
gctttaacaa cttggttcca aaagccatga tg                         32

<210> SEQ ID NO 24
<211> LENGTH: 31
<212> TYPE: DNA
<213> ORGANISM: Zea mays

<400> SEQUENCE: 24
gacattaggt aaaataatgg gacgatttta g                          31

<210> SEQ ID NO 25
<211> LENGTH: 30
<212> TYPE: DNA
<213> ORGANISM: Zea mays

<400> SEQUENCE: 25
gttaagaaaa gaagagctcc tgactccatc                            30

<210> SEQ ID NO 26
<211> LENGTH: 32
<212> TYPE: DNA
<213> ORGANISM: Zea mays

<400> SEQUENCE: 26
catccgtcga agctgctcga cctcgactca ag                         32

<210> SEQ ID NO 27
<211> LENGTH: 33
<212> TYPE: DNA
<213> ORGANISM: Zea mays

<400> SEQUENCE: 27
gcatcagaga ataacaatag ctgcatacta caa                        33

<210> SEQ ID NO 28
<211> LENGTH: 4271
<212> TYPE: DNA
<213> ORGANISM: Zea mays

<400> SEQUENCE: 28

```
catccgtcga agctgctcga cctcgactca agccttcctt gctccttgcc gccgtcgagt        60
cgtcgcaggt gaggctccgc gaaccctct ccgccccgga agccgtagtc ctccggtcga        120
aatatagtgt gcaattctgt tcctgtagaa ggtgctgctt ctttctctcg aacacagcag       180
gtgctgcttt tggaattatt tgctcgtctc ggcgttccgg cgctcagaat tggatccgtt       240
cctggccagg attactcgtt ttagtagtgt agacttgttc cccagatgcc gcaccagttc       300
ggaagtttat tcgcaacagt ttgcttgggt ctgttcgtcc tggtggctga ttcagtatcc       360
ttgttgcagg aacgatgacc cggcggaacg gctgtacgat ctacgtgggc aacctccccg       420
gcgacatccg cgagagggaa gtggatgatc tcttctacaa ggtgagtggt tggttgggtt       480
tgtgtaccga gcttcccacc ctattttttag ggcttctcgt cgaatgctag atccgtgggg      540
aggttgttgt ggtgtcagtc aagcctgcga tatgatatg gggagattag aggagtgttg        600
gggatgttag aggagtgttg gggatgtttt ctttatggct atggctcaat attgctgaag       660
tcgaagagat gcctatgatg taatgtagcg tttgctcata ttgatatttg cagtttaata       720
aactcttact gtgagtttta atcgtcgt gtgtgttaga caatgcactt gttttttca          780
ctgtattgtc acaatctatt tggtgatga ttgaaagttc tgttcgttgt gaacttcacc        840
actgctaatt gtgttttgcc ttctaacacc atctaatcta atatggatgg agctctggaa       900
gggaaggcaa tgtggattgc gaatggtcaa tttttgtttg tatctctatg actctacttt       960
ggttgattaa ctttcctgga tgttaaattt atgttttacc ttctgcttct gcagtatgga       1020
cgtatagtgg aaattgactt gaaaattcca ccaaggcctc ctggttttgc ttttgttgag       1080
gtaagttggc cggtgtctgt tttatatgag ggtattttgt actcaataga tttacatcca      1140
taatttgtgc caggttgaat gttttttatc acaaaccttg tgttttcagt ggcgaatttt      1200
taggaggttt aataccttct tttaaggaaa ctaaaaagaa tattgcctaa aacgtttatt      1260
gttccaacat atgaacatat ctaatgtacg caacaatgac aaccatggaa taaatcagta     1320
atgctaagta ctctattaaa tgttatgcaa ggattactaa attattctct aaaatcaata     1380
atctaggcag ctaagatgat ggaagactaa cagcacagtg atgcatttg cagtttgagg      1440
acgcacgtga tgctgaagat gcaatatatg gccgtgatgg atacaacttt gatggccata     1500
ggttgcgggt tggtggatct tgatgaagac ctgtttcatt agagatctcc aggttacaga     1560
gatgatagtt atctgaatta ttctaatgtt atttataatc tatatacagg tggaattagc     1620
ccatggtgga cgaggcacat cttcttttga tcgatctagc agctatagca gtgctggaca     1680
acgcggtgcc tcaaaacgtt ctgattaccg tggtttgtat tttttttattc ccaaatttca    1740
aagcttataa cttgaaaact ctctctgttc ttactgtatc ggttcattga ttatgcagtt     1800
atggttactg gattaccttc ttcagcatca tggcaagatc tcaaggtttg gtgaagatct     1860
aaggtcatta gctattgttt tgccttata atccttaatt ttactttcat gttcaggacc      1920
atatgcggcg agctggtgat gtctgtttca ctgatgtgta tcgtgaggct ggaggttaat    1980
tttgaaacgt tctgatgtta tcaatttatt acacatttgg ctgaccttt ggatagcatg      2040
actgtcgttc aaactgtatc aaatcatatt ttagaaggaa tgtctataaa aactcgtatc    2100
taatttacg tttatgattg cagcaactat tggaatagct gattatacta actatgaaga     2160
tatgaaacac gcggtatgtt ttaaagtgtt ttcttcttct tcttcttccc tttaaaatag    2220
aagttgtgta ctgacatgtt ttaaataaga ttgatcactg gaaaaggaga aacttcgtga     2280
```

```
tatgtgtaat ctttgtacct gtctgtgcat acttgcatat ttccatgaag atatgtactg    2340
acaactagtt acttttatct tgtagataag gaagctagat gattctgagt tccgtaatgc    2400
tttttcaagg acatatgtcc gggtatggtc atcttttgt cctgatgatt agcagtattc     2460
aaatgctgta tcggctcatt tgtttcatct catctcaaat gaaaattagc atgctctcat    2520
catttgtctt actaaggtg agggagtatg atgctaggcg cagccgttct cgctccagag     2580
gcagaaaccg ctctaagtca agaagcagaa gccacagcca ctcgtactca agaagcagaa    2640
gctgcagtta tagcaagagt aggagcccaa ggtacatttt tcaattttct tcatgctcaa    2700
atgttgacta gggtacatcg aaggtgtaac aggcttttt ttctcaatga ttcagatcta     2760
gatctgcttc agagtcaaaa tcacctgtta aggcaaggta tgaatagttg aatttggtac    2820
tgaatggttt gaaatttaga gaagttctgt tttcaagtaa tagtagctca aaatattggt    2880
gcctacaatt gcaggggaa aatatcagca gcctagtttt tttctagatc tgtttgaat      2940 tttccctttt tgttattgta ctttatggtt tatattatgc ttcttgatgc tgcattttc     3000 attatatgag tttggatttt cactgcatct gattaacatg taacattgtg tgtgactgga    3060
tagctattct tcattgttga agatttgttc ttttcttcac tagattgggg caatgtgagg    3120
atctgggaat tgcattggta ggataatgga atattgagaa cgtgatgatg gtttggaacg    3180
ttggatagtc acagctggat tgtgatgcat tgtatgacaa gtggactgcc accagcaata    3240
ggagcaagat agggctggca ccacacatac ggacaggatt ttttggtata atcgaatact    3300
attgacttca gcacttccat tctgaaatat aaaaccttgg tctcaaactc ttaatgatga    3360
ggttgcagcc ttaccctcaa atataaatgt gagctttaac attgattttt ctggtaaaaa    3420
agttgcacaa ctgaaacaag aaagctgtgg ccctgttgga ccatttcaat ccatgttggc    3480
tatatctttg tttgctgaat tgtagtttcc tcttatatga aattgcaatt tctaaataga    3540
tttgagcttt tttatatata ttctgaatgg cagaggcacg ggtggatatt gcatgtggcc    3600
gcttaatatt ttcagaatat atatatttat gggttctacg atatttgggc taaatcatat    3660
tttcatgcag cattatggac taacattttt gtatacgttt tgcagatcac catccagatc    3720
ccctcctgtt tctgtaagtt tttttttgat ataaacaaag tatttttatc caatacttt     3780 ttatgtgacc agctgagtgt tgcacagccc cggcgtgaca agtctgcaag caggagtcct    3840
gccaggagca agagtctgcc ccgatcttgt tctccggtac gaaacttcca tactattagt    3900
cttgttggta tgcagtatgc taatgataaa ccatatatat atattttatg tattttgttt    3960
ggttgattgc aggcaaaatc agagtgaatc ggattctgca cttgaaacgt tcagaaaggc    4020
agagctcgag ctaaaagatt gctgtacgga ttatgagcac tgtgctagta gcattgctgt    4080
cccttccata tttttacaaa tactctgttc tttgaggaga tcactgtatg ctactactct    4140
gtacctgaca tgatgcaaac gttgttggtt tttgaactta gcagaacgat gactttgatc    4200
agctccatcc attccttcca ttttttttc tgaatatttc aaaagattgt agtatgcagc     4260
tattgttatt c                                                         4271
```

<210> SEQ ID NO 29
<211> LENGTH: 4748
<212> TYPE: DNA
<213> ORGANISM: Zea mays

<400> SEQUENCE: 29

```
ctgtcatccc gtacgtctcg acctcgcagc cgcaaacgcg aaaccctagc ctcgagctct      60
atctccggcc acagctggtc aggtaggaat ctcctttcct catcgttcct cgggtggttc     120
```

-continued

```
gtgccccgcg ccccgctgct ttctgggttt gttttgattt ttgaaccttc tcttgtgggg      180
tgttgtgttg ggttgcggag atgtggatgc ggacgcggac gcggcgaggg ctgctttgct      240
gattgattat tgctttgtgg gtaggttagc ggcgaaggat gagcaggcgc tggagccgca      300
cgatctacgt cgggaacctc cccggcgaca tccgggagag ggaggtggag gatctgttct      360
acaaggtggg gaattttct aactgttcga ttccttgcta ccctattaaa cctagcaaat       420
agcgcagccc gtgttactgt atttggctgg gcttggttac cgtgtgctta gattcagcac      480
ctccgatgcc tatactactt tcttaatgca acaggatgcg aagcactgct atgctcttat      540
ggtcgtgccc ataatcgtag aaaactgggt agcttggata atcttgtgct atttgggacc      600
acctagtttc tctactacac tcacaatgta acctcaagct gtggattgcg cttgcggacg      660
ttgtttatag ttcttgttca cttgaaaagt ttcatgattt tatactaata atgtccaatc      720
ttgtaaaact ttgaatgcag tatggtaaaa ttgttgacat tgacctgaag gtcccccaa      780
gaccacctgg ttatgctttt gttgaggtaa gattctcctg aatgtgttga ataacatggc      840
tatctttccc ccttaaagat gatcttgtgt tggttgatga ctcatgtcac aaacagcaaa      900
ttcaaggtta ctttgctaat cttgcagttt gaagatcctc gtgatgctga ggaggcaatt      960
gctggacggg atggatacaa ctttgatgga caccgtctaa gagtaagcta atcagtgatt     1020
tgataagcta acatgtgtac tctctttctc ttctatctgt tgatccaata cctacttctg     1080
tggtcaggtg gaggctgctc atggtggtag aggtaatgct tcctcgcatg atcgttcaag     1140
tggctttggt ggcggtggtg gagcacgtcg tggtgtgtcg agacactcag agtatcgtgg     1200
tatggtttct attcatgttg aacatcagtg attgttaatc ttctctgtct gcaaccttta     1260
acttgatcct ttgcaaacag ttcttgtcac tggactgcct tcttctgcat catggcagga     1320
tttaaaggtc tgtgtgaaaa cttcttccct cgtgttcttt ccgaagacta tcgtgtgtct     1380
cattaacacc aaatatattc ttcccaggat catatgcgga aggctggtga tgtttgtttc     1440
tctgaagtgt atcgcgaagg cggtggtaag tagcatttgg ggttaaagtc gctgccttta     1500
ttgcaatttt aaaatgttca taaatctttt agaagcacag aatacatttg cagtgtatttt    1560
ttttattcaa aagcaataag ccaattaggt tgatcttttt gcccttttgg tgccattgtc     1620
atggcagaac taacgacaca tcctctaaga tactgtggat ccatatatgg agtcccattt     1680
gttccatttc tcaactgtgc ctaatcttct ctgtctacat gaagtccaat tgttccatt     1740
ttgttttttct ttcagtattc tcatttcccg gatcagaaaa ctactgatct tcgatatttt    1800
aaatattcat ttataaaata ctaattattt aattgttata aaaggtaaat taggcacagt     1860
tgagaaatgc ttgggattgc aagaataata atcttgccac aagaaagttc aaacttgctt     1920
ggttacatca taaccaaatg taccacagta acaattttta catgctcaca cttgtgaatg     1980
gatcgaatgt attgggacaa ttactaaagc tcatagccat tattgaagta atgtgcctgt     2040
catacttagt ctctatggtt caagcagatc cagaactgaa tttttgagtt aaaggatatt     2100
gtgttcgaaa tttgaaaatg gacttattag ttggtcacat ctgtaagctg ccaacattta     2160
tagggatatc catcacacat cctatattat caattcccat aaatgaccat ctgtctctag     2220
ctatgacaag ttcagtccta atttatatgg cagaaaaatc catcaataat ttctctcccc     2280
ttggttagct atatggacac agccaatttg atgacttgtc aagttttaca aagatcacct     2340
acttaggctt cacatatctg atttgttcca aaataaagta ctcatcattg ctgtttgttc     2400
taggatttgg cgcatataaa tcctgcgtaa cataatactg gcatctatta ttatttattg     2460
```

-continued

```
tgaaggttta ttt cattcgg ttgcttggtt ttcaacctta ttttcttcaa ggatgtgatg      2520
taaagctata tatgtttcac ttttctttgg caagttttc atcatatgtt tctattttgt       2580
tacaggcacc gtaggaattg tggactacac aaattatgat gatatgaaat atgctgtaag      2640
tccataatac attccttgt ctcatgacat tggcttgtca atttgtgtga atcatttcat       2700
tctatagatt ttttctcatg gatataccgt ttgaccttct acaataactt atctttggtt     2760
gtttccctat ctgtcactgt tagttcgatc tcttctacaa tagccataat gtgtccttaa      2820
tgctttgaac tatccatttg gcaatgacaa ctcatcacag ataaagaagc tggatgatac      2880
tgaattcagg aacgcctttg ggcgagccta tataagggta agcattgtag cctgtaactg      2940
gtttatttct tggaatcact tgtgtagttt gttgttaagt ttgcaccta ttctttacag       3000 gtgaaggaat ataacggcaa acgtggtcgc tcctactcac gtagccgaag cccaagtcgt      3060
agttacagca aaagcaggag tccgaggtat gctgctgtta atgttatgtc aggtagcctt      3120
gttgataact aataattaat actgaatatg ctttgcagta aatcacccag gactcgccgt      3180
tcatcatcta gatcccggtc aagatctgtt tcttctcgtt caaggtcccc atcaaaagga      3240
cgttctccat caaggtaaca tacactttca aattctgagc tttgaatcct tatatatgtc      3300
aagttctttt ctactgtttt ctccaaatca caatatatat gcattagtag aatatctgga     3360
caaattatga atatgcctac ttctgtatca taatttcgtg ttgcctaccc tgtcggcctt      3420
tttcctttgc aaagattgct gttgttttgt agtctaaaac agtggctatc aatctttatt     3480
aaagtgctgt cattgttccg taaccttcat cggtctgaat attttgtatc taataataag     3540
cttctcagtt aagttcaagt taacatagtt acactcccat gcatgtatac aatgatgatg      3600
gcttgctgta cagtctgatt gcttggggt tccttctcaa gtgctcagag tctaatgaac      3660
gatatgaact gcttagtctg ttctgttttg ttttgaaga ctcaattatc ttgccctttt      3720
atctgggatt gtgcggtgat ctggggattg cgcattaaga tattgaggat gggattttca     3780
caatttgcta cagttcagtt gattttataa ggtatggtta ttaattgaga gtttgtatga     3840
aaagctaaaa tcgtcccatt attttaccta atgtcctgta actgattgac atcagagttt     3900
ggcataagcg cattgtttgg aatactggac ataggagcgt taaggattgg tgatctggat     3960
tatggtggta cagtggctag gaatgtactt ggagttcaat gcttggggaa tgagttttct     4020
tcgtacctca ggcacacttc agatggttgc tgtagttcat atatgcactg tcgacattgt     4080
tatacaacaa tgttacattt gcacggaact gaacacttct attttcatga gctttattg      4140 ctttgattcg acgcggcatc atggcttttg gaaccaagtt gttaaagctg cattttggat      4200
attgaatcag ttgtttctgg aacgttttgc agatcaccag caagatcgaa atctcctaat      4260
gtttctgtaa gttcccttca tcattttgat aataatttt tgttattttg ttgcctattt      4320
ttatatctcc taaatgtca atgtagccag caaatggtga agcagcaagc cccaagaagc      4380
agagcccaaa caggagccca tctggctcac gctctcctga tgtaaaatga ttctactctt      4440
atttgctgta gttgttaatg gcaaacacag ctgaactgac aacaatcggt caaaatttgc      4500
aggcgaagcc tgaataaaat tgctatgctg ttaaaggatt gcagatggag tcaggagctc      4560
ttcttttctt aacatttgtc ctctgttcta gtaccatcag tgtcttattg cagtacgaga      4620
ttggatgata ttaactatct gtatcagctt gtatcgatgg actccaagtg ttgtcactct      4680
tgttgtctag tgtgctgaag gacccattta cttttgctaa acttttccat tggtgattgt     4740
tggatgca                                                                4748
```

<210> SEQ ID NO 30
<211> LENGTH: 21299
<212> TYPE: DNA
<213> ORGANISM: Zea mays

<400> SEQUENCE: 30

| | | | | | |
|---|---|---|---|---|---|
| catagaagcc | ttgatgcatg | attgaatacg | gtacatgtta | ttatgtttga | aatacccgtg | 60 |
| tagtttgatt | aagcgcgtat | cagtaggtga | catacagtgc | agatttgtac | atttttttta | 120 |
| acacataaaa | ggcaactaga | gaatatgtta | tagactcata | gtgctctttg | ttacaatttc | 180 |
| tgttgaagca | tcattctttc | ttggtcaagg | tctcatggat | gctgctactt | catttttttt | 240 |
| aataatgctc | ggcatatagt | cataggccac | catgttcttc | ctgttgtttc | gattttcgac | 300 |
| taggatattt | taaatgaaat | tccgtgtctt | ggtattacca | tgctgttgtt | ttgactttcg | 360 |
| actgggatat | ttcaaacaaa | attctgtctc | ttgctattac | cattgtatga | ctgcctcctt | 420 |
| agaaaattgg | tgtaggggttt | taggtaaatg | acacattctt | ggagaaccat | attctggtga | 480 |
| ccgtactatc | tttggcatgc | taaaatttcg | ttgtgtttgc | cccagcattt | tcccattttt | 540 |
| gagacaatga | tgtacttacc | cgtgtttaac | tgcagaaaac | aatgagcagg | cgcaacagcc | 600 |
| gtaccatcta | tgtaggcaat | ctccctgggg | acatccgtga | gagggaggtt | gaggatctct | 660 |
| tctacaaggt | ggattgcaat | tgtttaacgt | gtacctttct | tcgattttc | attttgcaaa | 720 |
| caagtgttgg | ttggtcaggg | catatgctaa | ttcctaacaa | gtcagtaaca | ttttctgtct | 780 |
| cagcaagaca | gcaatttcag | tatcctatta | atgtgagaat | gtagtatgga | gctgaatgtt | 840 |
| cacatttttt | atttatgata | ttaactagca | taagtctatc | tagcattccc | ttagagcatc | 900 |
| tccaaaatct | tatttaaagt | cttccctagc | ttaaaattct | tgggaaaaac | aaaaaaacta | 960 |
| gccttcaaca | gcttccctaa | atcctgccca | acttattgat | agcccaaaaa | ctcccctcat | 1020 |
| ttgtagttac | taatagggag | acttttggtt | cctccaatac | tatttcctac | tgccacatca | 1080 |
| ccagtactcc | cgccactaca | ttgccatttt | tgtttccggc | accccatcac | cactacctac | 1140 |
| gtcgtcccat | cgccgaccca | tacgttgccg | gccatccaac | gccagctatt | caccgtcaac | 1200 |
| tggctcattg | tctacgatgc | ccctttgcca | ccctgtcccc | cagttatgct | ccactaccta | 1260 |
| ccagctacaa | cacagtggga | aaaaataacg | tgagaaagat | tacctaggtc | aaagatgaca | 1320 |
| taatgctcga | atggatgcgg | gcattaaaga | tgatctgacc | tagtttaaat | tattttttggt | 1380 |
| atatatttag | gggaactgtt | ggagattaaa | agaaaatcca | ctcccaataa | tttttaggct | 1440 |
| gctcccaaaa | accatgttgg | tgcagcattg | cctggtccca | agtccatgta | caagtaggag | 1500 |
| ggttgcgtga | ggcgtggcaa | gcaagctata | aaaacttagc | cactcataga | aaactgttgg | 1560 |
| ggcataaccc | tcttagcgac | gtgccatatc | ggaacccggg | tatggtgtta | atgggaaag | 1620 |
| ggccgggcag | ccagccctt | ggtggcgcgt | cgtgtcgtga | tctggatgcg | gtgtcaagtg | 1680 |
| agcaaggatc | gggtcgtcgc | ttccttagtg | gcgcgctaca | tcggcgcccg | ggtgtagtga | 1740 |
| caaatgggca | agggtcttcg | catctgtctc | aacgggtgca | aggggtaagg | aagctagttg | 1800 |
| agccggctag | gatccgtgta | ggtagttgga | acgtagggtc | ccttacaggt | aagctaagag | 1860 |
| agttagtcga | tgtagcgagc | aggaggcaca | ttagtatcct | atgtgtgcat | gagacaagat | 1920 |
| ggaaggggca | aaaagcgaag | gaggtggaga | acactggttt | caaattttag | tactcaggaa | 1980 |
| cagtggcaaa | caaaaatgga | gtatcctgat | tgataagacc | cttaaggatg | gagtggtgga | 2040 |
| cgtcaaaagg | cagggagata | ggattatcct | aatcaaaata | gttttgggg | atgtagtctt | 2100 |
| gaacattata | agtgcatatg | cccctcagat | tggtctcagt | gcgagcgaga | agaggaagtt | 2160 |

```
ctgggaagac ttagatggca tggtcagagc aataccoacc aatgagaagc ttttcatagg    2220
agatctcaat ggtcatgtag gttcaacaaa tgcatgttat gagctggctc atggaggttt    2280
cgggtatgtt agtaggaatc aaggagagga tattttggac ttttctgtag cctacaacct    2340
agtgatagcc aacactttct tcagaaagag agattctcat ttggtgactt agcagtggcc    2400
atcgttcgag ccagatcgac ttcgttctca caaggagaga agataaacaa gcatgtttgg    2460
attgtaacgt gatacccgga gagtgttgtg ccccaacata atcttgtggt ggctgacttc    2520 cgttttttgga tccgtaccca tatggataaa caagccaaaa ttgcgaggat gaagtgggga    2580
aactcaaagg ggagacatcc gaaattttta gagaaagagt ttttgtggag ggcgcttggt    2640
tcgaagaaga aaatgcatac aacatgcgga tgaagatggc aacttgtatt aggaaggtgg    2700
cgtcataggt gttttgggtg accaaaggga gcagaggtga acctaaggat acttggtggt    2760
ggaccgagga cgttcaaaag gcaataaagg agaagaaaga atgttacagg agcttgttcc    2820
atgataggag cgcgatcaac atagtgatgt ataaggtggc aaagaagact gcaaggcaag    2880
ctgtgagtga ggcaaagggt cgagcctatg atgatcttta ttgaagacta agtacaaagg    2940
aaggggagaa ggatgtcttt aagatgacta ggattcggga aacgaagacg agggaccctca    3000 accaaattaa atgcatcaag gatggagatg gatcaactct tggtgaaagg acaagacatc    3060
aaacaacggt ggcagagtta ttttgacaat cttttcaatg gtgagaataa gactatggac    3120
acccaattgg atgactcctt tgatgatttt tttctagaac gcgtaggaga actgcgcatc    3180
ttatatatta gagaggaaaa aacatattac aacagaggag atgttgctga gcaactctcc    3240
ccttataaac ccgaaagtga ttacagattg ttgctgaaac ttgacccgat cacgcccagg    3300
gcagcaactg agcccaagct cccaaactcc ttagctcctg ctattaccca gcaaacgtat    3360
tcatccgaga aacaccggaa aatcgtgggt aatgagggag cctccccatg gaacactgct    3420
ctgtttctct gaagccatag accccaagcc cccaggatga ttagagagtt aagccccttt    3480
tgtcacgtct tgacaaccct aaggcttgcc ttttccccacc agtctgcaaa attctcctca    3540
tcagctgttg gagtgaggtg ccccaaaacca atagcagcaa gactagtgtg ccaaaattgc    3600
cgggcaaaaa tgcacgcagt aagtaggtgc tgaattgttt cttgggcttg atcacacatg    3660
gggcaaacat ctgggtgtgg cattcccctc aactgtaatc tgtcggctat ccaacatttg    3720
ttccttatag ccaaccaaag gaagaacttg catttaggag gagcccaggt cttccataat    3780
ctcttccaag gctcaaaaac agtacacagg acccaagaat cagaggtcaa agaagcttta    3840
aagaggatga aaggggcaa ggcaatgggc ccagatggta ttccaataga ggtgtggaaa    3900
tgccttgggg atattgctat cgttcgacta accaagttgt tcaaccatat ttttcgatca    3960
aacaagatgc ccgatgagtg gagcaggagt acattagtaa caatcttcaa gaacaaggga    4020
gatattcaaa gttgtaccaa atatcgaggg attaagctca tgagccacac tatgaagcta    4080
tgagagagtt attaagcatc gcctgagagg aatgacacat atcaccatga accaatttgg    4140
attcatgcct ggaaggtcaa ccatggaagc aattttctta ataagacaag tcatggagcg    4200
gtataaggag tagaaggagg acttgcacat ggttttatc gacttggaaa aggcttatga    4260
taaaataact aggaatctca tgttgtgggc attggataat cataaagtcc caacaaagta    4320
tgttacgctc atcaaggaca tgtatgacaa ggttgtgacc gtaagcagcg agactctaac    4380
tctcatcgag aggatgacac tacgagttgg ggcaattttc tgtttatttc tcacacacta    4440
ctcaaatgcc atactcacct aagggttgga gacacatatt tatagcccta gaggctgcac    4500
taccacacaa cacaacacac tacacaacaa gattgtcctc tagatgctaa aagctaaaag    4560
```

```
agactaaaga ggacagtcaa aaagctcctg ctgtcctcta gatgctaaag agactaaaga    4620
ggacagtcaa gatgctaaga tgctaaaaga ggacagtcaa aaagctcatg ctatcctcta    4680
gatggtcaag acttattcca tcattctccc cctaagtctt gggcgtcgtc ttgtgggaaa    4740
gtttggccat cccggacctg aagcaaagct caagaaactt gatcctccca aggggcttgg    4800
tgagcaggta tgcaagctga tccttggtgc tgatgtagtg cgccttgatg ctcccttctg    4860
ccaagcagtc tcagatgaag ttgtatctca cccggatgtg cttgctccgt tcatggaaca    4920
cggggttctt ggccaatact tgagcggact ggctgtccac cctgagttcc accgctccag    4980
tgtctctccc gaggagatca ccgagcagtc gagccaccca gagcgcctga gtcgaagcag    5040
tggaggccgc tatgtactca gcctcgcagc tggacatgac caccacctgc tgcttgatcg    5100
actgccagct aatgaggcac ttgctgagga agaagaggat cccgcttgtg ctcttgctag    5160
tgtcgatgtc accagcgtgg tcgctgtcgc tgtacccgac aaggtgtgcc tcccaagggc    5220
acctcgggta gtagagaccg tggtcgagag ttcccgcaac atagcggatg atcctcttca    5280
cagcctgctc atgctccgtc ttcggtcgct gcagaaaccg actaacgtag ccgacggagt    5340
atgccaagtc aggccgtgtg tggacgaggt agcgaaggct ccccacaaga cgccggtact    5400
gtgtagcgtc cacctccgtc gtgctgtcgc aactcagctt cagcctctcc atcggagtga    5460
gagctgggtt gcagtcggtg agcccagcca gctcaacaat gcgcttggct taggcggtct    5520
ggcgaagtgt gatcccggag tctccctggt gcacctcaat ccctaggtag gagagatgcc    5580
ccaggtcact catttggaag gtggccttca tctcttcctt gaacgctgcc acctctgcat    5640
ccttggcgcc ggtgatcacc aagtcgtcga cgtagacacc caccagcagg gcacttcctc    5700
cattgccccg ccgatagatg gccgcctcgt gcgggcttgg cgtgaagccc attcctttga    5760
gcgtggaatc cagcttggct ttccacgccc tcggtgcctg tcacaggcca tagagagcct    5820
tgcgcaggcg caacaccttg ccctccttgc cagggatcgc aaaacctagc ggctgttgta    5880
cgtagacctc ctcctttaag ccgccgttaa gaaacgccga cttgacgtcc atgtgatgaa    5940
cgtgccaacc ctccttggct gacaacgcaa ggaggagttg catggattcc atccgtgcca    6000
catgggcgaa agcatcgtcg aagtcgatcc cctcctgctg taagaaaccg tgtgccacca    6060
agcgagcctt gtgcttaacg atggcaccga cttcatccct cttcagtttg aacacccatt    6120
taagggtgat cgcgcgatga ccatgaggga gctcagcgag ctcccaagtg cagttcgtct    6180
caaccgcgtc catctccgac tgcatcgcgg cacaccaagc cgcgtgtttc tcggcctccg    6240
cgaaagaccg aggctcgcca ttgtcgcatg caagatgcaa cttcctgcc aaaatgcgag    6300 acgccgggcc cggcaccgac gggtcgatga aaggccctc cacctttcga taccgcaacg    6360
actcgccgtc gtagcacgcg tcgacgtgct cttcgtcgtg ggaaagcggg gtcacgagct    6420
ccactgggtc atgttcgaca cgacctggcg tcggagagga tgttcccggg gagggtaccg    6480
tcggtgctgg agtacgtggc gacggagagc tcgctggagc cggagtcgtg ggtggattgc    6540
gtggtggcga agagcttgtt gtagctagaa ctggagagtg tggtgttgga gtcagtggag    6600
acttgggggc tagggtaggc ctactcgaag aagggtcgcc tactcccccg gctccctcaa    6660
agtagacgta ctcgatggtg aagtcgtcat acgtcgagt cgtgccgtcg tccaccgcct    6720
tgtcccaggc ccatcctcgc ccttcatcga acactacgtc gcgcgtcgtg cgcacacgca    6780
gtgttcctgg gtcaaggatg cggtaggcct tcgagccctc cgcgtagcca atgaacaccc    6840
ctggggtgct cctgttgtcg agcttgccga tgtggccaag ctccttggtg aacgcgaggc    6900
```

-continued

```
agccgaagac ccgtaggtga gagaccgctg gcttgcgccc atgccaagcc tcgtacggtg   6960
tcatcccgtt gagtgccttg gtgggcgagc ggttgaggat gtagaccgct gtcaccaccg   7020
cctctcccca gaagacagcc gacattcccc tctgtttaag gagagcgcga gccatcccca   7080
caaccgtctg gttgcgccgc tcgatgacac tgttctgctg cgggctgtac gacgcggagt   7140
agtggcgctg aacgccctca tccgcgcagt acgacgcgaa ctcaaccgcc gttgtcggtg   7200
cgcagtacgc gcagcttgca gccgcactcc gcctccacag cgacctgcac acgcctgatg   7260
gcattcgtag cctctccctt gctaccaagg atcatcaccc acatgtagcg ggggagatcg   7320
tcgacgagca acaagaaata gcgtcgtcct cctggtgtgg ctggtgtcac cggaccacac   7380
aagtccccat gcacgagctc gagcgtctcc ttagctcgga agctcgactg ctggggaaag   7440
gggagccgtc tctgctttgt caacacacag acatcgcaga atcgctccac atggtcaagg   7500
cacggcaaac ctcgtaccat ctccttggca ctgagccgct tcagggcctc gaagttaaga   7560
atgttcgaag cgctcgtgcc actgccatgc cctgtcgtcc cgacgagcag caagacaaca   7620
aggttgtgcc accttcacgt tgaggatgta agccgattt ggactcctgc gtaccttggc    7680
aagaaggtga cgagagcggt cccagatcct catgactccg tgcttgacct ccacgtgcga   7740
accgttctca tccagctgtc ccaagttgat gatagagttc ctcaacgcgg ggatgtagta   7800
gactccggtg agcagcctgt gctcacctga cgtggcggtg aagacgactg agccggcgcc   7860
cttgatctct acgccggagg catccccaaa cttgacggag cctcggacgc tagagtcaag   7920
ctcggtgaag aactcccgtc gaccggtcat gtgatgagtg cgccggtgt cgaggcaaca    7980 tccttcgatc atatctttgc tggagccgtc gccgaggaaa gcgcgtgctt tcgactcatc   8040
aaggtggagg agtgccgctg cggccggtgc cgctggagat agctctatgc ttacatgtgc   8100
taggagcaga gcctcccgct ccgcctccgc ctgtgcgacg ttggtgtggc cacgtcgtgg   8160
ctgtcgacag tccctggccc agtggccaag cttgccacag ttgtgacagc cgttgtctcg   8220
tgccggcttc ttgttgccga cggccccgcc ttgggcacct ccacgggcac cacccctcagc  8280 atgtcctcgc gccccggcct gggcgcctcc acgcgcttg cgcggcttgc gcgtttgcg     8340 gcctcgtgtc gaggaggact ccccttctt cttgtcaccc tggcaggcct cccactgctc    8400
ccgagtgaga tgtagcttcc cgtcgataat gataggccca gagggagtct gtggttcgtc   8460
gccatcgacc accttgagac gacctatcgc ctcttcgatc gtcatcgtgg agaggtctag   8520
cagagactcg atcgagcgag caatctgctt gtacttctcg gggatgcaac ggaagagctt   8580
ctcaacagct ctcttctcat cataggcgtc gtcgccgaac tgcaccatct tctgcaacag   8640
tgttgaggcg gaaagcaaag taatcaacat cctcacctgg cttgaaggct aggttttccc   8700
actccttgcg aagtgcctgt agtgtggtct tgcgggcacg atcgctgccg atgcgggtcg   8760
cagcgatggc gtcccaggcc tccttggcag tccgcttctg ggaaagcgaa aactgcatct   8820
cgagcgggac tgcagcaatg agggcatcca gcgcccgtcg atcctcgtgg tagtcgacgt   8880
cgccataccg aactgcttcc cacatgtggc gaacctagag ccatacccctc atcaccgcgg   8940 cccactcgac gtagttggtc ttggtgaggg taggccaccc accgccggga ccgatgtccc   9000
tgacaatggc ctaggccatg cgacgaccat ggtaccgatc cggggaggga gagccgcgtc   9060
gcctagaggc cgcgatctcc gtccactcgg tcgccgtcgc caggagcacc gccggcgtgt   9120
ctatgcccgt ttgggctgcc gccgcatgcg ccctcgcccg gagcgccatc ggcgcgtcgg   9180
cgcctatctg ggctgccgcc acgtgcgccc ccatggggat gcgcggctgc ccactgtgtc   9240
ggctgctctc gcgctgcttc cctcgccagc ctaagctctt cgtcggtgtt gtcgtcgata   9300
```

-continued

```
gaagcagagc tgccggctct actgccgcgc agagcctcga gctctgttgc cgccgcacgt    9360
gcagcatccg tcgcctccgc tgcttctact tccgctctcg ctgctgccag ttccgccgcc    9420
gccagccgtg ctgccctcgc cgctgtcgct gcttccgctg ctgctgctcg ctcgcgttct    9480
tgtgccgcgg cgacctcggc ctcctgctgg cgccgcgcac ttgaagtgac cgagcgtagg    9540
gacatggtgg gctagtgagg gatcgctgcg tgtggaagag gctgtctcag acgaaaggct    9600
gctcgtccga gcaggagagg aaggaacagt tggagctctt gttgtcgact gagtgtgggg    9660
agaggcgtga gaaggagatg agcaaaagat gtttaggctg taggatagtt tggttctgat    9720
accaattgta agcagcggga ctctaactct catcgagagg atgacactac gagttgggc     9780 aaattttgt ttatttctca cacattactc aaatgccata ctcatctaag ggttgggaga    9840
cacatattta tagccctaga ggctgcacta ccacactaca caacacacta cacaacagga    9900
ttgtcctcta gatgctaaaa gctaaagaa actaagagg acagtcaaaa agctcctgct      9960
gtcctctaga tgctaaagag actaaagagg acagttaaga tgataagata ctacaagagg   10020
acagtcaaaa agcccctgct gtcctctaga tgctcaagac ttattccatc agtgactagc   10080
gtccgaacaa ctgtggtgat acaaatgttt ttcagattaa catagcacta catcaaggtt   10140
cagctttgag cccttatcta tttgccctag tgatagatga ggtcacaagg aatatacaat   10200
gagatatccc ttggtgtatg cttttcgctg acaatgtagt tctagtagat gaaagccgag   10260
aaggagtaaa tagaaagcta gagttatcac gtcagaccct agagtcaaaa ggatttagaa   10320
ttagcaggac caaaaccgag tatatgagat gtgactttgg tactacaatt agtgaggatg   10380
gagatgggac tggtaccaaa gaaggacacc tttcattatt tgggatcgat gctacagaga   10440
gatggtgata ttgatgaaga tgttagctgt aagatcaaag cggggtggat gaaatggtgt   10500
caagtatcgg gtgtcctatg cgacaagaga gtgccacaga agttgaaagg caagttctac   10560
aggacggcga ttaagcctgc tatgttatat ggggttgagt gttggcctac taagagacga   10620
catatccaaa aactaagtgt cgcggagatg cgtatgttgc gttggatatg tgggcacaca   10680
agattggacc gagtgagaaa caatgactta cgcgatcggc taggagtggc gccaattgaa   10740
gaaaagctta ttcaacaccg gttgagatgg tttgggcatg tccaccggag acccccagag   10800
acaccagtgc acagagccat tataaaacag gacaataatg tgaagagagg tagagggcgg   10860
tcaaacttga catgggagga ggcaatcaaa aggaacttga aggaatggta tatcctaatg   10920
gagttgtgtt tggatagaag tgcttgaaaa aaagctatcc atgtgcccga accgtgacta   10980
ggccttttct cttttagtgc tctcaaaagc ttttttctct ccccttttctc tctctttctc   11040 tttttggtga cttcttgttg ggtttcaact ttagcctacc ccaacttgct tgggactaaa   11100
aggctatgtt gatgttgatg atgttcccaa aaaccatgtt ttgtgtaaga gactgtagtc   11160
cttggtgtat tataggagat ggggtccaat atatagactc acatgaccct aaccctaatg   11220
ggccggcagc ccaacagtgg tgccgaccca cacacacagt ctaacatccc ccgcagttgc   11280
aacgggggca ccacacacga tgagactgga gtagaagccg aagggttgaa attccccgc    11340 agtcgcagcg tcgtgagggt acgaatgttg cggctggagt agagaccgat gtgtactcca   11400
agaagacgat agccccaaga tgtcgaggta gccgaagtcg aagtggctgt ggtcgggaga   11460
aacgcagcag tagcctgttc tttgggaggg gtcgacgttc gagcgtcaac gatcgacagg   11520
acgacacaaa aggacagcaa caacctcagg gccttcttgc ttcgatccgc gaccggtcgt   11580
cgaggagcct cgccagggag gccggcaata gtgcacgctt ctgcgccagt cagggtggcc   11640
```

```
gtgcccatgg cagaaaagaa ggggtatcgg cggatccggt cgggaaagcc acgacaacga    11700
cggatccaac catgaagaca acgatctgac taaagggttt agggaaggag gacgcccgtc    11760
ggccatgcca gagggccggc agcggctggg gtggggctgg acctaggggc agaggctggc    11820
cggcggttgg ggagggaaac ctaaccctga tgccatgtaa gagactgtag tgcttggtgt    11880
attgcatagg agatggggta caatatatag actcacatga cccaaaccct aatgggtcgg    11940
catcccaaca gtggtgctgg cccacacaca cagtctaaca ttttggggtg attttttgga    12000
agtcttttgg agatggtctt agatccacca aatataagtc catcacaact ttgtgacatc    12060
ttttatcttc attcttccat tccatgtcta tacttgctta aaggcgctct aatcaattca    12120
gtgaacttgt tatctaccat tctaccttaa cttagcaaca attggtggca gtagggtcat    12180
tgtattcctt accttaatct tgtgccagtg tccaaatgga ctatcagagg gagtagtata    12240
ttatcagcat tttggttgag ggggatccca agatttactg tttgagttta atacatgttt    12300
tttattgagt tatgtcaact aaagaaactc tatacttctc tctgcctgaa gtaaataata    12360
ttatctgttt tgcaatgatg ctcgatacct tttatttttgt ctctgcttca cctatacttt    12420
cattgaaccg tatgacaatg ccttaatttt ttttccttcg atgtatgatt gtgcagtatg    12480
gccgtatttt ggatattgac ttgaaaatac ctccgagacc tcctggatac gcattcgttg    12540
aggtgaggct attttgctat tgtctgaatc tgtaagaacg atacattctt ttatggggcc    12600
tgcttttaaa tacatgcaac tgctccatta ctgtgttcag ttttaaaata tattttttcag    12660 catgctttaa ccttttcaaat caaactgact gatataatta atttcttttg atgtcaccaa    12720
acatttggtg ctaacaaaaa aatgatgctt ttatagtttg aggatccacg tgatgctgat    12780
gatgcaattt atgccgtga tgggtataac tttgatggct acaggttgag ggtatgtata    12840
tcaagctttc atttaatggt tctcctagaa gagaggattg atttgtgttt tcttgcattt    12900
gctgaaaatg cattctactc aggttgaatt agctcatggt ggcagaggcc agtcttattc    12960
ttatgatcgt tcaagcagct atagcagtgc atgccgtgga ggtgtttcta ggcgctctga    13020
tttccgtggt tggtacttct gtcatatgag aaagttttact tttagctcct tacacagact    13080
ctcaagtttc atttattgaa tcatgcagtt atggtcactg gtttaccctc atcggcatcg    13140
tggcaagatc tgaaggtaat ttcttttataa ttcacttatt ccaggacctg ctggaaagaa    13200
ctcattacta catttcagga ccacatgcgg cgcgctggtg atgtctgttt ctctgatgta    13260
taccgtgagg ctggaggtta gttgttaaga accccctggac acgtttattg ctatttcatt    13320
acagcatatg gtgttaaaca taatccccaa ttttgtaatc attgtttcct aacttattgc    13380
ttcactgccc ctttgaagta tgatgaaata ttcgggcttt attatgaatt tctacatatt    13440
aatgatattt gctccttttt tcttgtgctg cagaaactat tggaattgtg gattatacaa    13500
attatgacga tatgaaatac gcggtgggtt tagaatgccg tttattcatt gcttctaatg    13560
tgcacttaaa accattttttt ctcatctgtt cagacgatct gttttattgt tgaagagagt    13620
tctctaattt ttatatgttc tttcctgttt catttttttag ataatggaaa aatcatccga    13680
ccttggcctc aaatgaggtt acggccattt attacaaggg acggaggcat attgccaaaa    13740
ctcctcctat gaccacatca gagaacccca actagccaaa ttgaagaact tcagctaccg    13800
aaccacagct actacatagt taaacgcaac gcataccccc atccaaaatt gctaaagaay    13860
tttagtagca ccctctccac attacgacat gaagacttta ttaactcttg gtcctccctt    13920
ctaggctgaa cctgagacca gaagcggcac caatatgttg ctctgaaggc tacctgcaca    13980
catgatttag gagatgaatt attgaacacc acatcatttc tacttaacca aatagcccaa    14040
```

```
caaattgccg atgcaacggt taatagtaag tttcgcactc tgggaagcct cccgctcgcc    14100
caaaccccaa acaaatcatt aacatcccga ggaggtctca accccgtgct tatctgaatc    14160
aaccgccaaa tgaatgacgc atacaaacaa ctgaaaaaca ggtgctttat tgtctccggt    14220
ctactacaaa agcaacatat cttattacca ttccaatgcc tcctagccaa gttatccttt    14280
gttaatgtta cccctctttt gaggtaccac ataaaaatct taattttcag aggaagccta    14340
agtttccaaa ggtccttatt atccacccc atcccattgt taagagatgc cagatacaga    14400
gacttaaccg taaacatccc gttggcggtc aagttccatc tgaacaagtc cctgtttgaa    14460
ttcaattcgg tatgcgcaac aagtgagacc aattgaaacc attggaccct caactgttga    14520
gccaaacccc tccgaaagga aatatttaag ggcaccgtgg agaacacaca ggcaactgtt    14580
gagttcttcc tcgctaggtt ataaagagac ggaaaacaga gttttaacgt tcccgacccg    14640
agccaatcat cctcccagaa acgcacctgg gacccatcat gaatcacaaa ggttccttta    14700
ctaatgaatg tgtccttaac tttcataaga ccactccaga agtgtgaatc agtggccctg    14760
cgctgcgcct gggataaggt tcgattggcc agatatttac gtctcaataa tgattgccac    14820
attccttctt cattgagaag tttatacaac catttgttta agaggcattt attatgaacc    14880
tctaaattca aaatgcctag cccgccaacc tccttaggtt gacaaattac atcccatttg    14940
gccagcctat attttttctt atggccctcc ccttgccaga aaaacgcga tctgaaataa    15000 tctatcttct ccagcacacc ttttggtacc tcaaagaaag acatcataaa catcgctaga    15060
ctggtcaaca cagaattaat taatacgagc cgccctccta ctgacataag ttttcctttc    15120
caactactga gctttttctc gaattcggcc tccactgttt tccactcacc aattgtcaac    15180
ctacggtggt gcataggaat cccaagatat ctgaagggca gcccaccaga actgcaacca    15240
aacagccgtg tgtacctccc ttcatcctct tttgccttcc cataacagaa tacctcactc    15300
ttgtgaaagt ttatttttaag accagataac tgctcaaagg cacataatat gagcttcata    15360
ttcgttgcct tttccagatc gtgatccata acaaaattg tatcatcggc gtattgcaga    15420
atggataacc ccccatctac caaatgcggc accaagccct tgatctggcc attttccttt    15480
gctctattaa tcagggtagc aagcatgtcc actaccaagt taaagaggat aggagacagc    15540
ggatcgccct gcctcacccc tctttgggtc tggaaaaaag gacccatgcg atcattaact    15600
ctaaccgcaa catggccccc cttcatgaaa gactcgatcc aactacacca ggtacttgaa    15660 aaaccttca tacgaaggga ttgttgaaca aagctccact tcaccttatc ataagctttc    15720
tcgaagtcga ttttgaaaat gacccatcc cttttcttcg tatgtagctc atgaatagtc    15780
tcatgtaaga ccaccacccc ctccatgata tttcttcctg gcaggaacgc agtctgcagg    15840
ggactgatta cattctgcgc aacctccgtg atcctcttag tcgcaacctt tgtgaagatt    15900
ttgaaactga catttaggag acaaattggt cggtattgtt gaaccgagat tgcctcccga    15960
gtcttaggaa gcaaaataat agtcccaaag ttaagactat acaaagggag attccctgtg    16020
tgtaactcac gaaacaaagc cataagatca tctttaataa catcccaaca gatttgataa    16080
aattccgccg ggaatccatc aggacctgga gccttgttat gttccatact aaaaaccacc    16140
gcttttactt catcttcaga aaatggctgg gtgagcttct cgttctcaac ttgagtaact    16200
tgtattatat catctctaag atcctcatcc agagtaaaag acgtgctttc tgggggggcca    16260 aagagatttt tataataacc agttatatga cttttaatt ctccctcgtc gtataacata    16320
cgagctccat ccgtcatctg gaagattcga ttcttcctga attttccatt ggctatcatc    16380
```

```
tgaaaatatt tagtattact atcccctcc aggagctcct tgaccttcgc tctttgatac   16440
cactttattt cctcctcccg gagtagctga gcaagcctgt tctgtaagta gttgcgcaga   16500
tccaactccg cagtactcaa cagaactatt tcagctctct tatctaaatc atcaagctta   16560
gcgatgatct cctttttcc ttttcaaca accccgaagt gtgcattgcc caacccctta    16620
agtgttggcg taccttcttt atcctggctt gccatttctc caaggagta gaacctcttg    16680 tctcatttac ccaaatatct tttaccatat ccacaaaacc atccctcaga aaccagccta   16740
gttctaactt gaacggagga attgtttggg cggttacaac acctgtacta agaaacagag   16800
gagtatgatc ggatatattt ctcgacaagg catgtaccga agctctaggg tattttccct   16860
cccattctgt agctagcaaa atccgatcca acttctcata agtcggaata tccctagtat   16920
tagcccaggt gtaccttcgc cccgacatct gcaattatct tagatcaaga ccatcaatta   16980
ccgcattgaa taggaacggc caacgatgat caaatctatc attatttttc tcagatggag   17040
atcataaaat attaaagtct cccccaatga gaataggtaa cgtttctgta ttgctcaaac   17100
ggactagctc agaaaggaat tcttgtttga agcagtcctg ggcagggcca tacaccgaga   17160
caagagccca tttaaaacca tctgccttat catgcaaatt aaacttaata agaaatccc    17220 cttccgtgat ggcaccaaca tcaaagacat cagcgtcaat tcccaacaac atcccccag    17280 atctaccatg aggttctttg caatgccaga taaatttttt cccagcacac aaattcctta   17340
gtagatgatc tgggaaggat ttgcggcctg tttcagagag ggcaataaaa ttgagaccgt   17400
gttctttggt cagatccgaa acgtatctaa gcttttcaa atccttgaac ccattgctgt    17460
tccaaaagat tcctttcatt ggtaaacaat taattaataa tcaagctcga cctttttgt    17520 tagaacacaa cgaaccctga ctagatggtt ttgtacagac tgacttaatc agcccatcag   17580
tgccatccgt ctcttcattc ataatatccc cacacaaatg atttaaaatg aaatgatcaa   17640
actcttcgtc ctctactact ccccttcccca taaaatcaga taattcagcc ttgttcttac   17700
ccactagctg atcctgaact ctattaatct aaaatttttt caactgacca atagaggaag   17760
caactaaact aggattagaa tccgctaaaa tgccaatatt tttaaaagaa tcaagaatat   17820
aattatcggg taaactaata aaggaaacat tgttaccttt agtcggctgg tcgtccaggt   17880
tgtatcccgc tttcagccgt actgctcgaa caagcgagtc ttcactcacc gaatctgagc   17940
ggcgcgagct acgacgcagt gcttgcactg ttcctcatgt gtcatgattt taatcatgca   18000
ttttcctctt gtcatcctgt agattaggaa gcttgatgac tcacagttca ggaatgcatt   18060
ttcaagagca tatatcaggg tatgtattct catgtttgcc ccagtttagt tttggaaatt   18120
gttacaatgc tttgcatcat gtctatttga ttatgaatta ttttgattct tattctatta   18180
taggtgaggg agtatgatgc tagatcacga agcagaagcc gtagccactc gtactctaga   18240
agccccagct acagcaggag caggagtcca aagtatgtat acatgctgac aaatttgata   18300
tccaagtcag atggcagcac taattctttt ttgttgttat ttagatctgt ttctcagtca   18360
ccctcatctg tggatgaaag gtatgtgaat ctatgtcatt tagaaatgta catttgtgaa   18420
actgagagtg ctaatattgt tcgaaggaac ccgattgtca aataaatggt gaaagcaatc   18480
agatcttgtt gtgaatcatc attgatgtat tctgcactac acctatggcg ctaaaaatat   18540
ttgaatatga catgtcatca ttttgtatac aagcttaaag cagggccatg gtggatgtaa   18600
caactgatag gagattgcac attaacttaa ttatttccta ctatctgata cactttcgtc   18660
aaacaacgaa atgcctttcc agagctgaga ctgccttata caaacttcta caaatacagc   18720
ttaagttttt aagtgtgtgc tctaccctaa ccttatagaa catgctgaag gtttggctca   18780
```

```
caaacttcta gataaatctt tcaatgtcgt agcagggagt attagatcca tcagaagctt    18840
gccaaattga gagggtatat aaagaggtgt taccagaact ttccttcttt caaaacaata    18900
gttttgtcgc cttttcctgt cgtatcagtc gtctacatag catgccaaaa cccctctgtt    18960
tcttttccct catggaaaag cttcagtccc cttcttattt atcaacttca tacaacatta    19020
acccatagtt atcatggcag cgcgtaggcg ctgactaggc atccaagcgg tcggcagtgg    19080
atgccatgcc tcgtcgcctc gcctgaaccc agttaggcga tggtaagaca tctcctagaa    19140
gcccacctag ctgttgaact aggctttaat gggtctgcct tgtgcactat acgcccagtt    19200
tcctcttctt tcctctgctg ccaccaccgt tagagccgct agatcgctca cgccggctgc    19260
ctgccgcgtg cctgtgccgc gcgcccgcgt ggcctacaca gtgcaccgcc cacaagtcgc    19320
ctacaccagc gttgctcgtg cgtcgtgccg cctgagctcg accatggatg cttgctactt    19380
gctggattta tatttatttg ctagttttc atatatcatg tgatatatga ctatatgttg     19440
cattttgct gctggagaaa agggcgtctt ggcagcacct aggcggttgt ctagaaccta     19500
ggcgtctagg tgaccggctg gcgagaccgt ggcgccatga taaccatgca ttagcctaga    19560
gctcttttt ctgagttgta acaacatatt ttcgtgtttt atattttaaa cgtagaaaaa     19620
gactacagat aaaattcacc ccagatttta atgataataa caatatattt caaaagattt    19680
ttttctgttt tttgttaaag caagaggaaa acaaagtaa ggtgccagaa ttttaacttg     19740
atatactttg gaacacctac taaaatcatc tgtgttatgt tattttttg atgtattgat     19800
atctctttaa attagtataa cttttgtgt tgtactgatt tctctttaaa atagtatgac     19860
ataaatttgc tctgtggttc aatgattaaa cataccgagc ttgttggcta acctccattg    19920
ttcaaggttt gcttttgttt ttcctagatt tggccatgcg gcgatctggg ggctgcattg    19980
atataatact ggatgttttg agaatcggag tggatggttt gggacttcgg atagtagaga    20040
tggattgtga tgcatgtatg acaagtgggc tacaatcagt cctaggagca agataggctg    20100
acagtaagaa aatgtgaagt aaagcttgtg gtgttattaa aacaaatgtc tactattaag    20160
ttcaatgacc ccatatagat ggacagtaat ttataggttt gtgttttgt ttaactaatg     20220
ctgccaccct agtaaaaatt tctatggcgc cttttgcatt ttggctctct ttagccattt    20280
ccttgtcaag gttcacacta gccgaagttg acattacaac aaaattcagt atacacattg    20340
ctttgtttgc ttatttgtat tccagttatg agctaattac ctgataggct gaaaatctat    20400
attattttc tgagagtatt accataaaca ccaaaatgtg tccttacatt gcagcttcgc     20460
tcctgtttca gttcattcat atgcccgtgg aatgttgcct ctttattcac atctcgagtt    20520
gccagtttaa ttttttatcac aattttatat tcagatatta gagtgctact aacacatcca   20580
ttaaagtaat ggaatttgtt tcttgtacct tctgcagaat cgctatcaag atctcgatcc    20640
ccaatttctt ctgtaagtat cccacgctca tttccaaccg agcttgtcat aatcgtcttg    20700
ttctatgcaa ttgatttaac tcatttgcag ccttctcatg caagatatgc gacaagccct    20760
aggagcagaa gcgcatcccg ttctcggtct cctgtaattg caagcttcca aaacaaccat    20820
ttattatgtt gctaggaact ttcattctta tttagtattt tcttgctgtc aggtgagatc    20880
cgattgaact ttgagagccc ttgaagcagt gagcagcccc agggagaaga aaggaacttg    20940
agagtatgcc gtgccatcac aatggtccga gtgattatgc tgttgccact gctccctcac    21000
atttaagagg tttcctctta tttagacggc gcatttaatt aacattatct tgctaaagag    21060
agacttatgc gtagtctact tgtgtactcg ttcgtttgtc ctcatgttct tggcttcagg    21120
```

```
aactctggtt ttttatcatt gtacccatag taaaacctag atgtagttgg ggtatgccgt    21180
atgcgtctat attcggttgg tcgaatgtaa atctggatgc atatatgcat ctgtttggtt    21240
tcatttaggc ctttccttgg tttcgtgatt aatgacaaca taagcttatt gctgtgatc     21299
```